United States Patent
Waterson et al.

(10) Patent No.: US 11,318,137 B2
(45) Date of Patent: May 3, 2022

(54) QUINAZOLINE COMPOUNDS AS MODULATORS OF RAS SIGNALING

(71) Applicant: VANDERBILT UNIVERSITY, Nashville, TN (US)

(72) Inventors: Alex G. Waterson, Murfreesboro, TN (US); Jason R. Abbott, Nashville, TN (US); J. Phillip Kennedy, Nashville, TN (US); Stephen W. Fesik, Nashville, TN (US); Qi Sun, Vernon Hills, IL (US); Jason Phan, Nashville, TN (US); Michael C. Burns, Chicago, IL (US); Pratiq Patel, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/500,369

(22) PCT Filed: May 17, 2017

(86) PCT No.: PCT/US2017/033182
§ 371 (c)(1),
(2) Date: Oct. 2, 2019

(87) PCT Pub. No.: WO2018/212774
PCT Pub. Date: Nov. 22, 2018

(65) Prior Publication Data
US 2020/0253974 A1    Aug. 13, 2020

(51) Int. Cl.
| | |
|---|---|
| C07D 239/95 | (2006.01) |
| A61K 31/517 | (2006.01) |
| A61K 31/5377 | (2006.01) |
| C07D 401/10 | (2006.01) |
| C07D 401/14 | (2006.01) |
| C07D 403/10 | (2006.01) |
| C07D 403/12 | (2006.01) |
| C07D 405/12 | (2006.01) |
| C07D 405/14 | (2006.01) |
| C07D 409/12 | (2006.01) |
| C07D 413/10 | (2006.01) |
| C07D 413/14 | (2006.01) |

(52) U.S. Cl.
CPC ........ *A61K 31/517* (2013.01); *A61K 31/5377* (2013.01); *C07D 239/95* (2013.01); *C07D 401/10* (2013.01); *C07D 401/14* (2013.01); *C07D 403/10* (2013.01); *C07D 403/12* (2013.01); *C07D 405/12* (2013.01); *C07D 405/14* (2013.01); *C07D 409/12* (2013.01); *C07D 413/10* (2013.01); *C07D 413/14* (2013.01)

(58) Field of Classification Search
CPC ........................... A61K 31/517; C07D 239/95
See application file for complete search history.

(56) References Cited

U.S. PATENT DOCUMENTS

| | | |
|---|---|---|
| 2008/0051398 A1 | 2/2008 | Cai et al. |
| 2010/0068197 A1 | 3/2010 | Anderson et al. |
| 2015/0080409 A1 * | 3/2015 | Manetsch ............ C07D 239/95 514/252.17 |
| 2016/0068496 A1 | 3/2016 | Thompson et al. |

FOREIGN PATENT DOCUMENTS

| | | | |
|---|---|---|---|
| WO | WO1992014716 A1 * | 9/1992 | ........... C07D 239/48 |
| WO | WO2003055866 A1 | 7/2003 | |

OTHER PUBLICATIONS

Abbott, et al., Discovery of Quinazolines That Activate SOS1-Mediated Nucleotide Exchange on RAS; ACS Med. Chem. Lett. 2018, 9, 941-946.

Akan, et al., Small Molecule SOS1 Agonists Modulate MAPK and PI3K Signaling via Independent Cellular Responses; ACS Chem. Biol. 2019, 14, 325-331.

* cited by examiner

*Primary Examiner* — Paul V Ward
(74) *Attorney, Agent, or Firm* — Stites & Harbison PLLC; Richard S. Myers, Jr.

(57) ABSTRACT

The present invention relates to quinazoline compounds and compositions that modulate Ras signaling. Compounds and compositions of the present invention are useful in the treatment of cancers and other disease states associated with Ras dysfunction (e.g., Ras-associated autoimmune leukoproliferative disorder, or certain types of mitochondrial dysfunction) in a subject, for example a mammal or a human.

41 Claims, No Drawings

QUINAZOLINE COMPOUNDS AS MODULATORS OF RAS SIGNALING

RELATED APPLICATIONS

This application claims priority from International Patent Application No. PCT/US2017/033182 filed May 17, 2017. The entire disclosures of which are incorporated herein by this reference.

BACKGROUND

Ras is one of the most highly validated targets for cancer drug discovery; however, the discovery of potent inhibitors of Ras has been difficult due to a lack of suitable binding pockets on the surface of Ras. The present inventors have discovered a binding pocket on the SOS protein, as part of the trimeric Ras:SOS:Ras complex and dimeric Ras:SOS complex, and small molecules that bind to this pocket and alter Ras activity in biochemical and cell-based experiments. These compounds are useful for treating cancer.

Without being bound by theory or mechanism, the Ras family of small GTPases function as molecular switches, cycling between inactive (GDP-bound) and active (GTP-bound) states to relay cellular signals in response to extracellular stimuli. The activation of Ras is tightly regulated by guanine nucleotide exchange factors (GEFs), such as Son of Sevenless (SOS), which catalyze nucleotide exchange, and GTPase-activating proteins (GAPs), which aid in GTP hydrolysis. Upon activation, GTP-bound Ras exerts its functions through protein-protein interactions with effectors such as Raf kinase and phosphoinositide 3-kinase to promote cell growth and survival.

Aberrant activation of Ras by increased upstream signaling, loss of GAP function, or oncogenic mutation results in the deregulation of cellular signals in cancer. Indeed, aberrant Ras signaling plays a role in up to 30% of all human cancers, with the highest incidence of Ras mutations occurring in carcinomas of the pancreas (63-90%), colon (36-50%), and lung (19-30%). Active Ras endows cells with capabilities that represent many of the hallmarks of cancer, including the ability to proliferate, evade programmed cell death, alter metabolism, induce angiogenesis, increase invasion and metastasis, and evade immune destruction. Importantly, inactivation of oncogenic Ras has been shown to be a promising therapeutic strategy in in vitro and in vivo models of cancer.

Embodiments of the present invention include compounds that increase the rate of SOS-mediated nucleotide exchange on Ras by binding to a functionally relevant, chemically tractable pocket on the SOS protein, as part of the Ras:SOS:Ras complex. High resolution X-ray co-crystal structures reveal the location of the binding pocket in the CDC25 domain near the catalytic site of SOS, adjacent to the Switch II region of Ras, and provide a detailed understanding of protein-ligand interactions. Mutational analyses confirmed the functional relevance of this binding site and showed it to be essential for compound activity. Perturbation of Ras signaling in HeLa and other cancer cells with these molecules demonstrates their ability to alter Ras activity in the setting of full-length proteins as well as cause cell death. The present invention is a new approach for targeting Ras signaling and provides compounds can be used to treat Ras-driven tumors.

Early attempts to inhibit Ras-driven tumors have focused on disrupting the posttranslational modification and localization of Ras or inhibiting Ras effectors. In contrast, embodiments of the present invention include compounds that activate nucleotide exchange by binding to a hydrophobic pocket on the SOS protein, as part of the Ras:SOS:Ras complex. Further, these compounds perturb Ras signaling in cancer cells and kill cancer cells. This discovery represents a new approach to alter Ras activity, and the compounds reported here may serve as starting points for the discovery of more optimized compounds that target Ras-mediated signaling.

Compound-mediated activation of SOS-catalyzed nucleotide exchange of the present invention is novel compared to previously reported mechanisms that increase nucleotide exchange. Mechanisms involving chelation of the divalent magnesium ion, destabilization of bound nucleotide, or activation via the allosteric Ras binding site on SOS were inconsistent with the results obtained in in vitro nucleotide exchange assays. In contrast, the present inventors discovered compounds of the present invention that increase nucleotide exchange by binding to a hydrophobic pocket on the SOS protein, as part of the Ras:SOS:Ras ternary complex.

Based on in vitro biochemical studies, the present inventors discovered that treatment of cells with compounds of the present invention resulted in diverse set of cellular responses. Indeed, Ras-GTP levels increased following the treatment of HeLa and other cancer cells with the compounds of the present invention, consistent with the observed increase in nucleotide exchange activity. Treatment of HeLa and other cancer cells would result in an increase of in downstream MAPK pathway signaling at low doses, but a decrease in MAPK signaling at higher doses. Further, downstream PI3K pathway signaling decreases in a dose-responsive manner. The present inventors thus discovered that rapid SOS-mediated activation of Ras, in the absence of other cooperative signal inputs, perturbs both MAPK and PI3K signaling.

SUMMARY

In accordance with the purpose(s) of the invention, as embodied and broadly described herein, the invention, in one aspect, relates to compounds useful as modulators of Ras activity, methods of making same, pharmaceutical compositions comprising same, and methods of treating cancer associated with alterations in Ras activity. Further disclosed are methods and pharmaceutical compositions useful for treating a disease related to Ras activity. In one aspect, the disclosed compounds can affect the efficiency at which SOS can activate Ras. The disclosed compounds can also affect the activity of the Ras:SOS:Ras ternary complex. The modulator of Ras activity can offer advantages over a molecule that blocks the GTP/GDP or SOS binding pockets, since basal signaling would not be inhibited.

Disclosed are compounds of the following formula:

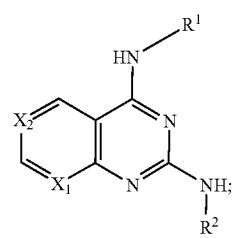

wherein

X₁ is selected from $C_{1-6}$—$R^A$;

X₂ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; provided that when $X^1$ is C—H, $X^2$ is CH, and $R^1$ is furan, $R^2$ is not phenyl and where $X^1$ is C—H, $X^2$ is CH, and $R^1$ is benzyl, $R^2$ is not phenyl.

Also disclosed are methods for enhancing SOS mediated nucleotide exchange on Ras in a subject comprising the step of administering to the subject at least one compound having a structure represented by a compound of the following formula:

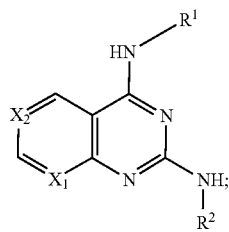

wherein

X₁ is selected from $C_{1-6}$—$R^A$;

X₂ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; in a dosage and amount effective to modulate Ras signaling in the subject.

Also disclosed are methods for modulating Ras signaling in at least one cell comprising the step of contacting at least one cell with at least one compound having a structure represented by a compound of the following formula:

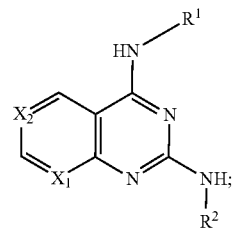

wherein

X₁ is selected from $C_{1-6}$—$R^A$;

X₂ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof, in at an amount effective to modulate Ras signaling in at least one cell.

Also disclosed are compounds having a structure represented by a compound of the following formula:

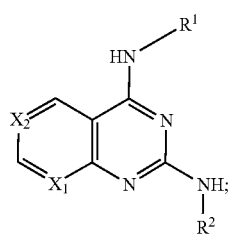

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof.

Also disclosed are pharmaceutical compositions comprising a compound having a structure represented by a compound of the following formula:

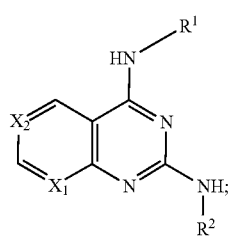

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring; or a pharmaceutically acceptable salt thereof or a pharmaceutically acceptable derivative thereof; and a pharmaceutically acceptable carrier.

Also disclosed are methods for modulating Ras signaling in at least one cell comprising the step of contacting at least one cell with at least one disclosed compound in an amount effective to modulate Ras signaling in at least one cell.

Also disclosed herein are methods for modulating Ras signaling in a subject comprising the step of administering to the subject a therapeutically effective amount of at least one disclosed compound in a dosage and amount effective to modulate Ras signaling in the subject.

Also disclosed are methods for the treatment of diseases associated with dysfunctional Ras signaling or cancer associated with dysfunctional Ras signaling comprising the step of administering to the mammal at least one disclosed compound in a dosage and amount effective to treat the disorder in the mammal.

Also disclosed are methods for making a compound comprising the steps of providing a quinazoline compound having a structure represented by a compound of the following formula:

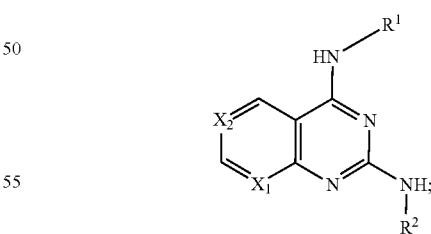

As shown in the Examples below, wherein the variables are defined herein.

Also disclosed are the products of the disclosed methods of making compounds of the present invention.

Also disclosed are methods for the manufacture of a medicament for modulating Ras signaling in a mammal comprising combining a compound of the following formula:

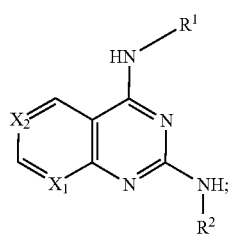

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring; or a pharmaceutically acceptable salt thereof or a pharmaceutically acceptable derivative thereof with a pharmaceutically acceptable carrier.

Also disclosed are the products of the disclosed methods for the manufacture of medicament.

Also disclosed are uses of a compound for modulating Ras signaling in a mammal, wherein the compound has a structure represented by the following formula:

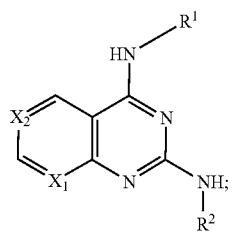

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring; or a pharmaceutically acceptable salt thereof or a pharmaceutically acceptable derivative thereof.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

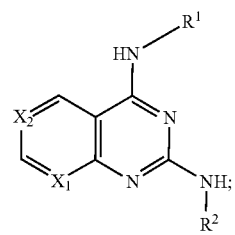

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, CF$_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; with a drug having a known side-effect of increasing SOS activity.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

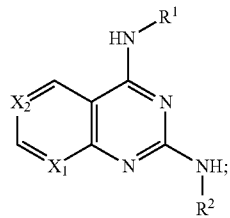

wherein

X$_1$ is selected from C$_{1-6}$—R$^A$;

X$_2$ is selected from C$_{1-6}$—R$^B$;

R$^A$ is optionally substituted with one or more Z, and selected from H, alkyl, alkyl-amino, amino, amine, cyano, —OH, alkyl-OH, N—(CH$_2$)$_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

R$^B$ is optionally substituted with one or more Z and selected from H, alkyl, aminoalkyl, cycloalkyl, alkoxy, halogen, cycloheteroalkyl, aryl, heteroaryl, R$^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

R$^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, CF$_3$, alkoxy, alkyl-alkoxy, OH, O—CF$_3$, O-Me, acetonitrile, Cl, F, Br, cyano, CF$_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; with a drug having a known side-effect of modulating Ras signaling.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

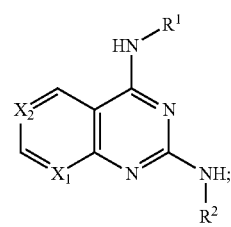

wherein

X$_1$ is selected from C$_{1-6}$—R$^A$;

X$_2$ is selected from C$_{1-6}$—R$^B$;

R$^A$ is optionally substituted with one or more Z, and selected from H, alkyl, alkyl-amino, amino, amine, cyano, —OH, alkyl-OH, N—(CH$_2$)$_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

R$^B$ is optionally substituted with one or more Z and selected from H, alkyl, aminoalkyl, cycloalkyl, alkoxy, halogen, cycloheteroalkyl, aryl, heteroaryl, R$^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

R$^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, CF$_3$, alkoxy, alkyl-alkoxy, OH, O—CF$_3$, O-Me, acetonitrile, Cl, F, Br, cyano, CF$_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; with a drug having a known side-effect of having anti-cancer activity.

Also disclosed are methods for the treatment of diseases associated with dysfunctional Ras signaling in a mammal comprising the step of co-administering to the mammal at least one compound in a dosage and amount effective to treat the dysfunction in the mammal, the composition having a structure represented by the following formula:

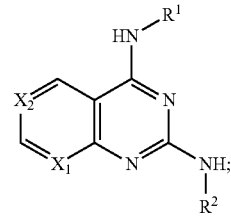

wherein

X$_1$ is selected from C$_{1-6}$—R$^A$;

X$_2$ is selected from C$_{1-6}$—R$^B$;

R$^A$ is optionally substituted with one or more Z, and selected from H, alkyl, alkyl-amino, amino, amine, cyano, —OH, alkyl-OH, N—(CH$_2$)$_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; with a drug known to treat cancer.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein the term "modulate" can refer to enhancement of activity or inhibition of activity.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by a modulation of Ras signaling" means having been subjected to a physical examination by a person of skill, for example, a physician, and found to have a condition that can be diagnosed or treated by a compound or composition that can modulate Ras signaling. Such a diagnosis can be in reference to a disorder, such as cancer, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "cancer" refers to disorders characterized by cellular proliferation, evasion of programmed cell death, altered cellular metabolism, induction of angiogenesis, enhancement of cellular invasion and metastasis, alterations to tumor suppressor genes causing a reduction in activity, alterations to oncogenes casing enhancement of activity, or evasion of immunological destruction. Cancer can refer to a tissue or organ type and can also spread from one tissue or organ to another tissue type or organ. Cancer can occur in any cell of any type including but not limited to breast, prostate, skin, lung, pancreatic, stomach, brain, kidney, uterine, ovarian, testicular, endothelial, colon, bladder, bone as well as cells of the blood to produce various forms of leukemia.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents. Unless otherwise specified, the substituents are all independent from one another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, thioether, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "heterocycle," as used herein refers to single and multi-cyclic aromatic or non-aromatic ring systems in which at least one of the ring members is other than carbon. Heterocycle includes pyridinde, pyrimidine, pyrazine, furan, thiophene, pyrrole, isoxazole, isothiazole, pyrazole, oxazole, thiazole, imidazole, oxazole, oxadiazole including, for example, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, imidazothiadiazole, imidazooxadiazole, imidazothiazole, thiazolotriazole, and the like.

The term "hydroxyl" as used herein is represented by a formula —OH.

The term "thiol" as used herein is represented by a formula —SH.

The term "thioester" as used herein is represented by a formula —S—CO.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

In some aspects, a structure of a compound can be represented by a formula:

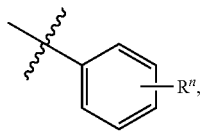

which is understood to be equivalent to a formula:

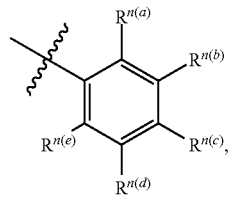

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful as modulators of Ras signaling. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect the invention relates to compounds having a structure represented by formula:

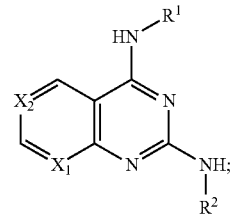

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkylalkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; provided that when $X^1$ is C—H, $X^2$ is CH, and $R^1$ is furan, $R^2$ is not phenyl and where $X^1$ is C—H, $X^2$ is CH, and $R^1$ is benzyl, $R^2$ is not phenyl.

In another aspect of the invention, $R^A$ is $C_1$-$C_6$ alkylamino, piperazinyl, pyridinyl, $C_1$-$C_6$ alkylalcohol, cycloamino, cycloalkylamino, or cycloalkenylamino; $R^1$ is —$(CH_m)_n$-cycloalkyl, —$(CH_m)_n$-heterocycloalkenyl, —$(CH_m)_n$-heteroaryl, or —$(CH_m)_n$-alkyl and optionally substituted with cycloalkyl, methyl, or ethyl. In another aspect, $R^2$ is selected from —$(CH_2)_n$-cycloalkyl, —$(CH_2)_n$-alkenyl, or $(CH_2)_n$-aryl, and optionally independently substituted with alkyl, cycloalkyl, $CF_3$, one or more halogen such as Cl, F, Br; methyl, or cyano; m is 1 or 2; n is 0-3; $R^A$ is selected from aminoalkyl, aminocyloalkyl, aminocycloalkenyl, cycloalkyl, cycloalkenyl, pyridinyl, pyrrolyl, cyano, acetimidamidyl, piperazinyl, and optionally substituted with OH; $X_2$ is selected from H or ethylaminyl.

In another aspect of the invention, $R^1$ is optionally substituted and selected from:

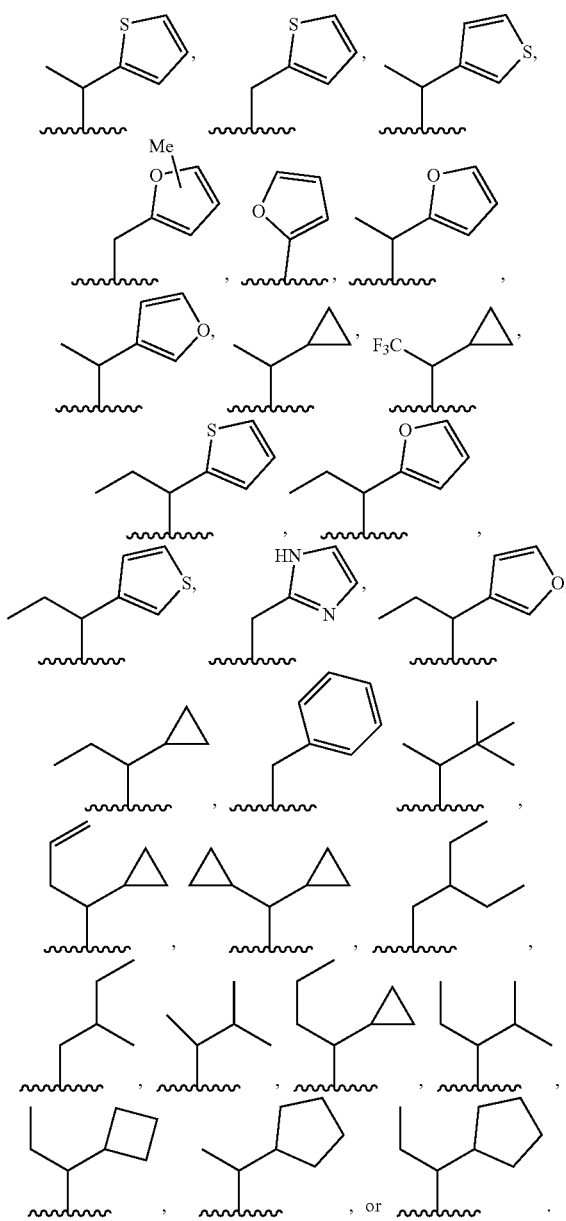

In another aspect of the invention, $R^2$ is optionally substituted and selected from

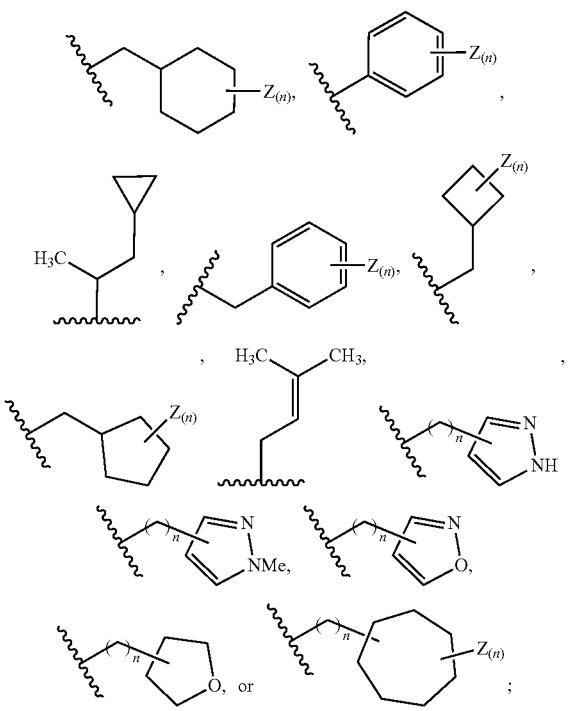

Z is independently H, Cl, F, Br, cyano, $CF_3$, methoxy, or alkyl, including methyl, ethyl, vinyl, cyclopropyl; or more than one Z joins together to form a 5 or six membered ring;

n is 0-3;

or a pharmaceutically acceptable salt thereof or a pharmaceutically acceptable derivative thereof.

Another aspect of the invention is a compound disclosed herein wherein $R^2$ and more than one Z together form:

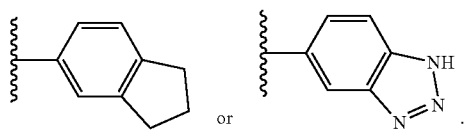 [SMILES: *c1ccc2c(c1)CCC2 ; *c1ccc2[nH]nnc2c1]

Another aspect of the invention is a compound disclosed herein wherein $X_1$ is C—$R^A$ and $R^A$ is selected from:

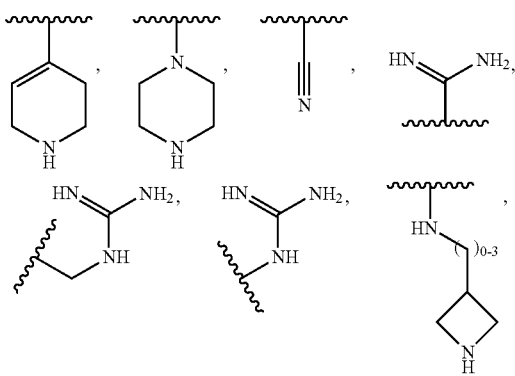

-continued

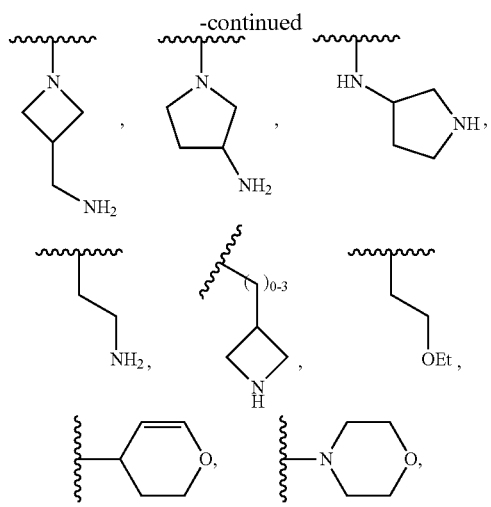

—NH$_2$, -alkylNH$_2$, -alkyl-NH-alkyl, —NHMe, —NMe$_2$, —OH, —NH-alkyl-NH$_2$, —NH-alkyl-NHMe, —NH—alkyl-NMe$_2$, —NH-alkyl-OH, halogen, CN, H;

or a pharmaceutically acceptable salt thereof or a pharmaceutically acceptable derivative thereof.

Another aspect of the invention is a compound disclosed herein wherein R$^4$ is amino. Other aspects are where R$^4$ is one of:

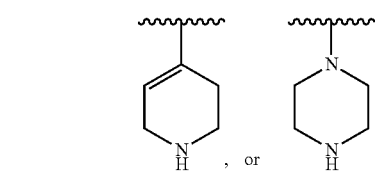

Another aspect of the invention is a compound disclosed herein wherein R$^1$ is

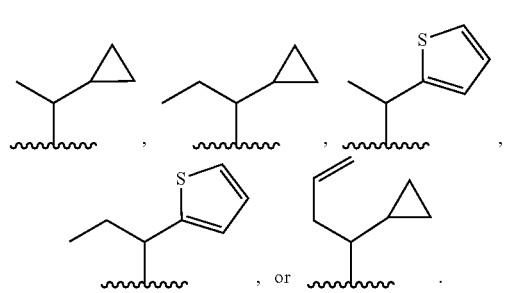

Another aspect of the invention is a compound disclosed herein wherein R$^2$ is

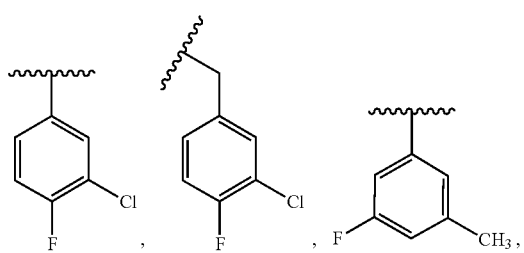

-continued

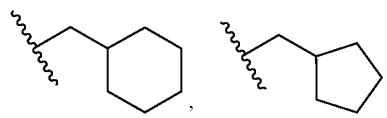

Examples of embodiments of the present invention include the following compounds and their pharmaceutically acceptable salts:

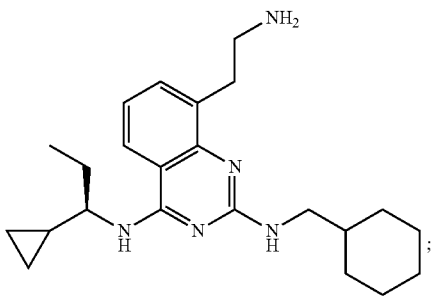

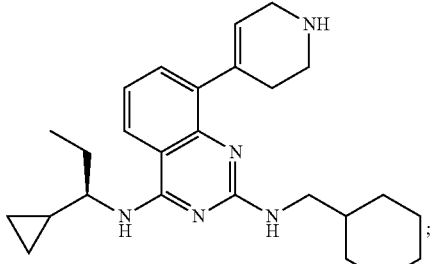

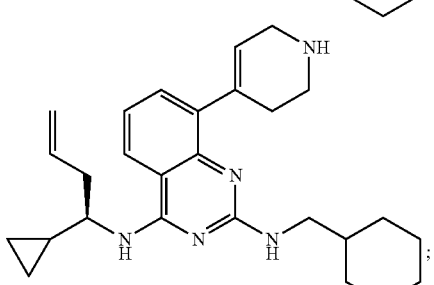

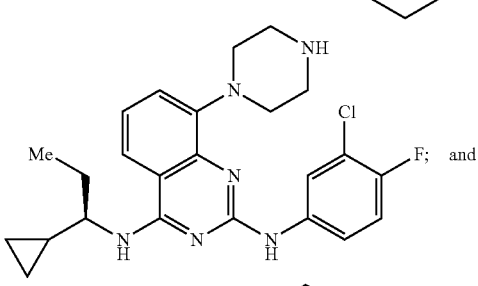

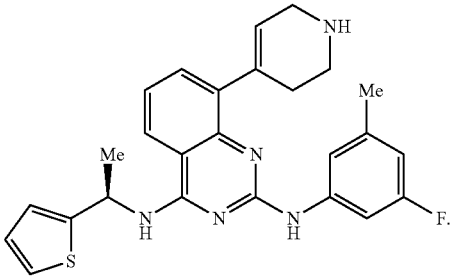

Examples of embodiments of the present invention also include the following compounds and their pharmaceutically acceptable salts:
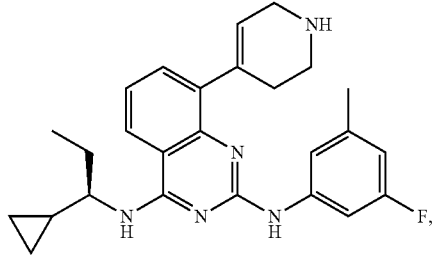
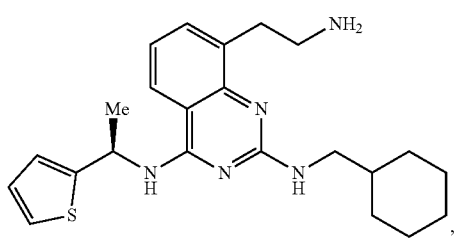
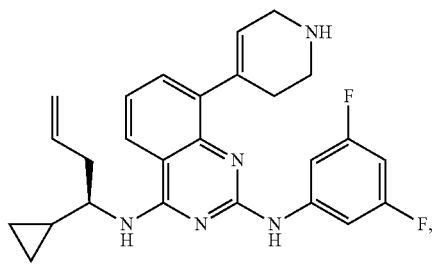
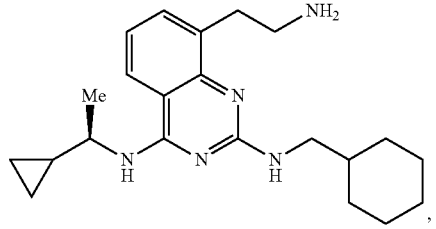
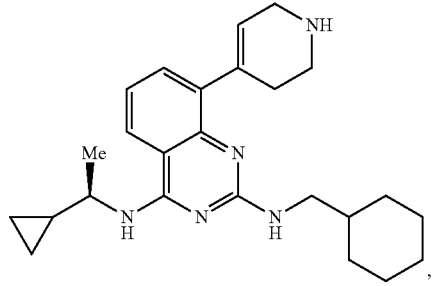
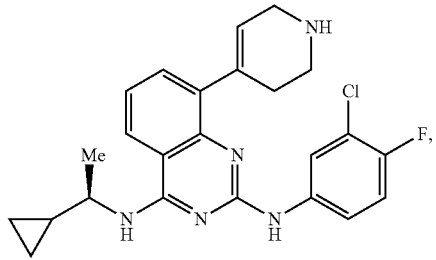
-continued
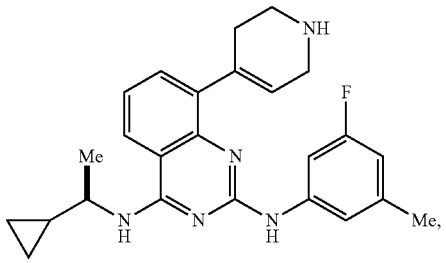
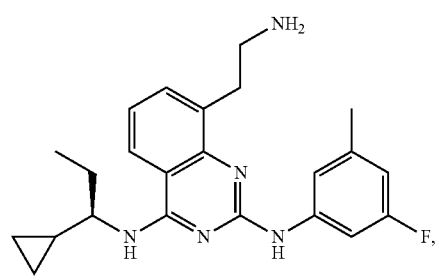
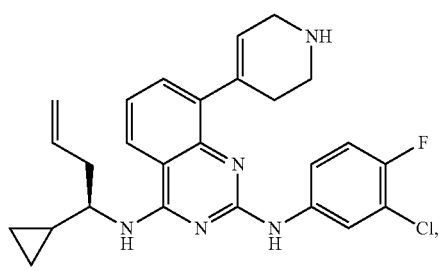
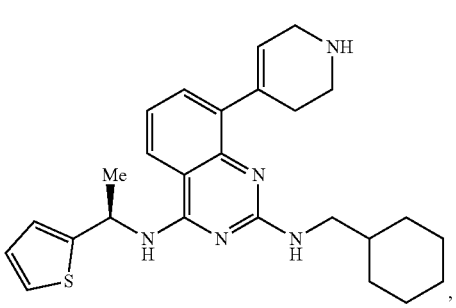
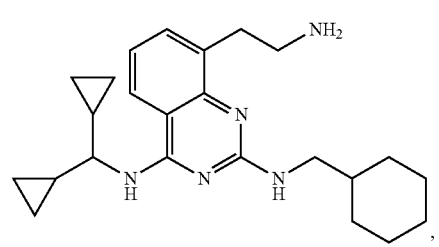
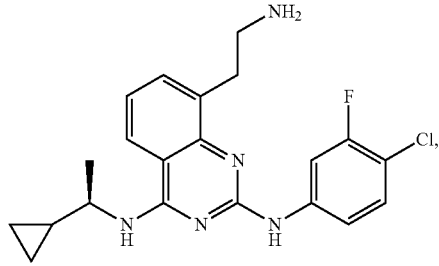

-continued
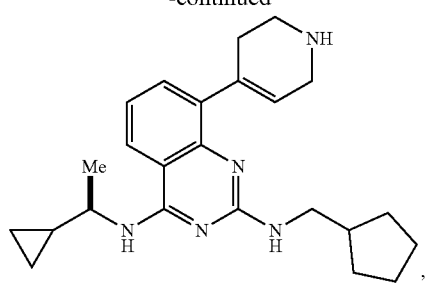
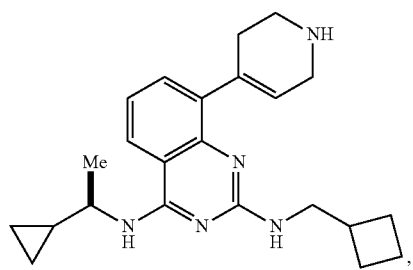
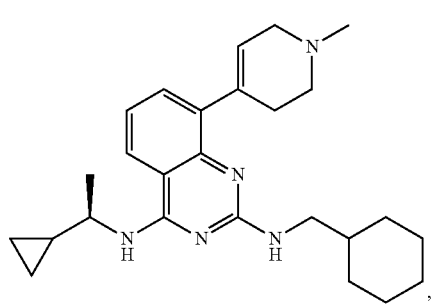
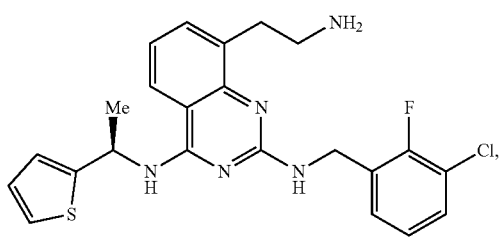
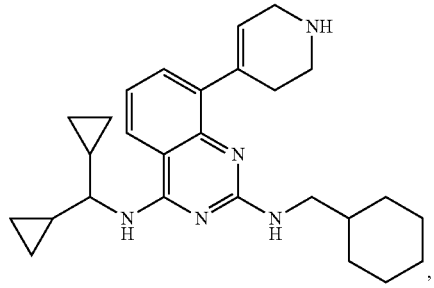
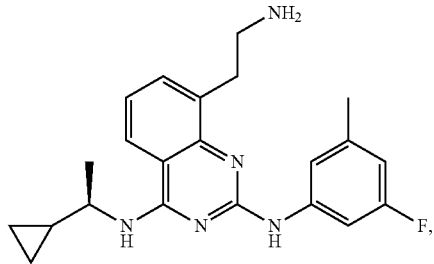
-continued
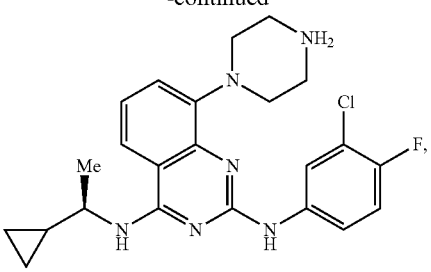
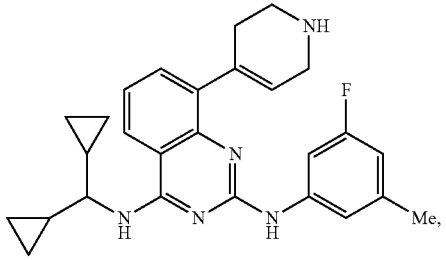
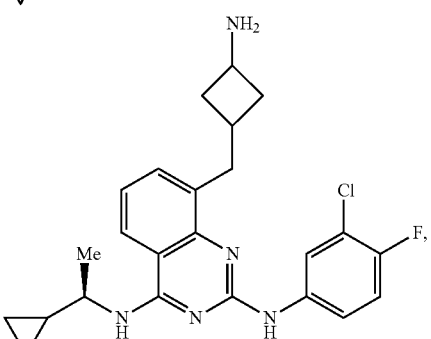
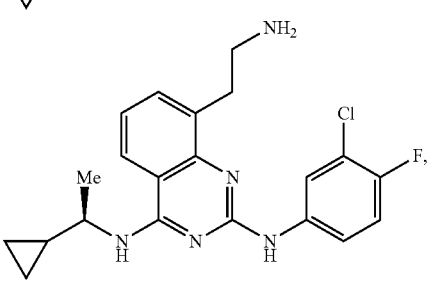
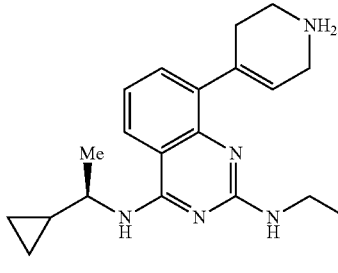
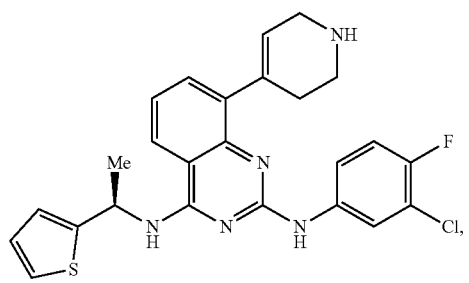

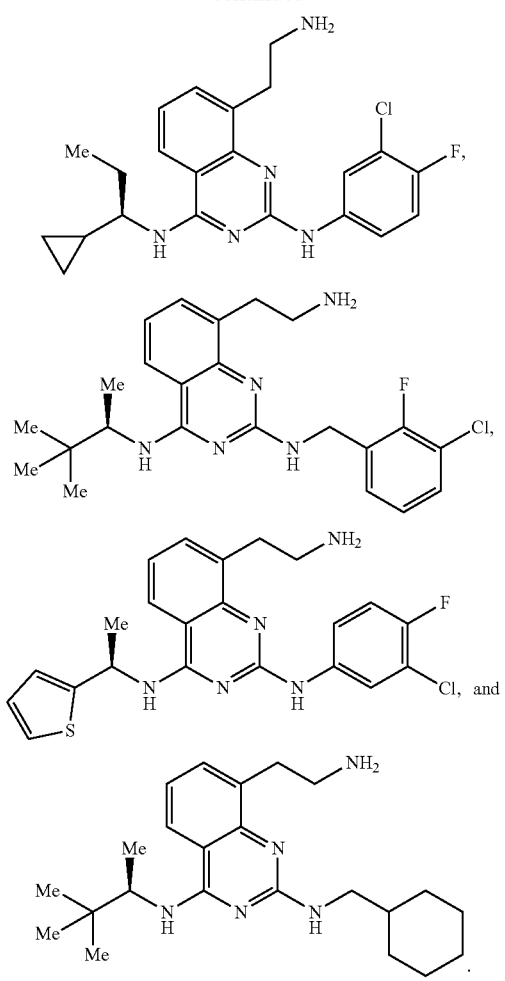
Examples of embodiments of the present invention also include the following compounds and their pharmaceutically acceptable salts:
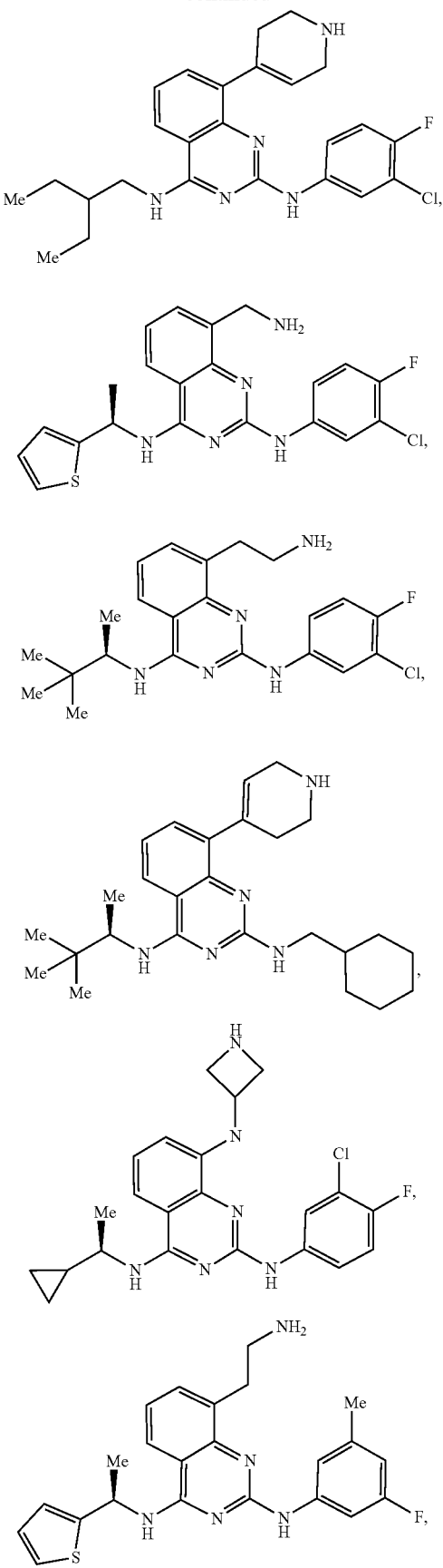

-continued
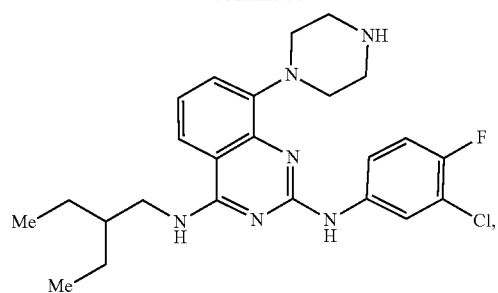
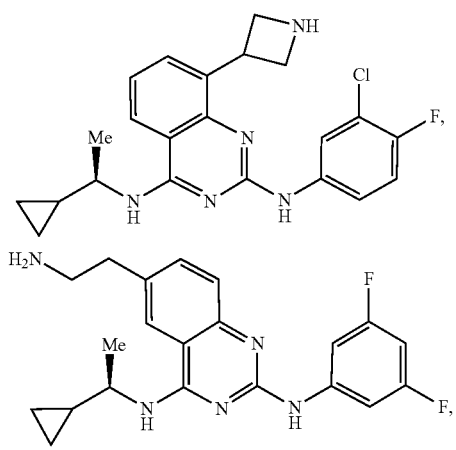
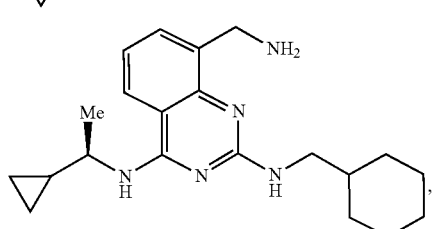
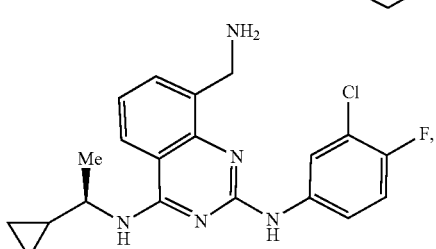
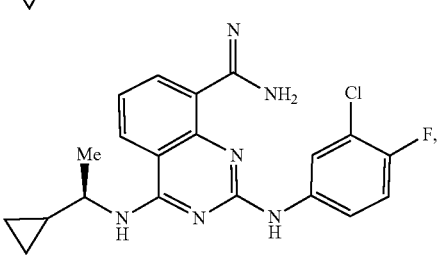
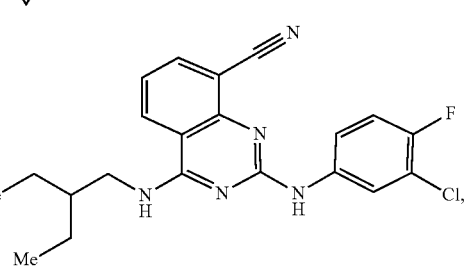
-continued
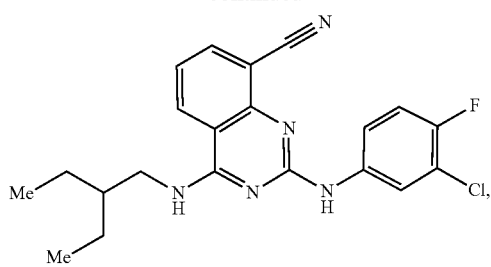
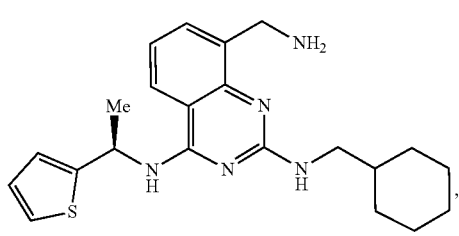
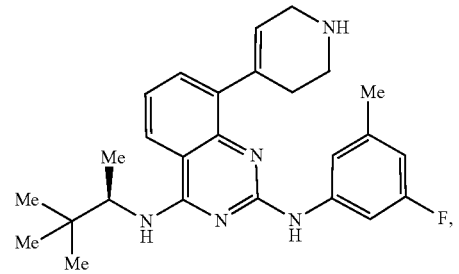
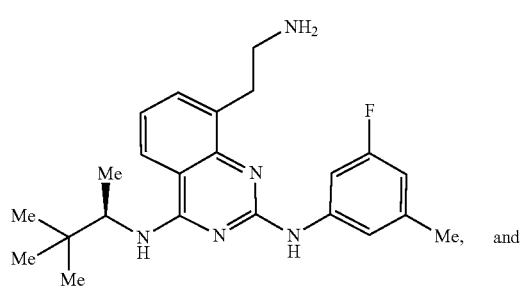
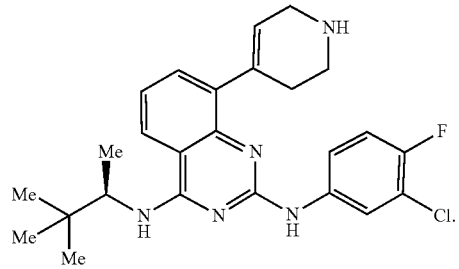
Examples of embodiments of the present invention also include the following compounds and their pharmaceutically acceptable salts:

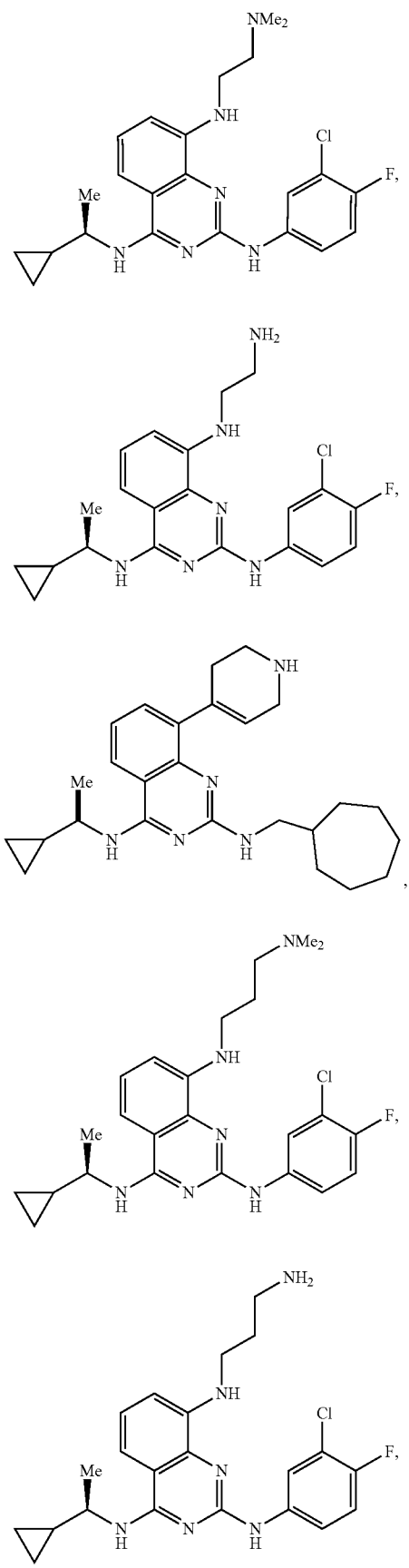 [SMILES: C[C@@H](Nc1nc(Nc2ccc(F)c(Cl)c2)nc2c(NCCN(C)C)cccc12)C1CC1 ; C[C@@H](Nc1nc(Nc2ccc(F)c(Cl)c2)nc2c(NCCN)cccc12)C1CC1 ; C[C@@H](Nc1nc(NCC2CCCCCC2)nc2c(C3=CCNCC3)cccc12)C1CC1 ; C[C@@H](Nc1nc(Nc2ccc(F)c(Cl)c2)nc2c(NCCCN(C)C)cccc12)C1CC1 ; C[C@@H](Nc1nc(Nc2ccc(F)c(Cl)c2)nc2c(NCCCN)cccc12)C1CC1]
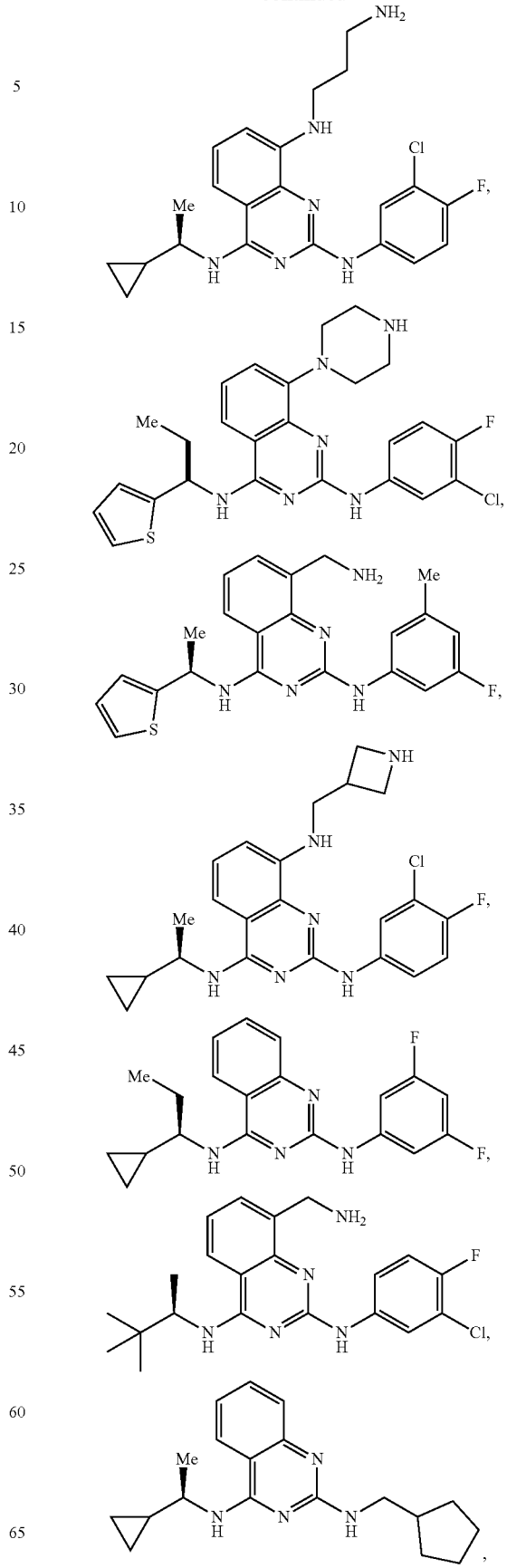

33
-continued
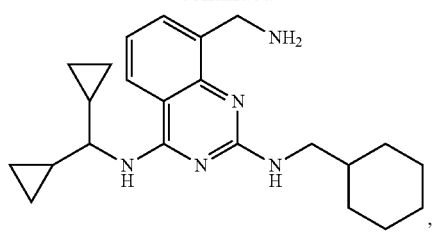
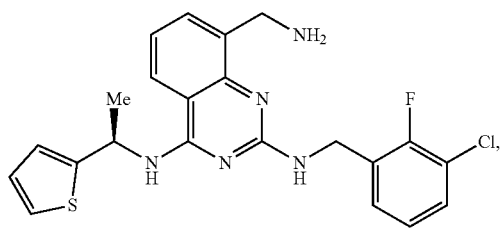
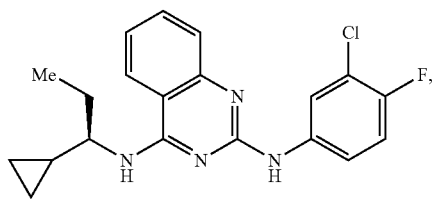
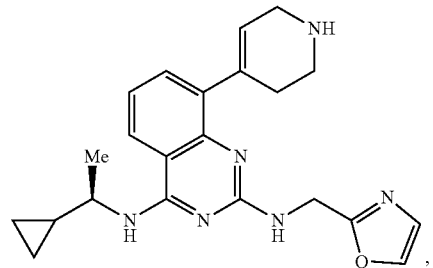
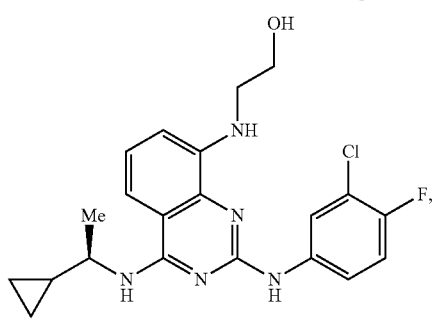
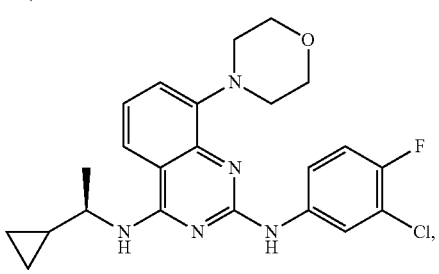
34
-continued
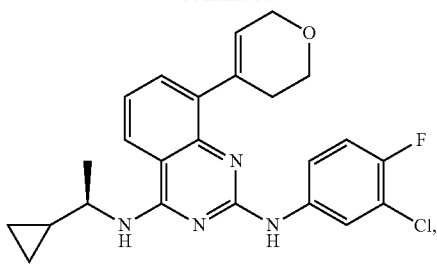
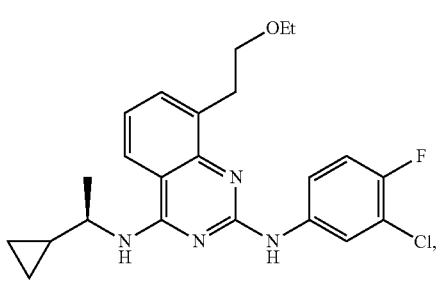
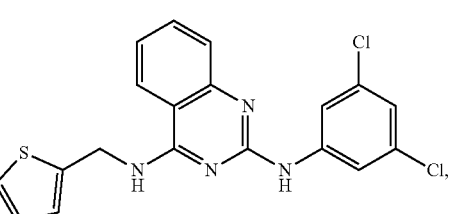
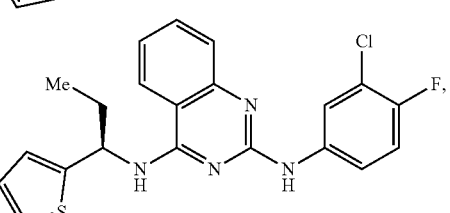
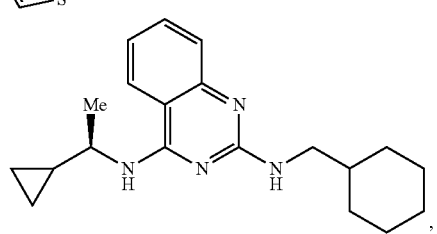
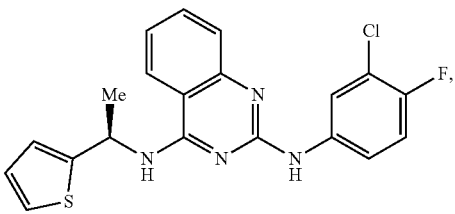
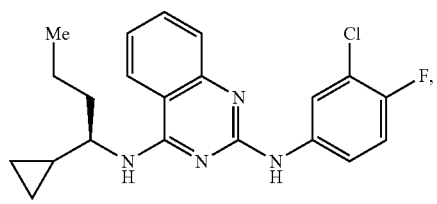

35
-continued
36
-continued
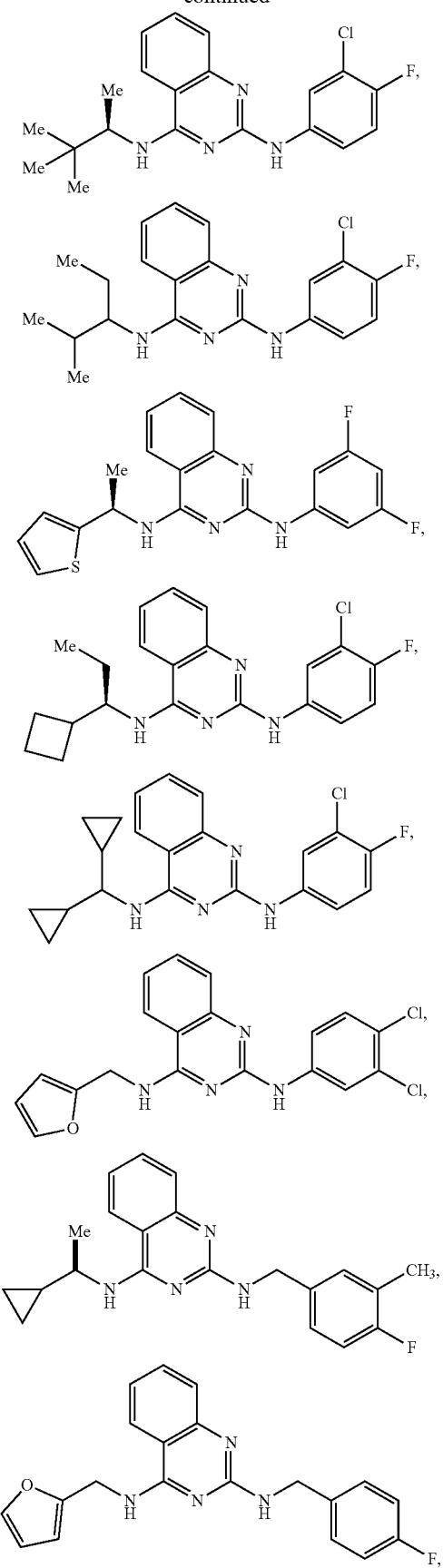
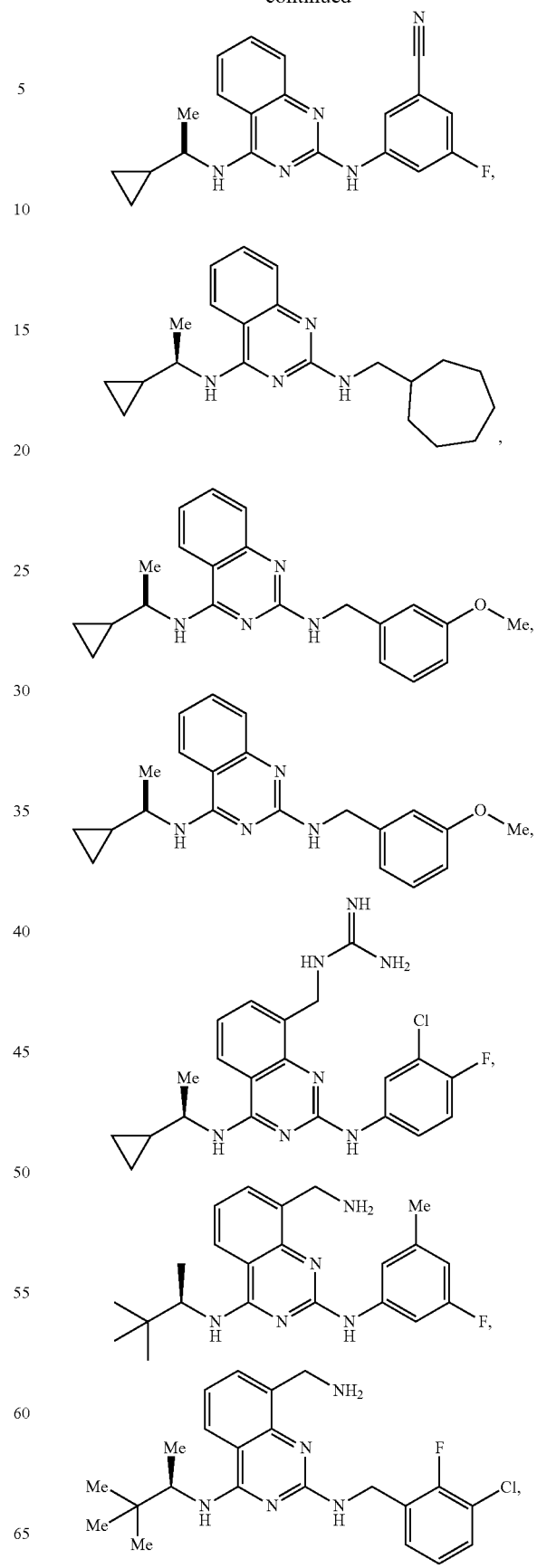

37
-continued
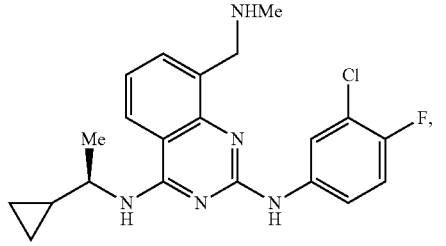
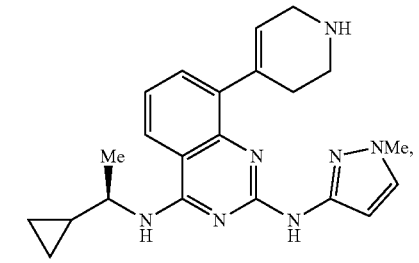
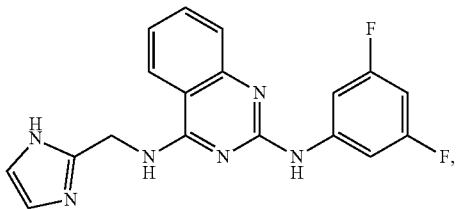
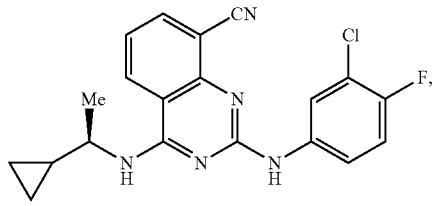
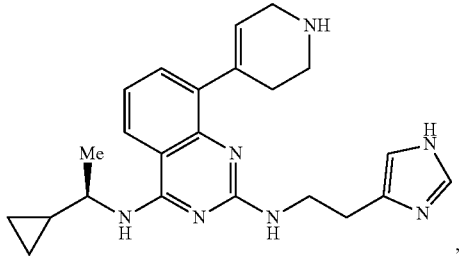
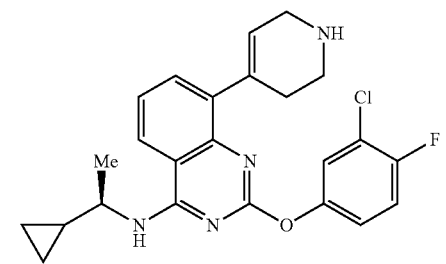
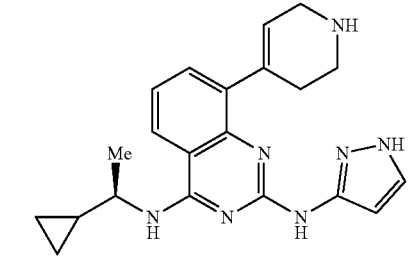
38
-continued
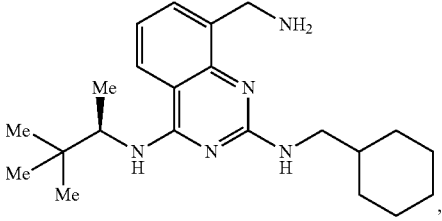
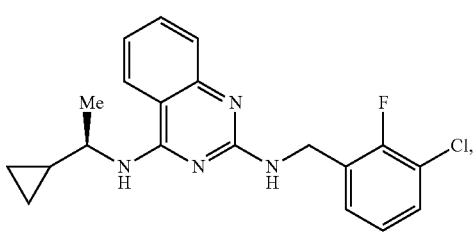
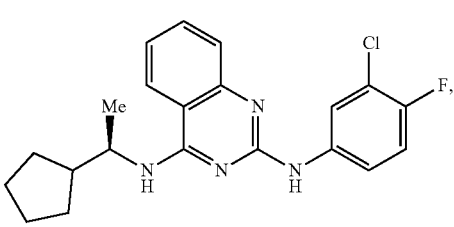
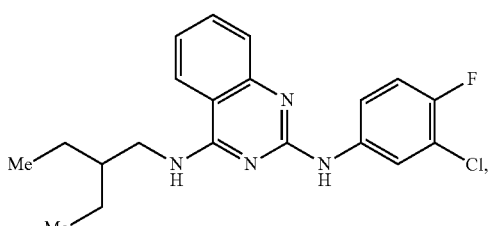
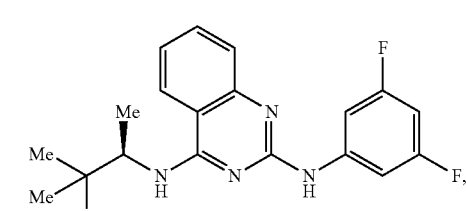
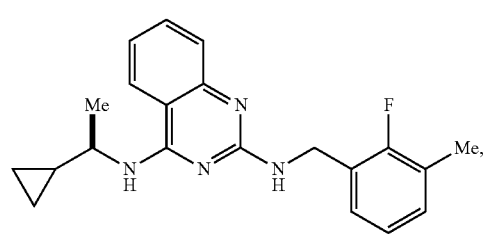
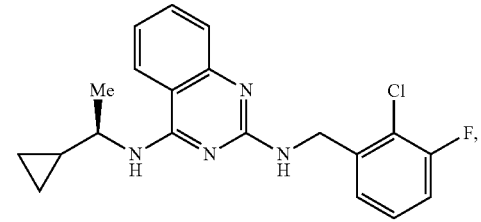

39
-continued
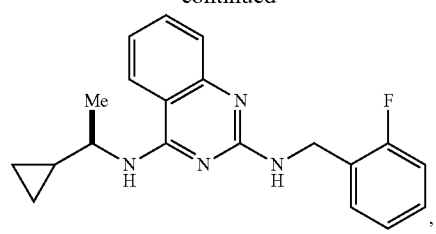
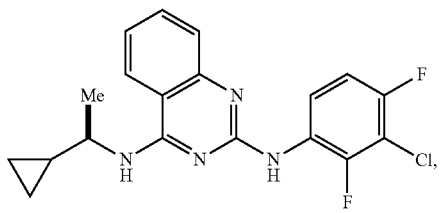
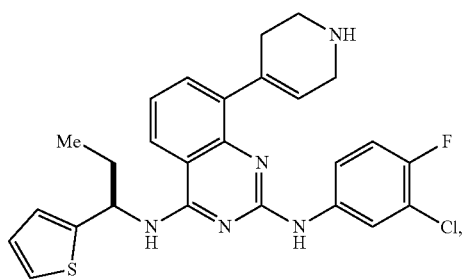
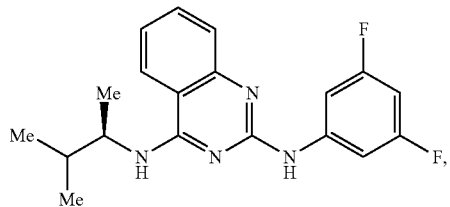
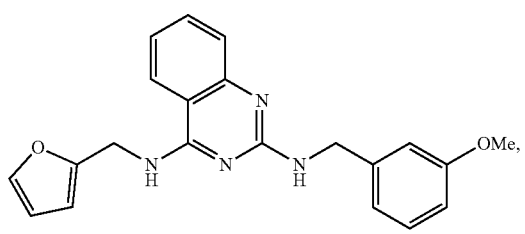
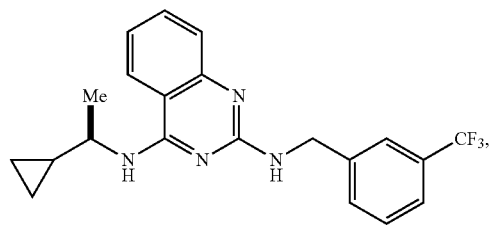
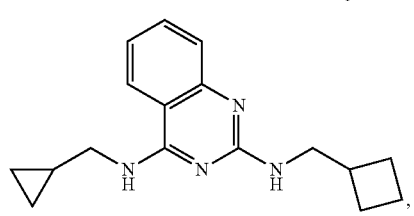
40
-continued
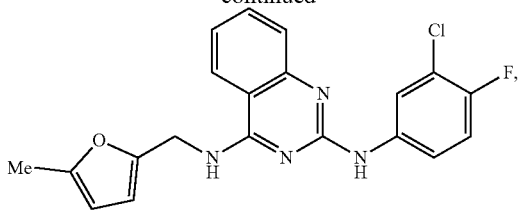
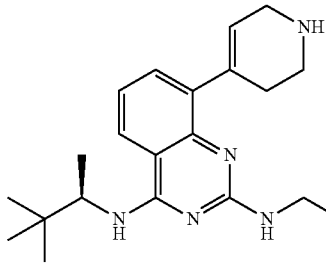
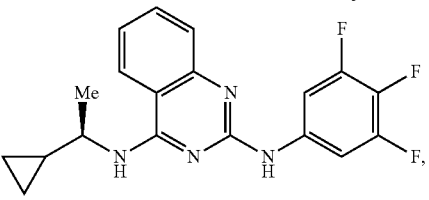
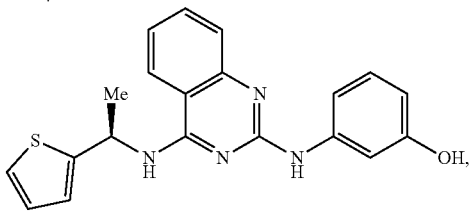
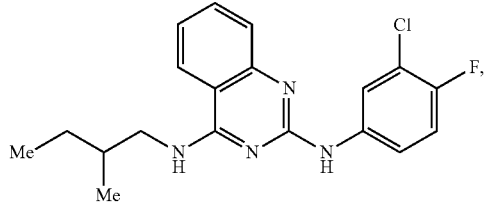
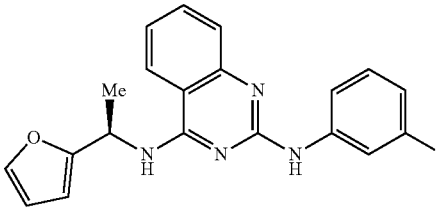
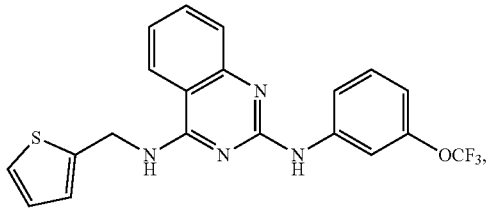
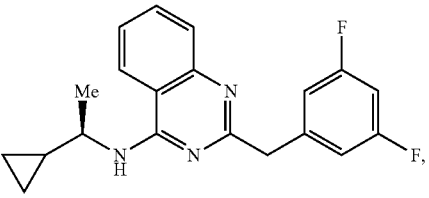

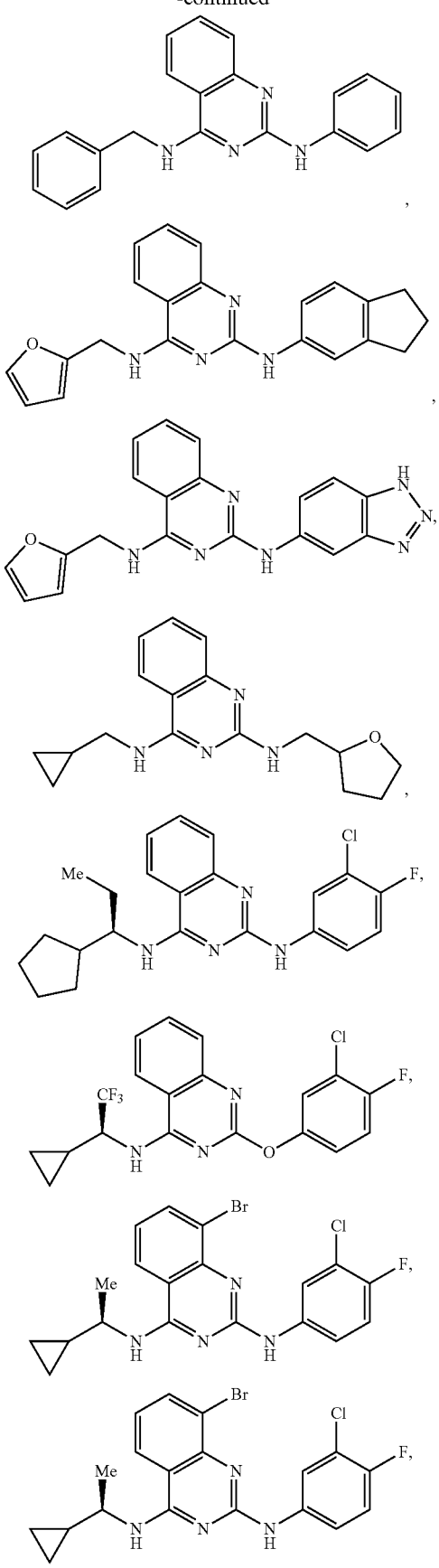

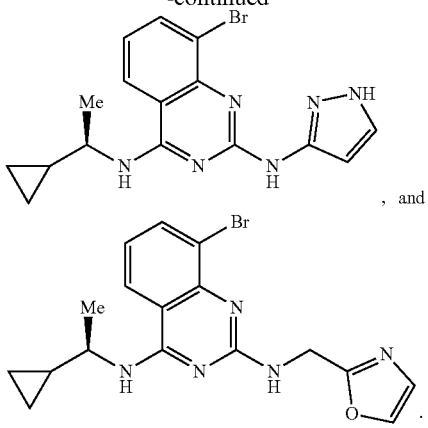

Another embodiment of the present invention is a compound of the following formula:

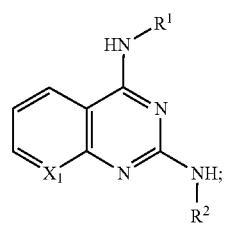

wherein
X₁ is selected from $C_{1-6}$—$R^4$;
$R^4$ is selected from

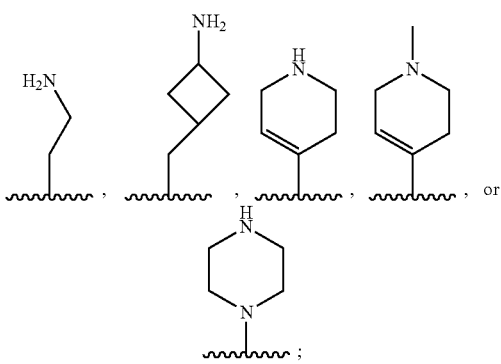

$R^1$ is optionally substituted with one or more Z and selected from alkyl-cycloalkyl, alkenyl-cycloalkyl, or alkyl-thiophene;
$R^2$ is optionally substituted with one or more Z, and selected from phenyl, benzyl, alkyl-cycloalkyl;
Z is independently H, alkyl, halogen;
or a pharmaceutically acceptable salt thereof or a pharmaceutically acceptable derivative thereof.

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed modulators of Ras signaling and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations, the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be co-administered, either in concomitant therapy or in a fixed combination.

In one aspect, the compound can be employed in combination with at least one additional therapeutic agent. In one aspect of the invention the at least one additional therapeutic agent may be a cancer chemotherapeutic agent. In one aspect, the chemotherapeutic agent(s) may be platinum compounds, topoisomerase inhibitors, peptide antibiotics, alkylators, anthrcyclines, taxenes, histone deacetylase inhibitors, epothilones, kinase inhibitors, nucleotide analogues, retinoids, vinca alkaloids and derivatives, or any combination of chemotherapeutics. The platinum compound(s) may be carboplatin, cisplatin, or oxaliplatin. The topoisomerase inhibitor(s) may be irinotecan, topotecan, etoposide, teniposide, or tafluposide. The peptide antibiotic(s) may be bleomycin or actinomycin. The alkylator(s) may be cyclophosphamide, mechlorethamine, chlorambucil, or melphalan. The anthracycline(s) may be daunorubicin, doxorubicin, epirubicin, mitoxntrone, or valirubicin. The taxene(s) may be paclitaxel or docetaxel. The histone deacetylase inhibitor(s) may be vorinostat or romidepsin. The epothilone(s) may be ixabepilone, patupilone, or sagopilone. The kinase inhibitor(s) may be bortezomib, dabrafenib, erlotinib, gefitinib, imatinib, tremetinib, vemurafenib, or vismodegib. The nucleotide analogue(s) may be azacitidine, azathioprine, capecitabine, cytarabine, flurouracil, gemcitabine, hydroxyurea, mercaptopurine, methotrexate, or tioguanine.

In one aspect, the invention relates to pharmaceutical compositions comprising a compound having a structure represented by a formula:

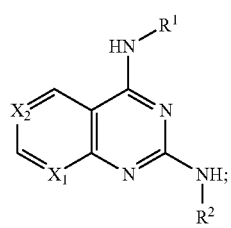

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; provided that when $X^1$ is C—H, $X^2$ is CH, and $R^1$ is furan, $R^2$ is not phenyl and where $X^1$ is C—H, $X^2$ is CH, and $R^1$ is benzyl, $R^2$ is not phenyl.

In another aspect, the invention relates to pharmaceutical compositions comprising a compound having a structure represented by a formula:

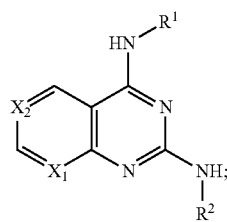

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; provided that when $X^1$ is C—H, $X^2$ is CH, and $R^1$ is furan, $R^2$ is not phenyl and where $X^1$ is C—H, $X^2$ is CH, and $R^1$ is benzyl, $R^2$ is not phenyl.

In another aspect, the invention relates to pharmaceutical compositions comprising a compound having a structure represented by a formula:

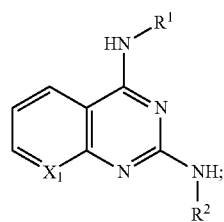

wherein $X_1$ is selected from $C_{1-6}$—$R^A$;

$R^A$ is selected from

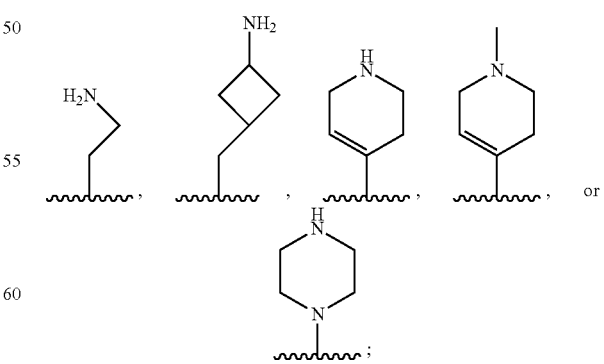

$R^1$ is optionally substituted with one or more Z and selected from alkyl-cycloalkyl, alkenyl-cycloalkyl, or alkyl-thiophene;

$R^2$ is optionally substituted with one or more Z, and selected from phenyl, benzyl, alkyl-cycloalkyl;

Z is independently H, alkyl, halogen;

or a pharmaceutically acceptable salt thereof or a pharmaceutically acceptable derivative thereof.

Uses of Compounds

In some embodiments, the present invention provides methods for the treatment of a cancer or the primary or secondary prophylaxis of cancer, which includes the steps of administering to a patient (for example, a human) in need thereof a therapeutically effective amount of a compound of Formula I or stereoisomers, tautomers, pharmaceutically acceptable salts, prodrug esters, or solvates thereof.

Cancer may be selected from the group consisting of pancreatic ductal carcinoma, colorectal adenocarcinoma, multiple myeloma, lung adenocarcinoma, skin cutaneous melanoma, uterinecorpus endometrial carcinoma, uterine carcinosarcoma, thyroid carcinoma, acute myeloid leukemia, bladder urothelial carcinoma, gastric adrenocarcinoma, cervical adrenocarcinoma, head and neck squamous cell carcinoma, diffuse large B cell lymphoma, oesophageal adenocarcinoma, adenoid cystic carcinoma, chromophobe renal cell carcinoma, hepatocellular carcinoma, breast invasive carcinoma, cervical squamous cell carcinoma, ovarian seros adenocarcinoma, adrenocortical carcinoma, prostate adenocarcinoma, neuroblastoma, brain lower grade glioma, glioblastoma, medulloblastoma and kidney renal clear cell carcinoma as well as others as referenced in the literature. (Pylayeva-Gupta et al. RAS oncogenes: weaving a tumorigenic web. *Nature Rev. Cancer.* 11 761-773 (2011); Cox et al. Drugging the undruggable RAS: Mission possible? *Nature Rev. Drug Discovery.* 13 828-851(2014)).

In some embodiments, the present invention includes a method of inhibiting or preventing cellular proliferation and transformation which includes the step of administering to a subject (such as a human) in need thereof a therapeutically effective amount of a modulator of Ras signaling, which is a compound of Formula I.

In some embodiments, the invention provides a method of treatment or prophylaxis of cancer involving administering to a subject in need thereof (e.g., a human) a therapeutically effective amount of a compound that binds to SOS (such as a compound of Formula I of the invention) and increases the rate of nucleotide exchange of Ras or modulates Ras signaling.

In some embodiments, the present invention provides a compound of the present invention or stereoisomers, tautomers, pharmaceutically acceptable salts, solvates, or prodrug esters thereof, for use in therapy for the treatment or prophylaxis of cancer.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of cancer.

In some embodiments, compounds of the present invention may be co-administered with at least one additional drug or therapeutic agent. In certain embodiments of the present invention, at least one additional therapeutic agent(s) are cancer chemotherapeutics or a combination thereof. Examples of chemotherapeutic agents include platinum compounds, topoisomerase inhibitors, peptide antibiotics, alkylators, anthrcyclines, taxenes, histone deacetylase inhibitors, epothilones, kinase inhibitors, nucleotide analogues, retinoids, or vinca alkaloids and derivatives.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

In one aspect, the invention relates to uses of a compound for modulating Ras signaling in a mammal, wherein the compound has a structure represented by the following formula:

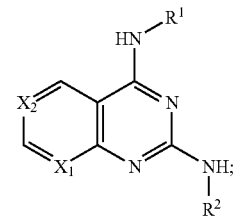

wherein $X_1$ is selected from $C_{1-6}$—$R^A$;

$X_2$ is selected from $C_{1-6}$—$R^B$;

$R^A$ is optionally substituted with one or more Z, and selected from H, alkyl, alkyl-amino, amino, amine, cyano, —OH, alkyl-OH, N—$(CH_2)_{1-6}$—OH, acetamidine, guanidine, N-containing cycloheteroalkyl, N-containing heteroaryl, amino-substituted cycloalkyl, amino-substituted heterocycloalkyl, amino-substituted aryl, halogen, cycloalkyl, heterocycloalkyl, heteroalkenyl, aminocycloalkyl, aminocycloalkenyl;

$R^B$ is optionally substituted with one or more Z and selected from H, alkyl, aminoalkyl, cycloalkyl, alkoxy, halogen, cycloheteroalkyl, aryl, heteroaryl, $R^1$ is optionally substituted with one or more Z and selected from alkyl, benzyl, phenyl, cycloalkyl, aryl, heteroaryl, heterocycloalkyl, alkyl-cycloalkyl, alkyl-aryl, alkyl-heteroaryl, alkenyl-cycloalkyl;

$R^2$ is optionally substituted with one or more Z, and selected from phenyl, benzyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof.

The disclosed uses for modulating Ras signaling in a mammal can further be directed for use in treating one or more disorders, for example cancer, and other disease states associated with Ras dysfunction (e.g., Ras-associated autoimmune leukoproliferative disorder, or certain types of mitochondrial dysfunction) in a subject, for example a mammal or a human.

EXPERIMENTAL/EXAMPLES

The following examples are present to provide those of ordinary skill in the art with a more complete disclosure and description of how compounds of the present invention are made and used and are intended to be purely exemplary of the present invention and are not intended to limit the scope of what the inventors regard as their invention.

General: All nonaqueous reactions were performed in flame dried or oven dried round-bottom flasks under an atmosphere of argon. Plastic syringes were used to transfer air and moisture sensitive liquids. Reaction temperatures were controlled using a thermocouple thermometer and analog hotplate stirrer. Reactions were conducted at room temperature (rt, approximately 23° C.) unless otherwise noted. Analytical thin layer chromatography (TLC) was performed on E. Merck silica gel 60 F254 plates and visualized first by UV and then by staining with either ceric ammonium molybdate, 2,4-dinitrophenylhydrazine, iodine, phosphomolybdic acid, potassium permanganate, or anisaldehyde. Yields are reported for isolated, spectroscopically pure compounds.

Instrumentation: HPLC purification was conducted on a Gilson HPLC system using a Gemini-NX C18 column. $^1$H NMR spectra were recorded on Bruker 400 MHz spectrometers. For $^1$H NMR spectra, chemical shifts are reported relative to residual CHCl$_3$ (δ 7.26 ppm). For $^{13}$C NMR spectra, chemical shifts are reported relative to residual CHCl$_3$ (δ 77.00 ppm). Coupling constants are reported in Hz. Data for $^1$H NMR spectra are reported as follows: chemical shift (δ ppm), multiplicity (s=singlet, d=doublet, t=triplet, dd=double of doublets, dt=doublet of triplets, q=quartet, quint=quintet, sext=sextet, sept=septet, m=multiplet, br=broad, ovlp=overlapping resonances, app=apparent), coupling constants (Hz), and integration. LCMS was conducted and recorded on an Agilent Technologies 6140 Quadrupole instrument. Microwave reactions were conducted in a Biotage Initiator 2.0 microwave reactor.

General Procedure A for the Preparation of 2,4-Diaminoquinazoline Analogs

The quinazoline analogs 1-46 were prepared by the procedure outlined in Scheme 1. Variants of this procedure are exemplified by Examples 1 and 46 (steps C and D).

Scheme 1: Diaminoquinazoline preparation.

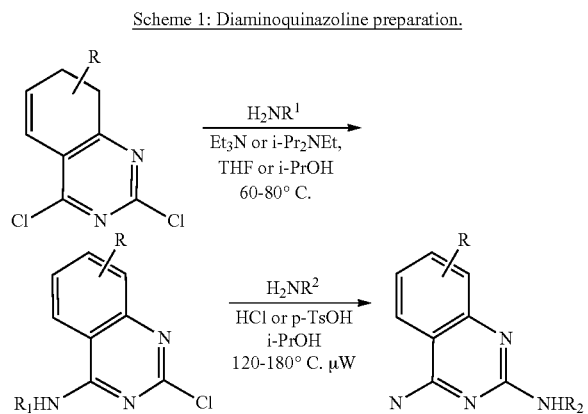

General Procedure B for α-Branched Amine Hydrochloride Preparation

The chiral branched amines were either commercially available, or were prepared according to the procedure described in Scheme 2. This procedure is exemplified by Example 34, Steps A-C.

Scheme 2: Synthesis of chiral amines.

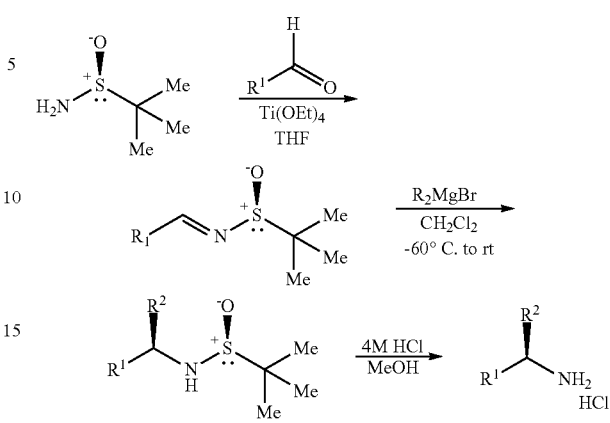

Step A: According to Liu et al. (*J. Org. Chem.* 1999, 64, 1278-1284), a 0.5 M solution of Ti(OEt)$_4$ (technical grade, □20% Ti; □2 eq.) and aldehyde (1.1 eq.) in THF was prepared. Then, (S)-2-methylpropane-2-sulfinamide (1 eq.) was added and the mixture was stirred at room temperature. Conversion was followed by TLC (reaction time ~4-16 h). Upon reaction completion, the mixture was poured into an equal volume of brine with rapid stirring. The resulting suspension was filtered through a plug of Celite, and the filter cake was washed with CH$_2$Cl$_2$. The organic layer was washed with brine. The brine layer was extracted once with a small volume of CH$_2$Cl$_2$, and the combined organic portions were dried over MgSO$_4$, filtered, and concentrated. The resulting sulfinyl aldimines were purified by silica gel chromatography (eluting with CH$_2$Cl$_2$).

Step B: According to Cogan et al. (*Tetrahedron* 1999, 55, 8883-8904), to a solution of the (S)-sulfinyl aldimine—prepared by a procedure analogous to Step A—in CH$_2$Cl$_2$ at −61° C. was added the selected Grignard reagent, via dropwise addition. The mixture was stirred at −61° C. for 2 h and then allowed to warm to room temperature overnight with stirring. When complete, the reaction mixture was quenched by the addition of saturated aqueous NH$_4$Cl and the aqueous layer was extracted with CH$_2$Cl$_2$. The combined organic layers were dried over MgSO$_4$, filtered, and concentrated. The sulfinamide diastereomers were separated by silica gel chromatography (0-3% MeOH in CH$_2$Cl$_2$) to provide the desired sulfinamides.

Step C: To the sulfinamide—prepared by a procedure analogous to Step B—was added 1:1 (v/v) MeOH and HCl in dioxane solution (4.0 M, 2.0 eq.). The mixture was stirred at room temperature for 30 min and was then concentrated to near dryness. Diethyl ether was added to precipitate the amine hydrochloride. The precipitate was then filtered and washed with a 1:1 (v/v) mixture of diethyl ether and hexanes to provide the requisite amine as its hydrochloride salt.

General Procedure C for Preparation of 2-oxo-4-amino-8-bromoquinazolines

The quinazoline analog 47 was prepared by the procedure outlined in Scheme 3. This procedure is exemplified by Example 47.

Scheme 3: Preparation of 2-oxo-4-amino-8-bromoquinazolines.

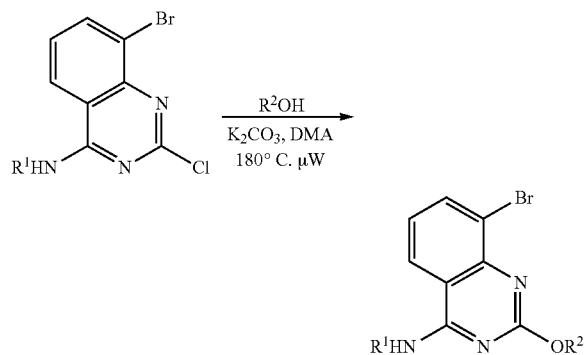

General Procedure D for 8-bromo-2,4-diaminoquinazoline Preparation

The quinazoline analog 48 was prepared by the procedure outlined in Scheme 4. This procedure is exemplified by Example 48.

Scheme 4: 8-bromo-2,4-diaminoquinazoline preparation.

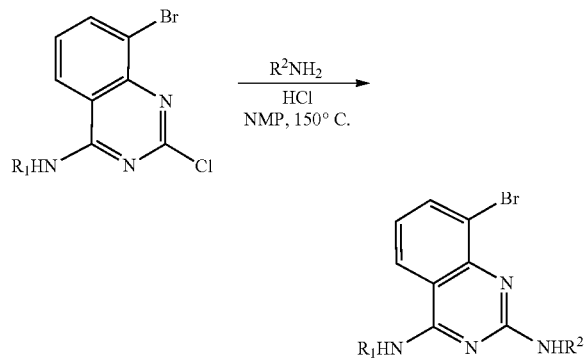

General Procedure E for Suzuki Couplings with Organotrifluoroborate Salts

The quinazoline analogs 50, 60-61, 74, 77, 82-85, 91-94, and 109 were prepared by the procedure outlined in Scheme 5. This procedure is exemplified by Example 50.

Scheme 5: Suzuki couplings with organotrifluoroborate salts.

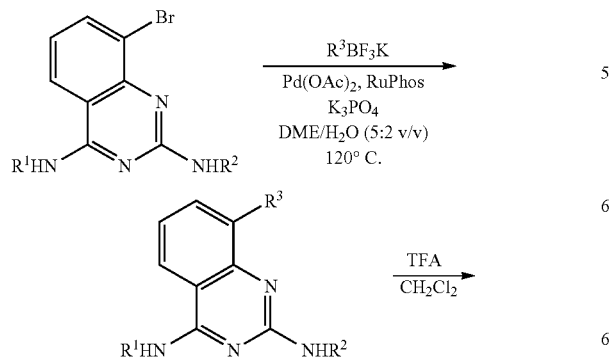

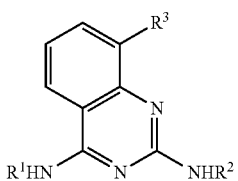

General Procedure F for Suzuki Couplings with Boronate Esters

The quinazoline analogs 51, 62-63, 69-76, 79-81, 88-90, 98, 100, and 102-108 were prepared by the procedure outlined in Scheme 6. This procedure is exemplified by Example 51.

Scheme 6: Suzuki couplings with boronate esters.

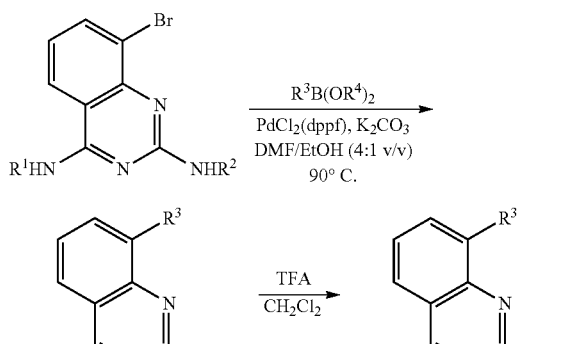

General Procedure G for Buchwald-Hartwig Cross-Couplings with Boc-Protected Amines The quinazoline analogs 52 and 64 were prepared by the procedure outlined in Scheme 7. This procedure is exemplified by Example 52.

Scheme 7: Buchwald-Hartwig cross-couplings with Boc-protected amines.

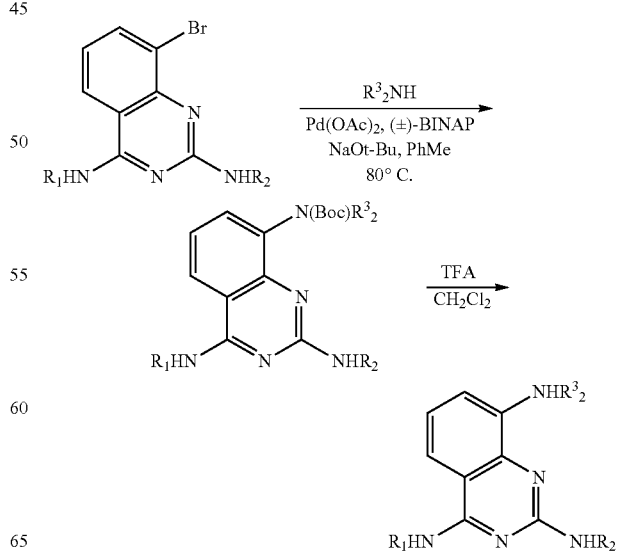

General Procedure H for Buchwald-Hartwig Cross-Couplings with Unprotected Amines The quinazoline analogs 53 and 66-67 were prepared by the procedure outlined in Scheme 8. This procedure is exemplified by Example 53.

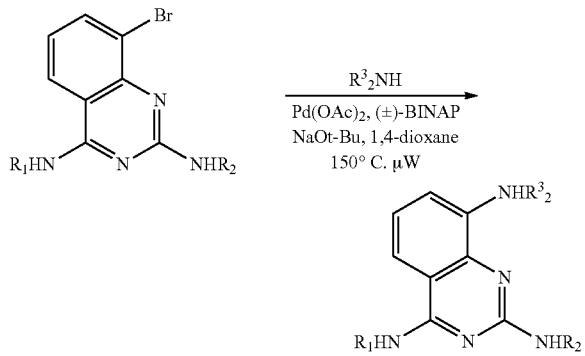

General Procedure I for Ullman Reactions with Amino Alcohols

The quinazoline analog 54 was prepared by the procedure outlined in Scheme 9. This procedure is exemplified by Example 54.

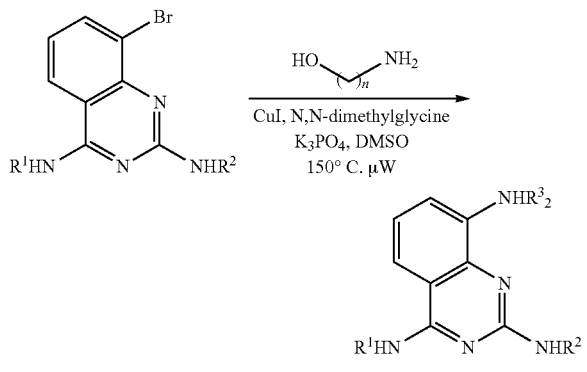

General J for Cyanide Addition

The quinazoline analog 55 and 99 was prepared by the procedure outlined in Scheme 10. This procedure is exemplified by Example 55.

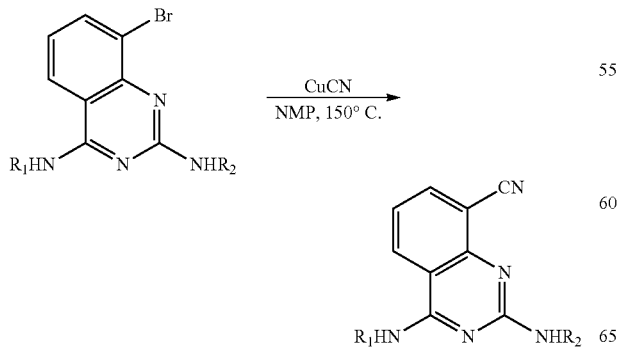

General Procedure K for Nitrile Reduction

The quinazoline analogs 56, 75, 78, 86-87, and 95-97 were prepared by the procedure outlined in Scheme 11. This procedure is exemplified by Example 56.

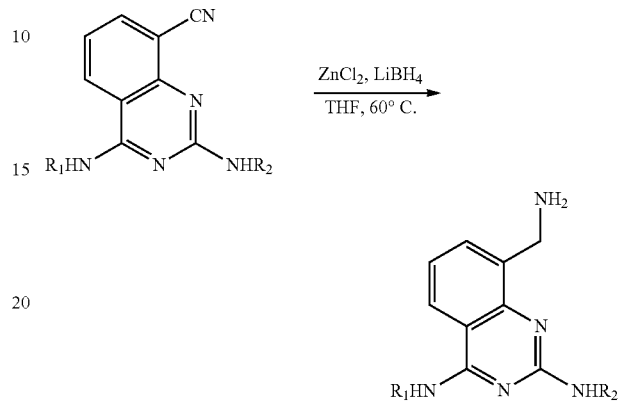

General Procedure L for Amidine Synthesis

The quinazoline analog 57 was prepared by the procedure outlined in Scheme 12. This procedure is exemplified by Example 57.

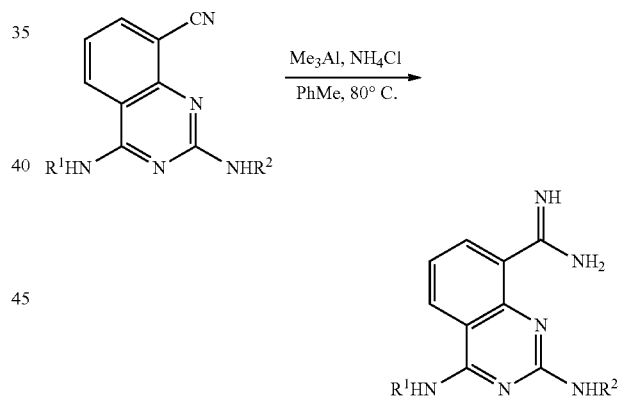

General Procedure M for Nitrile Reduction/Reductive Amination

The quinazoline analog 58 was prepared by the procedure outlined in Scheme 13. This procedure is exemplified by Example 58.

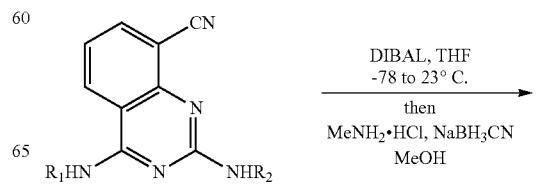

-continued

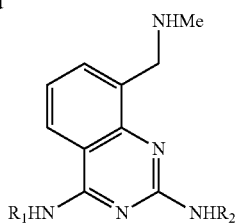

General Procedure N for Guanidine Synthesis
The quinazoline analog 59 was prepared by the procedure outlined in Scheme 14. This procedure is exemplified by Example 59.

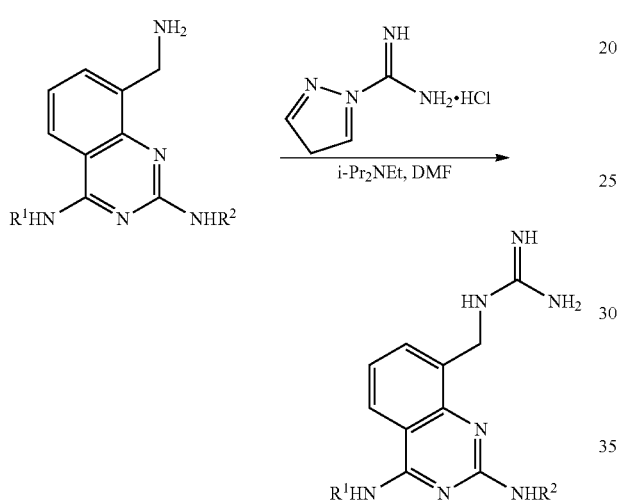

Example 1: (R)—$N^2$-(3-chloro-4-fluorophenyl)-$N^4$-(1-cyclopropylethyl)quinazoline-2,4-diamine

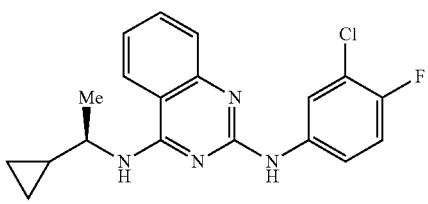 [SMILES: C[C@@H](Nc1nc(Nc2ccc(F)c(Cl)c2)nc2ccccc12)C1CC1]

Step A: 2,4-dichloroquinazoline (498 mg, 2.50 mmol, 1 eq.) was dissolved in THF (10 mL, 0.25 M). Triethylamine (0.767 mL, 5.50 mmol, 2.2 eq.) was added, followed by (R)-1-cyclopropylethylamine (0.333 mL, 3.13 mmol, 1.25 eq.). The reaction mixture was heated to 75° C. and stirred for 3 h. The reaction mixture was then allowed to cool to room temperature and concentrated in vacuo. The residual oil was redissolved in $CH_2Cl_2$ and treated with 50% aqueous $NH_4Cl$. The resulting biphasic mixture was passed through a phase separator and concentrated in vacuo. The residue was purified by silica gel chromatography (10-80% ethyl acetate in hexanes) to provide (R)-2-chloro-N-(1-cyclopropylethyl)quinazolin-4-amine as an off-white solid (559 mg, 91%). MS (ESI) m/z=248.10 (M+H)$^+$. LCMS Ret time (UV 214/254): 1.219 min.

Step B: (R)-2-chloro-N-(1-cyclopropylethyl)quinazolin-4-amine (99 mg, 0.40 mmol, 1 eq.) and 3-chloro-4-fluoroaniline (146 mg, 1.00 mmol, 2.5 eq.) were dissolved in 2-propanol (1.00 mL, 0.4 M) and a 4 M HCl solution in dioxane (75 µL, 0.300 mmol, 0.75 eq.) was added. The reaction mixture was heated to 120° C. for 30 min in a microwave reactor. The mixture was then concentrated in vacuo and purified by reverse phase preparative HPLC. The title compound was obtained as its corresponding trifluoroacetate salt (33 mg, 18% yield). $^1$H NMR (400 MHz, CDCl$_3$) δ 8.04 (dd, J=6.6, 2.6 Hz, 1H), 7.71 (m, 3H), 7.38 (m, 2H), 7.11 (t, J=8.7 Hz, 1H), 6.55 (d, J=7.2 Hz, 1H), 3.83 (sext, J=7.4 Hz, 1H), 1.45 (d, J=6.6 Hz, 3H), 1.09 (m, 1H), 0.71 (m, 1H), 0.58 (m, 1H), 0.41 (m, 2H). MS (ESI) m/z=357.10 (M+H)$^+$. LCMS Ret time (UV 214/254): 1.475 min.

Example 2: $N^2$-(3-chloro-4-fluorophenyl)-$N^4$-(2-methylpentan-3-yl)quinazoline-2,4-diamine

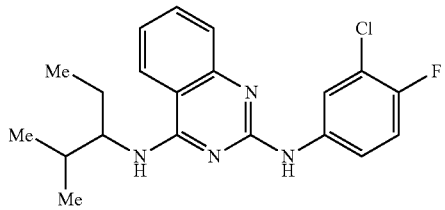 [SMILES: CCC(Nc1nc(Nc2ccc(F)c(Cl)c2)nc2ccccc12)C(C)C]

The title compound was obtained according to a procedure analogous to general procedure A. MS (ESI) m/z=374.70 (M+H)$^+$. LCMS Ret time (UV 214/254): 1.700 min.

Example 3: (R)—$N^2$-(cyclopentylmethyl)-$N^4$-(1-cyclopropylethyl)quinazoline-2,4-diamine

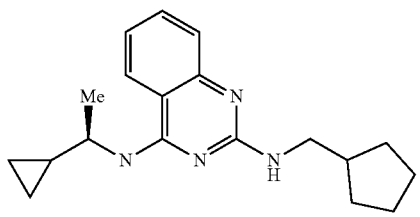 [SMILES: C[C@@H](Nc1nc(NCC2CCCC2)nc2ccccc12)C1CC1]

The title compound was obtained according to a procedure analogous to general procedure A. $^1$H NMR (400 MHz, (CD$_3$)$_2$SO) δ 9.31 (d, J=6.4 Hz, 1H), 8.34 (d, J=8.1 Hz, 1H), 7.79 (t, J=7.7 Hz, 1H), 7.41 (d, J=5.5 Hz, 2H), 3.89 (m, 1H), 3.35 (m, 2H), 2.16 (m, 1H), 1.74 (m, 2H), 1.55 (m, 4H), 1.35 (d, J=6.3 Hz, 3H), 1.26 (m, 1H), 1.17 (m, 1H), 0.57 (m, 1H), 0.45 (m, 1H), 0.32 (m, 2H). MS (ESI) m/z=311.20 (M+H)$^+$. LCMS Ret time (UV 214/254): 1.468 min.

Example 4: (R)—N²-(cyclohexylmethyl)-N⁴-(1-cyclopropylethyl)quinazoline-2,4-diamine

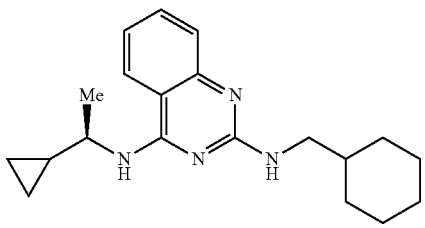 [SMILES: C[C@@H](Nc1nc(NCC2CCCCC2)nc2ccccc12)C1CC1]

The title compound was obtained according to a procedure analogous to general procedure A. ¹H NMR (400 MHz, CDCl₃) δ 9.80 (t, J=5.5 Hz, 1H), 7.63 (t, J=7.7 Hz, 1H), 7.59 (d, J=8.8 Hz, 1H), 7.57 (d, J=8.6 Hz, 1H), 7.26 (t, 1H), 6.36 (d, J=7.3 Hz, 1H), 3.87 (sext, J=6.8 Hz, 1H), 3.32 (m, 2H), 1.97 (m, 2H), 1.75 (m, 4H), 1.62 (m, 2H), 1.41 (d, J=6.6 Hz, 3H), 1.21 (m, 3H), 1.07 (m, 1H), 0.97 (m, 2H), 0.71 (ddd, J=13.4, 9.0, 4.5 Hz, 1H), 0.61 (ddd, J=16.7, 8.3, 4.8 Hz, 1H), 0.44 (m, 2H). MS (ESI) m/z=357.10 (M+H)⁺. LCMS Ret time (UV 214/254): 1.475 min.

Example 5: (R)—N²-(cycloheptylmethyl)-N⁴-(1-cyclopropylethyl)quinazoline-2,4-diamine

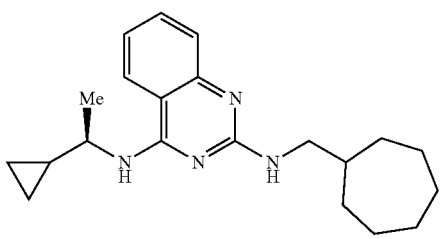 [SMILES: C[C@@H](Nc1nc(NCC2CCCCCC2)nc2ccccc12)C1CC1]

The title compound was obtained according to a procedure analogous to general procedure A. ¹H NMR (400 MHz, CD₃OD) δ 8.20 (d, J=7.6 Hz, 1H), 7.77 (t, J=8.3 Hz, 1H), 7.41 (m, 2H), 3.94 (m, 1H), 3.31 (m, 2H), 1.84 (m, 5H), 1.57 (m, 5H), 1.44 (d, J=6.3 Hz, 3H), 1.29 (m, 2H), 1.20 (s, 1H), 0.66 (m, 1H), 0.55 (m, 1H), 0.41 (m, 1H), 0.33 (m, 1H). MS (ESI) m/z=339.20 (M+H)⁺. LCMS Ret time (UV 214/254): 1.597 min.

Example 6: (R)—N⁴-(1-cyclopropylethyl)-N²-(3,4,5-trifluorophenyl)quinazoline-2,4-diamine

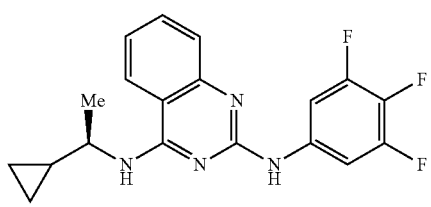 [SMILES: C[C@@H](Nc1nc(Nc2cc(F)c(F)c(F)c2)nc2ccccc12)C1CC1]

The title compound was obtained according to a procedure analogous to general procedure A. ¹H NMR (400 MHz, (CD₃)₂SO) δ 10.63 (br s, 1H), 9.32 (br s, 1H), 8.39 (d, J=8.1 Hz, 1H), 7.83 (t, J=7.6 Hz, 1H), 7.59 (dd, J=10.0, 6.4 Hz, 2H), 7.55 (d, J=8.1 Hz, 1H), 7.47 (t, J=7.6 Hz, 1H), 3.83 (sext, J=6.8 Hz, 2H), 1.36 (d, J=6.7 Hz, 3H), 1.18 (m, 1H), 0.58 (m, 1H), 0.45 (m, 1H), 0.35 (sext, J=5.0 Hz, 1H), 0.23 (sext, J=4.8 Hz, 1H). MS (ESI) m/z=359.10 (M+H)⁺. LCMS Ret time (UV 214/254): 1.495 min.

Example 7: N⁴-(thiophen-2-ylmethyl)-N²-(3-(trifluoromethoxy)phenyl)quinazoline-2,4-diamine

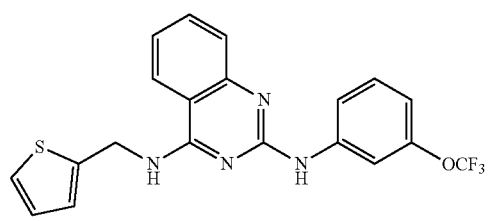 [SMILES: FC(F)(F)Oc1cccc(Nc2nc(NCc3cccs3)c3ccccc3n2)c1]

The title compound was prepared according to a procedure analogous to general procedure A. MS (ESI) m/z=417.10 (M+H)⁺. LCMS Ret time (UV 214/254): 1.489 min.

Example 8: N⁴-(furan-2-ylmethyl)-N²-(3-(trifluoromethyl)phenyl)quinazoline-2,4-diamine

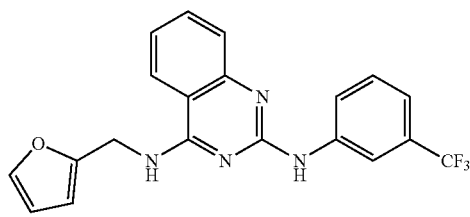 [SMILES: FC(F)(F)c1cccc(Nc2nc(NCc3ccco3)c3ccccc3n2)c1]

The title compound was prepared according to a procedure analogous to general procedure A. MS (ESI) m/z=385.20 (M+H)⁺. LCMS Ret time (UV 214/254): 1.419 min.

Example 9: N²-(3,5-dichlorophenyl)-N⁴-(thiophen-2-ylmethyl)quinazoline-2,4-diamine

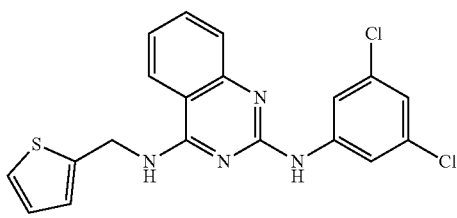 [SMILES: Clc1cc(Cl)cc(Nc2nc(NCc3cccs3)c3ccccc3n2)c1]

The title compound was prepared according to a procedure analogous to general procedure A. MS (ESI) m/z=401.10 (M+H)⁺. LCMS Ret time (UV 214/254): 1.545 min.

Example 10: N²-(2,3-dihydro-1H-inden-5-yl)-N⁴-(furan-2-ylmethyl)quinazoline-2,4-diamine

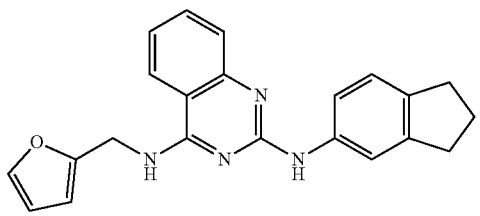 [SMILES: c1coc(CNc2nc(Nc3ccc4c(c3)CCC4)nc3ccccc23)c1]

The title compound was prepared according to a procedure analogous to general procedure A. MS (ESI) m/z=357.20 (M+H)⁺. LCMS Ret time (UV 214/254): 1.444 min.

Example 11: N²-(1H-benzo [d][1,2,3]triazol-5-yl)-N⁴-(furan-2-ylmethyl)quinazoline-2,4-diamine

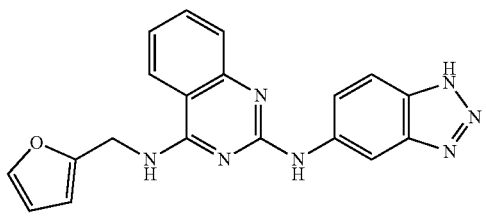 [SMILES: c1coc(CNc2nc(Nc3ccc4[nH]nnc4c3)nc3ccccc23)c1]

The title compound was prepared according to a procedure analogous to general procedure A. MS (ESI) m/z=358.20 (M+H)⁺. LCMS Ret time (UV 214/254): 1.052 min.

Example 12: N⁴-(furan-2-ylmethyl)-N²-(3-methoxybenzyl)quinazoline-2,4-diamine

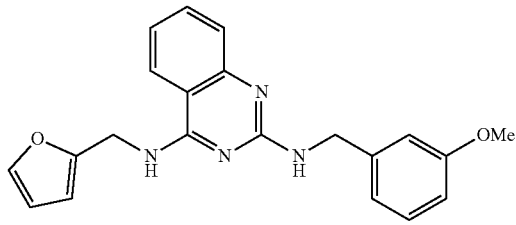 [SMILES: COc1cccc(CNc2nc(NCc3ccco3)c3ccccc3n2)c1]

The title compound was prepared according to a procedure analogous to general procedure A. MS (ESI) m/z=361.20 (M+H)⁺. LCMS Ret time (UV 214/254): 1.305 min.

Example 13: 3-((4-((thiophen-2-ylmethyl)amino)quinazolin-2-yl)amino)phenol

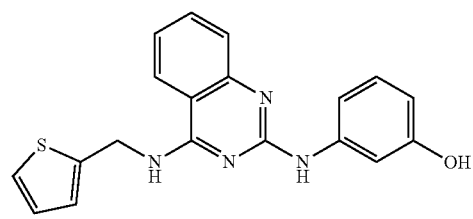 [SMILES: Oc1cccc(Nc2nc(NCc3cccs3)c3ccccc3n2)c1]

The title compound was prepared according to a procedure analogous to general procedure A. MS (ESI) m/z=349.20 (M+H)⁺. LCMS Ret time (UV 214/254): 1.188 min.

Example 14: N²-(4-fluorobenzyl)-N⁴-(furan-2-ylmethyl)quinazoline-2,4-diamine

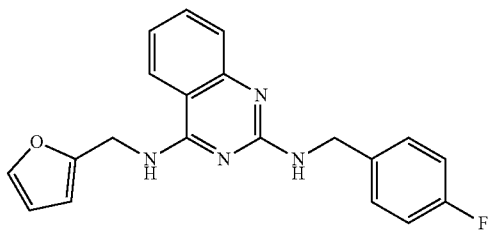 [SMILES: Fc1ccc(CNc2nc(NCc3ccco3)c3ccccc3n2)cc1]

The title compound was prepared according to a procedure analogous to general procedure A. MS (ESI) m/z=349.20 (M+H)⁺. LCMS Ret time (UV 214/254): 1.315 min.

Example 15: N²-(3-chloro-4-fluorophenyl)-N⁴-((5-methylfuran-2-yl)methyl)quinazoline-2,4-diamine

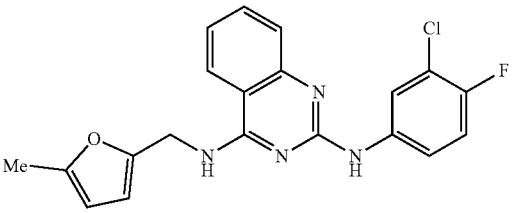 [SMILES: Cc1ccc(CNc2nc(Nc3ccc(F)c(Cl)c3)nc3ccccc23)o1]

The title compound was prepared according to a procedure analogous to general procedure A. MS (ESI) m/z=383.20 (M+H)⁺. LCMS Ret time (UV 214/254): 1.450 min.

Example 16: N²-(3-chloro-4-fluorophenyl)-N⁴-(2-methylbutyl)quinazoline-2,4-diamine

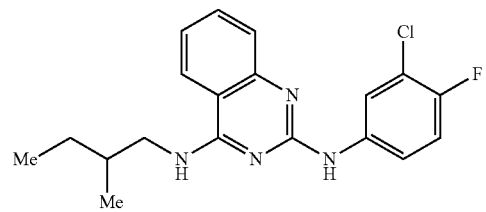 [SMILES: CCC(C)CNc1nc(Nc2ccc(F)c(Cl)c2)nc2ccccc12]

The title compound was prepared according to a procedure analogous to general procedure A. MS (ESI) m/z=359.20 (M+H)⁺. LCMS Ret time (UV 214/254): 1.532 min.

Example 17: N²-(cyclobutylmethyl)-N⁴-(cyclopropylmethyl)quinazoline-2,4-diamine

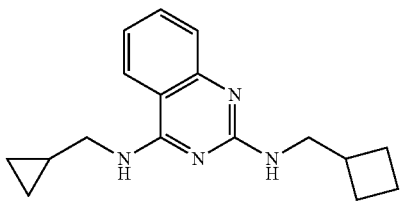 [SMILES: c1ccc2c(NCC3CC3)nc(NCC3CCC3)nc2c1]

The title compound was prepared according to a procedure analogous to general procedure A. MS (ESI) m/z=283.30 (M+H)⁺. LCMS Ret time (UV 214/254): 1.416 min.

Example 18: N⁴-(cyclopropylmethyl)-N²-((THF-2-yl)methyl)quinazoline-2,4-diamine

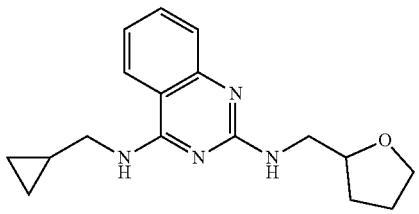 [SMILES: c1ccc2c(NCC3CC3)nc(NCC3CCCO3)nc2c1]

The title compound was prepared according to a procedure analogous to general procedure A. MS (ESI) m/z=299.20 (M+H)⁺. LCMS Ret time (UV 214/254): 1.220 min.

Example 19: (R)—N⁴-(1-cyclopropylethyl)-N²-(2,4-difluorobenzyl)quinazoline-2,4-diamine

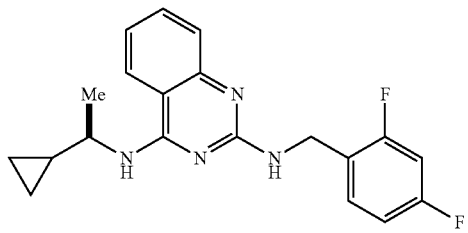 [SMILES: C[C@@H](Nc1nc(NCc2ccc(F)cc2F)nc2ccccc12)C1CC1]

The title compound was prepared according to a procedure analogous to general procedure A. MS (ESI) m/z=356.48 (M+H)⁺. LCMS Ret time (UV 214/254): 1.687 min.

Example 20: (R)—N²-(3,5-difluorophenyl)-N⁴-(3-methylbutan-2-yl)quinazoline-2,4-diamine

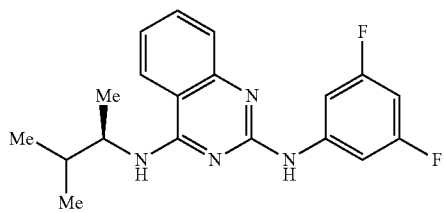 [SMILES: CC(C)[C@@H](C)Nc1nc(Nc2cc(F)cc(F)c2)nc2ccccc12]

The title compound was prepared according to a procedure analogous to general procedure A. MS (ESI) m/z=343.20 (M+H)⁺. LCMS Ret time (UV 214/254): 1.572 min.

Example 21: N²-(3-chloro-4-fluorophenyl)-N⁴-(dicyclopropylmethyl)quinazoline-2,4-diamine

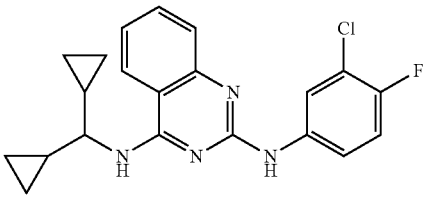 [SMILES: Fc1ccc(Nc2nc(NC(C3CC3)C3CC3)c3ccccc3n2)cc1Cl]

The title compound was prepared according to a procedure analogous to general procedure A. MS (ESI) m/z=383.10 (M+H)⁺. LCMS Ret time (UV 214/254): 1.561 min.

Example 22: N⁴-((1H-imidazol-2-yl)methyl)-N²-(3,5-difluorophenyl)quinazoline-2,4-diamine

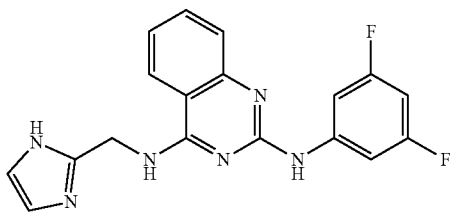 [SMILES: Fc1cc(F)cc(Nc2nc(NCc3ncc[nH]3)c3ccccc3n2)c1]

The title compound was obtained according to a procedure analogous to general procedure A. ¹H NMR (400 MHz, CD₃OD) δ 8.22 (d, J=7.7 Hz, 1H), 7.93 (dt, J=8.5, 1.2 Hz, 1H), 7.68 (d, J=8.3 Hz, 1H), 7.57 (dt, J=8.3, 1.0 Hz, 1H), 7.49 (s, 2H), 7.04 (m, 2H), 6.81 (tt, J=9.1, 2.3 Hz, 1H), 5.16 (s, 2H). MS (ESI) m/z=353.10 (M+H)⁺. LCMS Ret time (UV 214/254): 0.834 min.

Example 23: (R)-3-((4-((1-cyclopropylethyl)amino)quinazolin-2-yl)amino)-5-fluorobenzonitrile

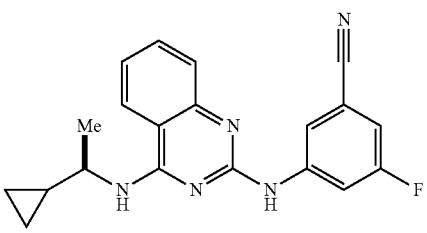 [SMILES: C[C@@H](Nc1nc(Nc2cc(F)cc(C#N)c2)nc2ccccc12)C1CC1]

The title compound was obtained according to a procedure analogous to general procedure A. ¹H NMR (400 MHz, CDCl₃) δ 7.91 (m, 2H), 7.68 (m, 3H), 7.33 (td, J=7.2, 1.6 Hz, 1H), 7.00 (m, 1H), 6.03 (br s, 1H), 3.75 (m, 1H), 1.46 (d, J=6.4 Hz, 3H), 1.12 (m, 1H), 0.68 (m, 1H), 0.57 (m, 1H), 0.42 (sext, J=4.9 Hz, 1H). MS (ESI) m/z=348.56 (M+H)⁺. LCMS Ret time (UV 214/254): 1.39 min.

Example 24: (R)—N⁴-(1-cyclopropylethyl)-N²-(4-fluoro-3-methylbenzyl)quinazoline-2,4-diamine

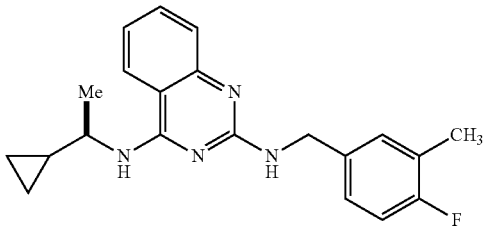 [SMILES: Cc1cc(CNc2nc(N[C@H](C)C3CC3)c3ccccc3n2)ccc1F]

The title compound was obtained according to a procedure analogous to general procedure A. MS (ESI) m/z=351.1 (M+H)⁺. LCMS Ret time (UV 214/254): 1.469 min Example 25: (R)—N²-(3-chloro-2-fluorobenzyl)-N⁴-(1-cyclopropylethyl)quinazoline-2,4-diamine

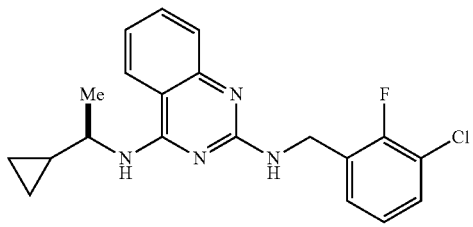 [SMILES: C[C@@H](Nc1nc(NCc2cccc(Cl)c2F)nc2ccccc12)C1CC1]

The title compound was obtained according to a procedure analogous to general procedure A. ¹H NMR (400 MHz, CD₃OD) δ 8.35 (d, J=8.0 Hz, 1H), 7.96 (t, J=5.6 Hz, 1H), 7.53 (4m ovlp, 4H), 7.44 (t, J=7.2 Hz, 1H), 3.91 (m, 1H), 4.90 (m, 2H), 1.46 (d, J=6.4 Hz, 3H), 1.26 (m, 1H), 0.76 (m, 1H), 0.72 (m, 1H), 0.62 (sext, J=4.8 Hz, 1H), 0.58 (m, 1H), 0.44 (sext, J=5.0 Hz, 1H). MS (ESI) m/z=371.1 (M+H)⁺. LCMS Ret time (UV 214/254): 1.461

Example 26: (R)—N⁴-(1-cyclopropylethyl)-N²-(2-fluoro-3-methylbenzyl)quinazoline-2,4-diamine

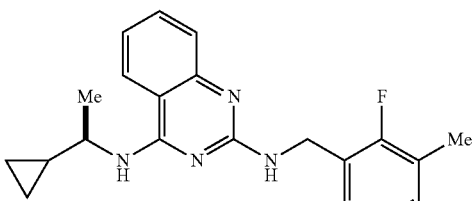

The title compound was obtained according to a procedure analogous to general procedure A. ¹H NMR (400 MHz, CD₃OD) δ 8.18 (d, J=8.0 Hz, 1H), 7.76 (td, J=8.4, 1.2 Hz, 1H), 7.48 (2m ovlp, 2H), 7.16 (2m ovlp, 2H), 7.02 (t, J=7.6 Hz, 1H), 4.71 (m, 2H), 3.81 (m, 1H), 2.32 (s, 3H), 1.38 (d, J=6.4 Hz, 3H), 1.11 (m, 1H), 0.59 (m, 1H), 0.43 (m, 1H), 0.26 (m, 1H). MS (ESI) m/z=351.10 (M+H)⁺. LCMS Ret time (UV 214/254): 1.459 min.

Example 27: (R)—N⁴-(1-cyclopropylethyl)-N²-(3-methoxybenzyl)quinazoline-2,4-diamine

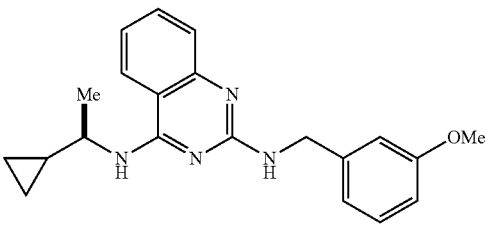 [SMILES: COc1cccc(CNc2nc(N[C@H](C)C3CC3)c3ccccc3n2)c1]

The title compound was obtained according to a procedure analogous to general procedure A. ¹H NMR (400 MHz, CDCl₃) δ 7.57 (2m ovlp, 2H), 7.49 (d, J=8.4 Hz, 1H), 7.25 (t, J=8.2 Hz, 1H), 7.14 (t, J=8.4 Hz, 1H), 6.97 (2m ovlp, 2H), 6.81 (d, J=8.2, 2.0 Hz, 1H), 4.69 (d, J=5.6 Hz, 2H), 3.81 (s, 3H), 3.78 (m, 1H), 1.32 (d, J=6.4 Hz, 3H), 1.01 (m, 1H), 0.51 (sext, J=5.0 Hz, 1H), 0.50 (m, 1H), 0.34 (sext, J=4.7 Hz, 1H). MS (ESI) m/z=349.26 (M+H)⁺. LCMS Ret time (UV 214/254): 1.52 min Example 28: (R)—N⁴-(1-cyclopropylethyl)-N²-(3-(trifluoromethyl)benzyl)quinazoline-2,4-diamine

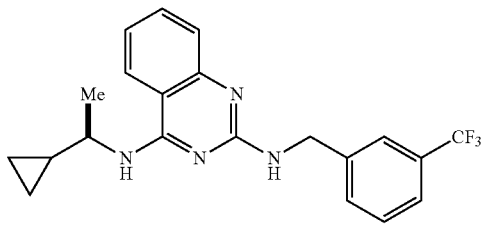 [SMILES: C[C@@H](Nc1nc(NCc2cccc(C(F)(F)F)c2)nc2ccccc12)C1CC1]

The title compound was obtained according to a procedure analogous to general procedure A. ¹H NMR (400 MHz, CDCl₃) δ 7.54 (4m ovlp, 4H), 7.47 (2m ovlp, 2H), 7.45 (t, J=7.2 Hz, 1H), 7.20 (t, J=7.2 Hz, 1H), 5.87 (br d, J=2.4 Hz, 1H), 4.75 (d, J=5.6 Hz, 2H), 3.70 (m, 1H), 1.28 (d, J=6.8 Hz, 3H), 1.00 (m, 1H), 0.59 (m, 1H), 0.40 (m, 1H), 0.29 (2m ovlp, 2H). MS (ESI) m/z=387.08 (M+H)⁺. LCMS Ret time (UV 214/254): 1.500 min.

Example 29: (R)—N⁴-(1-cyclopropylethyl)-N²-(2-fluorobenzyl)quinazoline-2,4-diamine

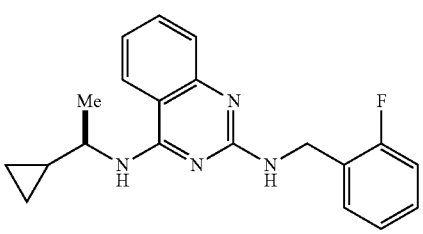 [SMILES: C[C@@H](Nc1nc(NCc2ccccc2F)nc2ccccc12)C1CC1]

The title compound was obtained according to a procedure analogous to general procedure A. ¹H NMR (400 MHz, CDCl₃) δ 8.82 (br s, 1H), 7.78 (d, J=7.6 Hz, 1H), 7.67 (t, J=7.2 Hz, 1H), 7.63 (J=7.6 Hz, 1H), 7.56 (t, J=8.4 Hz, 1H), 7.34 (2m ovlp, 2H), 7.09 (2m ovlp, 2H), 6.79 (br d, J=6.8 Hz, 1H), 4.75 (d, J=5.6 Hz, 2H), 3.80 (m, 1H), 1.34 (d, J=6.4 Hz, 3H), 1.07 (m, 1H), 0.65 (m, 1H), 0.35 (m, 1H), 0.29 (m, 1H). MS (ESI) m/z=337.61 (M+H)+. LCMS Ret time (UV 214/254): 1.700 min.

Example 30: ((R)—N²-(3-chloro-2,4-difluorophenyl)-N⁴-(1-cyclopropylethyl)quinazoline-2,4-diamine

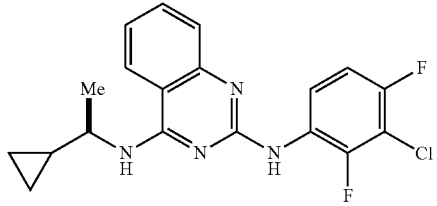 [SMILES: C[C@@H](Nc1nc(Nc2ccc(F)c(Cl)c2F)nc2ccccc12)C1CC1]

The title compound was obtained according to a procedure analogous to general procedure A. ¹H NMR (400 MHz, CDCl₃) δ 8.68 (m, 1H), 7.63 (3m ovlp, 3H), 7.27 (2m ovlp, 2H), 7.01 (2m ovlp, 2H), 5.70 (br d, J=7.2 Hz, 1H), 3.85 (m, 1H), 1.39 (d, J=6.4 Hz, 3H), 1.06 (m, 1H), 0.63 (m, 1H), 0.56 (m, 1H), 0.44 (2m ovlp, 2H). MS (ESI) m/z=375.55 (M+H)+. LCMS Ret time (UV 214/254): 1.470 min.

Example 31: N²-(3-chloro-4-fluorophenyl)-N⁴-(2-ethylbutyl)quinazoline-2,4-diamine

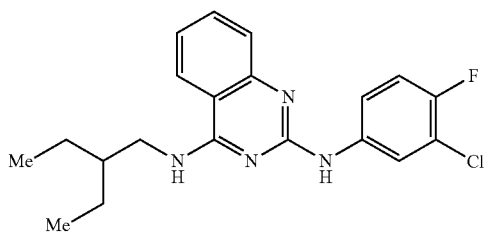 [SMILES: CCC(CC)CNc1nc(Nc2ccc(F)c(Cl)c2)nc2ccccc12]

The title compound was obtained according to a procedure analogous to general procedure A. ¹H NMR (400 MHz, CD₃OD) δ 8.01 (2m ovlp, 2H), 7.62 (td, J=7.6, 2.0 Hz, 1H), 7.47 (m, 2H), 7.24 (td, J=7.2, 1.8 Hz, 1H), 7.14 (t, J=8.2 Hz, 1H), 3.54 (d, J=7.2 Hz, 2H), 1.76 (quint, J=6.4 Hz, 1H), 1.43 (m, 4H), 0.92 (t, J=7.6 Hz, 6H). MS (ESI) m/z=374.79 (M+H)+. LCMS Ret time (UV 214/254): 2.803 min.

Example 32: N²-(3,4-dichlorophenyl)-N⁴-(furan-2-ylmethyl)quinazoline-2,4-diamine

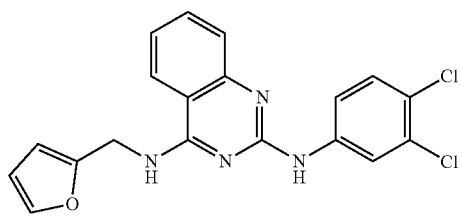 [SMILES: Clc1ccc(Nc2nc(NCc3ccco3)c3ccccc3n2)cc1Cl]

Example 33: N⁴-benzyl-N²-phenylquinazoline-2,4-diamine

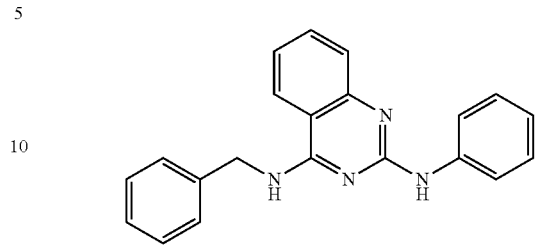

Example 34: (R)—N²-(3-chloro-4-fluorophenyl)-N⁴-(1-cyclopropylpropyl)quinazoline-2,4-diamine

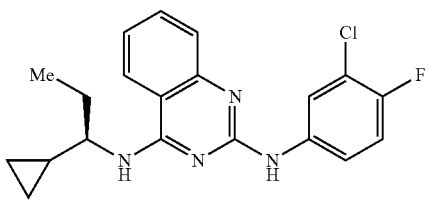 [SMILES: CC[C@@H](Nc1nc(Nc2ccc(F)c(Cl)c2)nc2ccccc12)C1CC1]

Step A: To a 0.5 M solution of Ti(OEt)₄ (technical grade, ~20% Ti; 10.48 mL, 50.00 mmol, 2 eq.) and cyclopropanecarboxaldehyde (2.06 mL, 27.50 mmol, 1.1 eq.) in THF (25 mL, 1 M) was added (S)-2-methylpropane-2-sulfinamide (3.03 g, 25.00 mmol, 1 eq.). The resulting mixture was stirred at room temperature and the conversion was followed by TLC. Upon completion, the reaction was poured into an equal volume of brine (11 mL) with rapid stirring. The resulting suspension was filtered through a plug of Celite, and the filter cake was washed with CH₂Cl₂. The organic layer was washed with brine. The brine layer was extracted once with a small volume of CH₂Cl₂, and the combined organic portions were dried over MgSO₄, filtered, and concentrated. The crude was purified by silica gel chromatography (CH₂Cl₂) to provide (S,E)-N-(cyclopropylmethylene)-2-methylpropane-2-sulfinamide as a yellow oil (3.617 g, 83%).

Step B: To a solution of (S,E)-N-(cyclopropylmethylene)-2-methylpropane-2-sulfinamide (1.04 g, 6.00 mmol, 1 eq.) in CH₂Cl₂ (35 mL, 0.17 M) at −61° C. was added ethylmagnesium bromide (3 M in diethyl ether; 4.0 mL, 12.00 mmol, 2 eq.), via dropwise addition. The mixture was stirred at −61° C. for 2 h and then slowly warmed to room temperature overnight with stirring. When complete, the reaction was quenched by the addition of saturated aqueous NH₄Cl and the aqueous layer was extracted with CH₂Cl₂. The combined organic layers were dried over MgSO₄, filtered, and concentrated. The sulfinamide diastereomers were separated by silica gel chromatography (0-3% MeOH in CH₂Cl₂) to provide (S)—N—((R)-1-cyclopropylpropyl)-2-methylpropane-2-sulfinamide as a white solid (1.083 g, 89%)¹H NMR (400 MHz, CDCl₃) δ 3.11 (br d, J=3.6 Hz, 1H), 2.48 (ddd, J=11.2, 8.8, 6.2 Hz, 1H), 1.70 (m, 2H), 1.21 (s, 9H), 1.00 (t, J=7.5 Hz, 3H), 0.78 (tdd, J=13.3, 8.3, 5.0 Hz, 1H), 0.53 (m, 2H), 0.34 (m, 1H), 0.20 (m, 1H).

Step C: To (S)—N—((R)-1-cyclopropylpropyl)-2-methyl-propane-2-sulfinamide (1.08 g, 5.31 mmol, 1 eq.) was added 1:1 (v/v) MeOH (2.66 mL, 2 M) and 4 M HCl in dioxane solution (2.66 mL, 10.62 mmol, 2 eq.). The mixture was stirred at room temperature for 30 min and then concentrated to near dryness. Diethyl ether was added to precipitate the amine hydrochloride. The precipitate was then filtered off and washed with a 1:1 (v/v) mixture of diethyl ether and hexanes to provide the (R)-1-cyclopropylpropan-1-amine hydrochloride as a white solid (667 mg, 93%). $^1$H NMR (400 MHz, CDCl$_3$) δ 8.50 (s, 3H), 2.36 (m, 1H), 1.93 (m, 2H), 1.12 (t, J=7.5 Hz, 3H), 1.07 (m, 1H), 0.66 (m, 3H), 0.34 (m, 1H).

Step D: The title compound was obtained according to a procedure analogous to general procedure A, using (R)-1-cyclopropylpropan-1-amine hydrochloride, which was prepared by a procedure analogous to the procedure used to prepare Example 34, Step C. $^1$H NMR (400 MHz, CDCl$_3$) δ 7.97 (dd, J=6.6, 2.6 Hz, 1H), 7.71 (m, 3H), 7.37 (m, 2H), 7.10 (t, J=8.7 Hz, 1H), 6.55 (d, J=8.0 Hz, 1H), 3.66 (m, 1H), 1.86 (m, 2H), 1.05 (t, J=7.5 Hz, 3H), 1.02 (m, 1H), 0.74 (m, 1H), 0.53 (m, 1H), 0.46 (m, 1H), 0.32 (sext, J=4.9 Hz, 1H). MS (ESI) m/z=371.10 (M+H)$^+$. LCMS Ret time (UV 214/254): 1.542 min.

Example 35: (R)—N$^4$-(1-cyclopropylpropyl)-N$^2$-(3,5-difluorophenyl)quinazoline-2,4-diamine

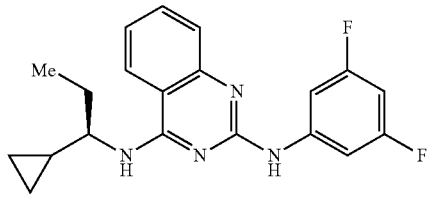 [SMILES: CC[C@@H](Nc1nc(Nc2cc(F)cc(F)c2)nc2ccccc12)C1CC1]

The title compound was obtained according to a procedure analogous to general procedure A, using (R)-1-cyclopropylpropan-1-amine hydrochloride, which was prepared by a procedure analogous to general procedure B. $^1$H NMR (400 MHz, CDCl$_3$) δ 7.73 (dd, J=13.1, 8.0 Hz, 3H), 7.40 (ddd, J=8.2, 6.2, 1.9 Hz, 1H), 7.33 (m, 2H), 6.59 (m, 2H), 3.67 (m, 1H), 1.89 (m, 2H), 1.09 (t, J=7.5 Hz, 3H), 1.03 (m, 1H), 0.77 (m, 1H), 0.52 (m, 2H), 0.35 (sext, J=4.9 Hz, 1H). MS (ESI) m/z=355.10 (M+H)$^+$. LCMS Ret time (UV 214/254): 1.503 min.

Example 36: (R)—N$^2$-(3-chloro-4-fluorophenyl)-N$^4$-(1-cyclopropylbutyl)quinazoline-2,4-diamine

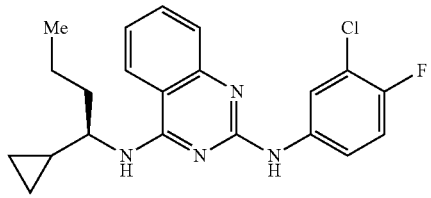 [SMILES: CCC[C@@H](Nc1nc(Nc2ccc(F)c(Cl)c2)nc2ccccc12)C1CC1]

The title compound was obtained according to a procedure analogous to general procedure A, using (R)-1-cyclopropylbutan-1-amine hydrochloride, which was prepared by a procedure analogous to general procedure B. $^1$H NMR (400 MHz, CDCl$_3$) δ 7.95 (dd, J=6.6, 2.6 Hz, 1H), 7.70 (m, 3H), 7.36 (m, 2H), 7.10 (t, J=8.7 Hz, 1H), 6.58 (d, J=8.5 Hz, 1H), 3.77 (ddd, J=15.6, 8.6, 7.0 Hz, 1H), 1.78 (m, 2H), 1.46 (sext, J=7.3 Hz, 2H), 1.02 (m, 1H), 0.91 (t, J=7.3 Hz, 3H), 0.71 (m, 1H), 0.51 (m, 1H), 0.44 (sext, J=4.9 Hz, 1H), 0.33 (sext, J=4.9 Hz, 1H). MS (ESI) m/z=385.00 (M+H)$^+$. LCMS Ret time (UV 214/254): 1.607 min.

Example 37: (R)—N$^2$-(3-chloro-4-fluorophenyl)-N$^4$-(1-(thiophen-2-yl)ethyl)quinazoline-2,4-diamine

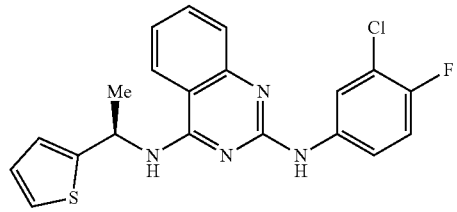 [SMILES: C[C@@H](Nc1nc(Nc2ccc(F)c(Cl)c2)nc2ccccc12)c1cccs1]

The title compound was obtained according to a procedure analogous to general procedure A, using (R)-1-(thiophen-2-yl)ethan-1-amine hydrochloride, which was prepared by a procedure analogous to general procedure B. $^1$H NMR (400 MHz, CDCl$_3$) δ 7.95 (dd, J=6.6, 2.6 Hz, 1H), 7.75 (m, 2H), 7.63 (d, J=8.2 Hz, 1H), 7.39 (m, 2H), 7.30 (dd, J=5.1, 1.1 Hz, 1H), 7.12 (t, J=8.7 Hz, 1H), 7.08 (d, J=3.5 Hz, 1H), 7.02 (dd, J=5.1, 3.6 Hz, 1H), 6.59 (d, J=7.4 Hz, 1H), 5.79 (quint, J=7.0 Hz, 1H), 1.85 (d, J=6.8 Hz, 3H). MS (ESI) m/z=399.00 (M+H)$^+$. LCMS Ret time (UV 214/254): 1.498 min.

Example 38: (R)—N$^2$-(3,5-difluorophenyl)-N$^4$-(1-(thiophen-2-yl)ethyl)quinazoline-2,4-diamine

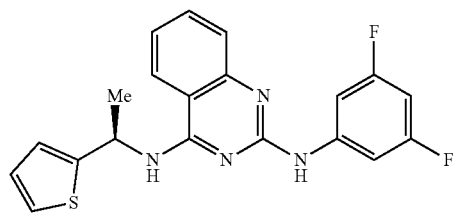 [SMILES: C[C@@H](Nc1nc(Nc2cc(F)cc(F)c2)nc2ccccc12)c1cccs1]

The title compound was obtained according to a procedure analogous to general procedure A, using (R)-1-(thiophen-2-yl)ethan-1-amine hydrochloride, which was prepared by a procedure analogous to general procedure B. $^1$H NMR (400 MHz, CDCl$_3$) δ 7.75 (m, 2H), 7.67 (d, J=8.2 Hz, 1H), 7.40 (ddd, J=8.3, 6.5, 1.7 Hz, 1H), 7.33 (dd, J=8.8, 2.2 Hz, 2H), 7.29 (dd, J=5.1, 1.1 Hz, 1H), 7.12 (d, J=3.5 Hz, 1H), 7.02 (dd, J=5.1, 3.6 Hz, 1H), 6.70 (d, J=7.4 Hz, 1H), 6.61 (tt, J=8.8, 2.3 Hz, 1H), 5.83 (quint, J=7.0 Hz, 1H), 1.87 (d, J=6.8 Hz, 3H). MS (ESI) m/z=383.10 (M+H)$^+$. LCMS Ret time (UV 214/254): 1.447 min.

Example 39: (R)—N²-(3-chloro-4-fluorophenyl)-N⁴-(1-(thiophen-2-yl)propyl)quinazoline-2,4-diamine

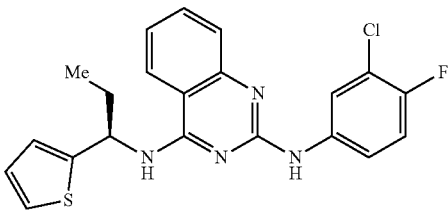 [SMILES: CC[C@@H](Nc1nc(Nc2ccc(F)c(Cl)c2)nc2ccccc12)c1cccs1]

The title compound was obtained according to a procedure analogous to general procedure A, using (R)-1-(thiophen-2-yl)propan-1-amine hydrochloride, which was prepared by a procedure analogous to general procedure B. ¹H NMR (400 MHz, CDCl₃) δ 7.89 (dd, J=6.5, 2.6 Hz, 1H), 7.68 (m, 3H), 7.37 (m, 2H), 7.27 (dd, J=5.1, 1.2 Hz, 1H), 7.12 (t, J=8.7 Hz, 1H), 7.04 (d, J=3.2 Hz, 1H), 6.99 (dd, J=5.0, 3.6 Hz, 1H), 6.71 (d, J=7.9 Hz, 1H), 5.55 (q, J=7.5 Hz, 1H), 2.16 (m, 2H), 1.05 (t, J=7.4 Hz, 3H). MS (ESI) m/z=413.10 (M+H)⁺. LCMS Ret time (UV 214/254): 1.544 min.

Example 40: (R)—N²-(3-chloro-4-fluorophenyl)-N⁴-(3,3-dimethylbutan-2-yl)quinazoline-2,4-diamine

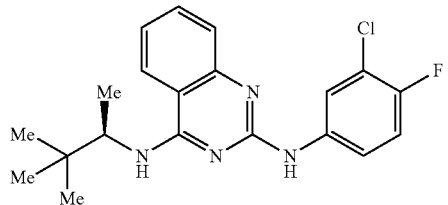 [SMILES: C[C@@H](Nc1nc(Nc2ccc(F)c(Cl)c2)nc2ccccc12)C(C)(C)C]

The title compound was obtained according to a procedure analogous to general procedure A. ¹H NMR (400 MHz, CDCl₃) δ 8.14 (dd, J=6.6, 2.6 Hz, 1H), 7.75 (m, 2H), 7.60 (d, J=8.1 Hz, 1H), 7.39 (m, 2H), 7.14 (t, J=8.7 Hz, 1H), 6.26 (d, J=9.3 Hz, 1H), 4.46 (ddd, J=9.3, 6.8, 2.6 Hz, 1H), 1.31 (d, J=6.8 Hz, 3H), 1.06 (s, 9H). MS (ESI) m/z=373.00 (M+H)⁺. LCMS Ret time (UV 214/254): 1.601 min.

Example 41: (R)—N²-(3,5-difluorophenyl)-N⁴-(3,3-dimethylbutan-2-yl)quinazoline-2,4-diamine

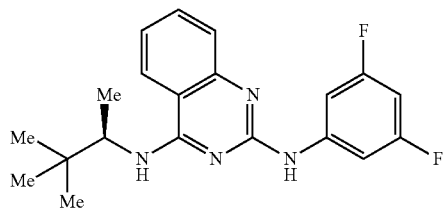 [SMILES: C[C@@H](Nc1nc(Nc2cc(F)cc(F)c2)nc2ccccc12)C(C)(C)C]

The title compound was obtained according to a procedure analogous to general procedure A. ¹H NMR (400 MHz, CDCl₃) δ 7.76 (m, 2H), 7.61 (d, J=8.2 Hz, 1H), 7.41 (ddd, J=7.2, 5.2, 2.6 Hz, 3H), 6.61 (tt, J=8.8, 2.3 Hz, 1H), 6.29 (d, J=9.5 Hz, 1H), 4.49 (ddd, J=9.3, 6.8, 2.6 Hz, 1H), 1.33 (d, J=6.8 Hz, 3H), 1.07 (s, J=6.2 Hz, 9H). MS (ESI) m/z=357.10 (M+H)⁺. LCMS Ret time (UV 214/254): 1.565 min.

Example 42: (R)—N²-(3-chloro-4-fluorophenyl)-N⁴-(1-cyclobutylpropyl)quinazoline-2,4-diamine

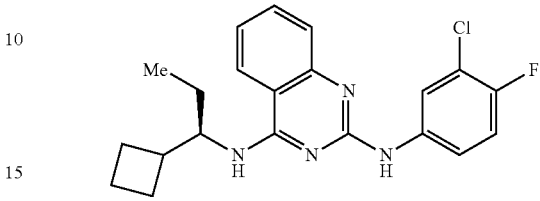

The title compound was obtained according to a procedure analogous to general procedure A, using (R)-1-cyclobutylethan-1-amine hydrochloride, which was prepared by a procedure analogous to general procedure B. ¹H NMR (400 MHz, CDCl₃) δ 8.09 (dd, J=6.6, 2.6 Hz, 1H), 7.77 (d, J=8.5 Hz, 1H), 7.73 (d, J=7.3 Hz, 1H), 7.64 (d, J=7.8 Hz, 1H), 7.38 (m, 2H), 7.14 (t, J=8.7 Hz, 1H), 6.43 (d, J=9.0 Hz, 1H), 4.40 (qd, J=8.9, 4.6 Hz, 1H), 2.59 (m, 1H), 2.12 (m, 1H), 2.01 (m, 1H), 1.84 (m, 6H), 1.53 (sept, J=7.6 Hz, 1H), 0.94 (t, J=7.4 Hz, 3H). MS (ESI) m/z=385.10 (M+H)⁺. LCMS Ret time (UV 214/254): 1.621 min.

Example 43: (R)—N²-(3-chloro-4-fluorophenyl)-N⁴-(1-cyclopentylethyl)quinazoline-2,4-diamine

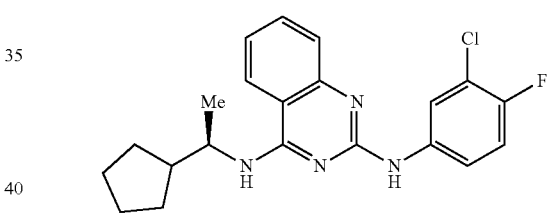

The title compound was obtained according to a procedure analogous to general procedure A, using (R)-1-cyclopentylethan-1-amine hydrochloride, which was prepared by a procedure analogous to general procedure B. ¹H NMR (400 MHz, CDCl₃) δ 8.11 (dd, J=6.6, 2.6 Hz, 1H), 7.73 (m, 2H), 7.62 (d, J=8.2 Hz, 1H), 7.39 (m, 2H), 7.13 (t, J=8.7 Hz, 1H), 6.31 (d, J=8.2 Hz, 1H), 4.36 (m, 1H), 2.11 (td, J=16.5, 8.4 Hz, 1H), 1.86 (m, 2H), 1.67 (ddd, J=11.2, 10.0, 4.2 Hz, 3H), 1.38 (d, J=6.5 Hz, 3H), 1.32 (m, 2H). MS (ESI) m/z=385.20 (M+H)⁺. LCMS Ret time (UV 214/254): 1.697 min.

Example 44: (R)—N²-(3-chloro-4-fluorophenyl)-N⁴-(1-cyclopentylpropyl)quinazoline-2,4-diamine

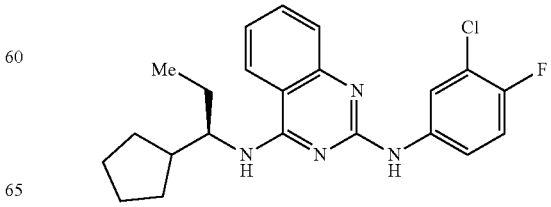

The title compound was obtained according to a procedure analogous to general procedure A, using (R)-1-cyclopentyl-propan-1-amine hydrochloride, which was prepared by a procedure analogous to general procedure B. ¹H NMR (400 MHz, CDCl₃) δ 8.08 (dd, J=6.6, 2.7 Hz, 1H), 7.72 (m, 2H), 7.66 (d, J=8.2 Hz, 1H), 7.38 (m, 2H), 7.12 (t, J=8.7 Hz, 1H), 6.28 (d, J=9.2 Hz, 1H), 4.33 (qd, J=8.7, 4.0 Hz, 1H), 2.13 (sext, J=8.1 Hz, 1H), 1.75 (m, 8H), 1.31 (m, 2H), 0.96 (t, J=7.4 Hz, 3H). MS (ESI) m/z=399.20 (M+H)⁺. LCMS Ret time (UV 214/254): 1.731 min.

Example 45: (S)—N²-(3-chloro-4-fluorophenyl)-N⁴-(1-cyclopropyl-2,2,2-trifluoroethyl)quinazoline-2,4-diamine

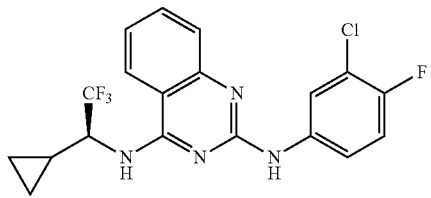

Step A: According to Liu et al. (J. Org. Chem. 1999, 64, 1278-1284), a 0.5 M solution of Ti(OEt)₄ (technical grade, □20% Ti; 2.097 mL, 10.00 mmol, 2 eq.) and cyclopropanecarbaldehyde (0.411 mL, 5.50 mmol, 1.1 equiv) in THF was prepared. Then, (R)-2-methylpropane-2-sulfinamide (606 mg, 5.00 mmol, 1 eq.) was added and the mixture was stirred at room temperature. Conversion was followed by TLC. Upon completion, the reaction was poured into an equal volume of brine with rapid stirring. The resulting suspension was filtered through a plug of Celite, and the filter cake was washed with CH₂Cl₂. The organic layer was washed with brine. The brine layer was extracted once with a small volume of CH₂Cl₂, and the combined organic portions were dried over MgSO₄, filtered, and concentrated. The crude was purified by silica gel chromatography (CH₂Cl₂) to provide (R,E)-N-(cyclopropylmethylene)-2-methylpropane-2-sulfinamide as a yellow oil (689 mg, 80%).

Step B. To a solution of (R,E)-N-(cyclopropylmethylene)-2-methylpropane-2-sulfinamide prepared by a procedure analogous to Step A (303 mg, 1.75 mmol, 1 eq.) and tetramethylammonium fluoride (196 mg, 2.10 mmol, 1.2 eq.) in CH₂Cl₂ (10 mL, 0.17M) at −55° C. was added TMSCF₃, (1.32 mL, 2.63 mmol, 1.5 eq.) via dropwise addition. The mixture was stirred at −55° C. for 2 h and then was warmed to room temperature with stirring overnight. When complete, the reaction mixture was quenched by the addition of saturated aqueous NH₄Cl and the aqueous layer was extracted with CH₂Cl₂. The combined organic layers were dried over MgSO₄, filtered, and concentrated. The diastereomers were separated by silica gel chromatography (0-2% MeOH in CH₂Cl₂) to provide the (R)—N—((S)-1-cyclopropyl-2,2,2-trifluoroethyl)-2-methylpropane-2-sulfinamide (274 mg, 65%). ¹H NMR (400 MHz, CDCl₃) δ 3.32 (br d, J=5.7 Hz, 1H), 2.93 (d quint, J=9.5, 6.7 Hz, 1H), 1.40 (d, J=6.8 Hz, 1H), 1.24 (s, J=3.3 Hz, 9H), 1.08 (dtt, J=9.6, 8.1, 4.8 Hz, 1H), 0.82 (tdd, J=8.2, 6.3, 4.7 Hz, 1H), 0.68 (m, 2H), 0.52 (m, 1H). MS (ESI) m/z=244.10 (M+H)⁺. LCMS Ret time (UV 214/254): 1.352 min.

Step C. To (R)—N—((S)-1-cyclopropyl-2,2,2-trifluoroethyl)-2-methylpropane-2-sulfinamide prepared by a procedure analogous to Step B (265 mg, 1.089 mmol, 1 eq.) was added 1:1 (v/v) MeOH (0.55 mL, 2 M) and 4 M HCl in dioxane solution (0.55 mL, 2 eq.). The mixture was stirred at room temperature for 30 min and was then concentrated to near dryness. Diethyl ether was added to precipitate the amine hydrochloride. The precipitate was then filtered off and washed with a 1:1 (v/v) mixture of diethyl ether and hexanes to provide (S)-1-cyclopropyl-2,2,2-trifluoroethan-1-amine as its hydrochloride salt (163 mg, 85%). ¹H NMR (400 MHz, DMSO) δ 9.29 (s, 3H), 3.58 (dq, J=10.1, 7.4 Hz, 1H), 1.07 (m, 1H), 0.66 (m, 4H).

Step D: The title compound was obtained according to a procedure analogous to general procedure A, using (S)-1-cyclopropyl-2,2,2-trifluoroethan-1-amine, which was prepared by a procedure analogous to Step C. ¹H NMR (400 MHz, CDCl₃) δ 7.80 (m, 2H), 7.76 (m, 2H), 7.45 (ddd, J=8.2, 7.0, 1.3 Hz, 1H), 7.31 (ddd, J=8.9, 4.1, 2.7 Hz, 1H), 7.12 (t, J=8.7 Hz, 1H), 6.74 (d, J=9.0 Hz, 1H), 4.36 (m, 1H), 1.27 (m, 1H), 0.91 (m, 1H), 0.68 (m, 2H), 0.35 (m, 1H). MS (ESI) m/z=411.00 (M+H)⁺. LCMS Ret time (UV 214/254): 1.466 min.

Example 46: (R)-8-bromo-N²-(3-chloro-4-fluorophenyl)-N-(1-cyclopropylethyl)quinazoline-2,4-diamine

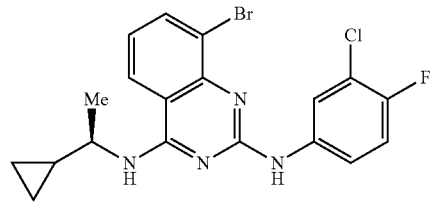 [SMILES: C[C@@H](Nc1nc(Nc2ccc(F)c(Cl)c2)nc2c(Br)cccc12)C1CC1]

Step A: A vial containing 2-amino-3-bromobenzoic acid (1.00 g, 4.63 mmol, 1.0 eq.) was heated to 160° C. Urea (2.78 g, 46.29 mmol, 10.0 eq.) was added in portions. After 12 h, more urea (2.78 g, 46.29 mmol, 10.0 eq.) was added in portions. The reaction mixture stirred for an additional 8 h. The mixture was then cooled to 100° C. and water (20 mL) was added. The resulting suspension was stirred for 1 h at 100° C. before being allowed to cool to room temperature. The light brown solid was then collected by filtration. The crude 8-bromoquinazoline-2,4(1H,3H)-dione was used without further purification (0.883 g, 79% yield). ¹H NMR (400 MHz, (CD₃)₂SO) δ 10.76 (br s, 2H), 7.93 (d, J=7.8 Hz, 2H), 7.13 (t, J=7.8 Hz, 1H). MS (ESI) m/z=241.10 (M+H)⁺. LCMS Ret time (UV 214/254): 0.866 min.

Step B: Phosphorus(V) oxychloride (4.8 mL, 51.86 mmol, 25.0 eq.) was slowly added to a flask containing 8-bromo-quinazoline-2,4(1H,3H)-dione (0.500 g, 2.07 mmol, 1.0 eq.). The mixture was heated to 100° C. and the progress of the reaction was monitored by TLC analysis (hexanes/EtOAc 2:1 v/v). Upon complete consumption of the starting material, the reaction mixture was cooled to room temperature and transferred portionwise to an Erlenmeyer flask containing crushed ice with the aid of CH₂Cl₂. The resulting mixture was stirred for 20 min and then extracted with CH₂Cl₂. The organic phases were combined, washed with saturated aqueous NaHCO₃ (3×40 mL), brine, dried over Na₂SO₄, and concentrated in vacuo. The crude solid was purified by silica gel chromatography to provide 8-bromo-2,4-dichloroquinazoline (0.377 g, 65% yield). ¹H NMR (400 MHz, CDCl₃) δ 8.29 (d, J=7.6 Hz, 1H), 8.26 (d, J=8.4 Hz, 1H), 7.60 (t, J=8.1 Hz, 1H). MS (ESI) m/z=275.00 (M+H)⁺. LCMS Ret time (UV 214/254): 1.511 min.

Step C: 8-Bromo-2,4-dichloroquinazoline (4.53 g, 16.30 mmol, 1.00 eq.) was dissolved in 2-propanol (60 mL). N,N-Diisopropylethylamine (3.55 mL, 20.37 mmol, 1.25 eq.) was added, followed by (R)-1-cyclopropylethylamine (1.58 mL, 17.11 mmol, 1.05 eq.). The reaction mixture was heated to 60° C. and the progress of the reaction was monitored by TLC analysis (hexanes/EtOAc 2:1 v/v). Upon complete consumption of the starting material, the reaction mixture was allowed to cool to room temperature and concentrated in vacuo. The residual oil was redissolved in EtOAc (300 mL) and treated with 50% aqueous NH₄Cl (200 mL). The layers were separated and the aqueous phase was extracted with EtOAc. The organic phases were combined, washed with brine, dried over Na₂SO₄, and concentrated in vacuo. The residue was purified by silica gel chromatography to provide (R)-8-bromo-2-chloro-N-(1-cyclopropylethyl)quinazolin-4-amine (5.12 g, 96% yield). ¹H NMR (400 MHz, CDCl₃) δ 8.02 (d, J=7.6 Hz, 1H), 7.67 (d, J=8.2 Hz, 1H), 7.29 (t, J=7.9 Hz, 1H), 5.95 (br d, J=6.2 Hz, 1H), 3.87 (sext, J=7.3 Hz, 1H), 1.38 (d, J=6.5 Hz, 3H), 0.99 (m, 1H), 0.61 (m, 1H), 0.52 (m, 1H), 0.46 (m, 1H), 0.37 (m, 1H). MS (ESI) m/z=328.00 (M+H)⁺. LCMS Ret time (UV 214/254): 1.704 min.

Step D: (R)-8-bromo-2-chloro-N-(1-cyclopropylethyl)quinazolin-4-amine (0.082 g, 0.251 mmol, 1.0 eq.) was dissolved in 2-propanol (1.25 mL). 3-Chloro-4-fluoroaniline (0.040 g, 0.276 mmol, 1.1 eq.) was added, followed by HCl (4.0 M solution in dioxane) (3 drops, cat.). The reaction mixture was heated to 180° C. for 40 min in a microwave reactor. The mixture was then concentrated in vacuo and purified by reverse phase preparative HPLC. The title compound was obtained as its corresponding trifluoroacetate salt (0.090 g, 65% yield). ¹H NMR (400 MHz, CD₃OD) δ 8.31 (d, J=8.2 Hz, 1H), 8.12 (d, J=7.7 Hz, 1H), 8.01 (d, J=5.0 Hz, 1H), 7.36 (3m ovlp, 3H), 3.83 (quint, J=7.7 Hz, 1H), 1.44 (d, J=6.6 Hz, 3H), 1.19 (m, 1H), 0.66 (m, 1H), 0.54 (m, 1H), 0.34 (m, 2H). MS (ESI) m/z=437.10 (M+H)⁺. LCMS Ret time (UV 214/254): 1.509 min.

Example 47: (R)-8-bromo-2-(3-chloro-4-fluorophenoxy)-N-(1-cyclopropylethyl)quinazolin-4-amine

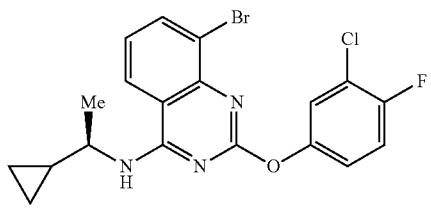 [SMILES: C[C@@H](Nc1nc(Oc2ccc(F)c(Cl)c2)nc2c(Br)cccc12)C1CC1]

(R)-8-bromo-2-chloro-N-(1-cyclopropylethyl)quinazolin-4-amine (0.100 g, 0.306 mmol, 1.00 eq.), which was prepared by a procedure analogous to Example 46, Step C, was dissolved in N,N-dimethylacetamide (1.0 mL). 3-Chloro-4-fluorophenol (0.056 g, 0.383 mmol, 1.25 eq.) was added, followed by potassium carbonate (0.106 g, 0.765 mmol, 2.50 eq.). The reaction mixture was heated to 180° C. for 30 min in a microwave reactor. The reaction mixture was then diluted with water (40 mL) and extracted with diethyl ether. The organic phases were combined, washed with brine, dried over Na₂SO₄, and concentrated in vacuo. The residue was purified by silica gel chromatography to provide (R)- 8-bromo-2-(3-chloro-4-fluorophenoxy)-N-(1-cyclopropylethyl)quinazolin-4-amine (0.128 g, 96% yield). ¹H NMR (400 MHz, CDCl₃) δ 7.96 (dd, J=7.6, 1.1 Hz, 1H), 7.63 (d, J=8.2 Hz, 1H), 7.45 (dd, J=6.2, 2.7 Hz, 1H), 7.15 (3m ovlp, 3H), 5.91 (d, J=7.1 Hz, 1H), 3.65 (sext, J=7.0 Hz, 1H), 1.29 (d, J=6.5 Hz, 3H), 0.96 (m, 1H), 0.57 (m, 1H), 0.48 (m, 1H), 0.33 (sext, J=4.8 Hz, 1H), 0.27 (sext, J=4.7 Hz, 1H). TLC Rf 0.41 (hexanes/EtOAc 3:1 v/v).

Example 48: (R)-8-bromo-N⁴-(1-cyclopropylethyl)-N²-(1H-pyrazol-3-yl)quinazoline-2,4-diamine

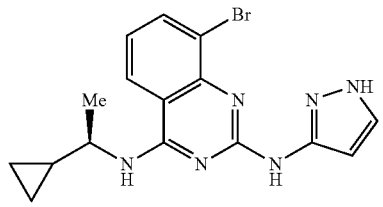 [SMILES: C[C@@H](Nc1nc(Nc2cc[nH]n2)nc2c(Br)cccc12)C1CC1]

(R)-8-bromo-2-chloro-N-(1-cyclopropylethyl)quinazolin-4-amine (0.050 g, 0.153 mmol, 1.00 eq.) was dissolved in dioxane (0.4 mL). 3-Aminopyrazole (0.016 g, 0.191 mmol, 1.25 eq.) was added, followed by HCl (4.0 M solution in dioxane) (3 drops, cat.). The reaction mixture was heated to 180° C. for 30 min in a microwave reactor. The reaction mixture was then transferred to a separatory funnel with the aid of CH₂Cl₂ (20 mL) and then treated with saturated aqueous NaHCO₃ (20 mL). The resulting biphasic mixture was separated and the aqueous layer was extracted with CH₂Cl₂. The organic layers were combined, washed with brine, dried over Na₂SO₄, and concentrated in vacuo. The residual solid was purified by silica gel chromatography to provide (R)-8-bromo-N⁴-(1-cyclopropylethyl)-N²-(1H-pyrazol-3-yl)quinazoline-2,4-diamine (0.042 g, 74% yield). ¹H NMR (400 MHz, CD₃OD) δ 8.04 (d, J=8.2 Hz, 1H), 7.92 (d, J=7.5 Hz, 1H), 7.42 (br s, 1H), 7.10 (t, J=7.6 Hz, 1H), 5.86 (br s, 1H), 3.92 (dq, J=12.4, 6.6 Hz, 1H), 1.38 (d, J=6.6 Hz, 3H), 1.13 (m, 1H), 0.58 (m, 1H), 0.47 (m, 2H), 0.29 (sext, J=4.7 Hz, 1H). MS (ESI) m/z=375.10 (M+H)⁺. LCMS Ret time (UV 214/254): 1.256 min.

Example 49: (R)-8-bromo-N⁴-(1-cyclopropylethyl)-N²-(oxazol-2-ylmethyl)quinazoline-2,4-diamine

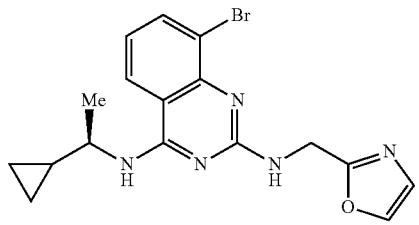 [SMILES: C[C@@H](Nc1nc(NCc2ncco2)nc2c(Br)cccc12)C1CC1]

(R)-8-bromo-2-chloro-N-(1-cyclopropylethyl)quinazolin-4-amine (0.200 g, 0.612 mmol, 1.00 eq.) was dissolved in 1-methyl-2-pyrrolidinone (1.0 mL). Oxazol-2-yl-methylamine hydrochloride (0.103 g, 0.765 mmol, 1.25 eq.) was added, followed by HCl (4.0 M solution in dioxane) (3 drops, cat.). The resulting mixture was heated to 150° C. and the progress of the reaction was monitored by LCMS. Upon complete consumption of the starting material, the mixture was allowed to cool to room temperature and diluted with CH$_2$Cl$_2$ (30 mL) and saturated aqueous NaHCO$_3$ (30 mL). The biphasic mixture was separated and the aqueous layer was extracted with CH$_2$Cl$_2$. The organic phases were combined, washed with brine, dried over Na$_2$SO$_4$, and concentrated in vacuo to give the title compound. MS (ESI) m/z=390.0 (M+H)$^+$. LCMS Ret time (UV 214/254): 1.149 min.

Example 50: (R)-8-(2-aminoethyl)-N$^2$-(3-chloro-4-fluorophenyl)-N$^4$-(1-cyclopropylpropyl)quinazoline-2,4-diamine

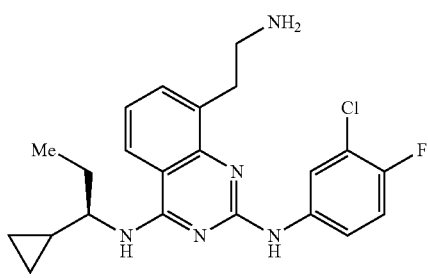 [SMILES: CC[C@@H](Nc1nc(Nc2ccc(F)c(Cl)c2)nc2c(CCN)cccc12)C1CC1]

(R)-8-bromo-N$^2$-(3-chloro-4-fluorophenyl)-N$^4$-(1-cyclopropylpropyl)quinazoline-2,4-diamine (0.200 g, 0.445 mmol, 1.00 eq.), which was prepared by a procedure analogous to the procedure used to prepare Example 46, potassium N-Boc-aminoethyltrifluoroborate (0.167 g, 0.667 mmol, 1.50 eq.), palladium(II) acetate (0.015 g, 0.067 mmol, 0.15 eq.), 2-dicyclohexylphosphino-2',6'-diisopropoxybiphenyl (RuPhos) (0.062 g, 0.133 mmol, 0.30 eq.) and potassium phosphate tribasic (0.283 g, 1.334 mmol, 3.00 eq.) were combined in a vial. The vial was sealed and subsequently evacuated/refilled with argon. The evacuation/refill cycle was repeated two additional times and then degassed 1,2-dimethoxyethane/water (5:2 v/v) (1.1 mL) was added. The reaction mixture was heated to 120° C. After 8 h, the reaction mixture was allowed to cool to room temperature and diluted with CH$_2$Cl$_2$ (15 mL) and saturated aqueous NH$_4$Cl (10 mL). The resulting biphasic mixture was passed through a phase separator and concentrated in vacuo. The residue was redissolved in CH$_2$Cl$_2$ (4 mL) and cooled to 0° C. Trifluoroacetic acid (1 mL) was added and the reaction mixture was allowed to warm to room temperature. The progress of the reaction was monitored by LCMS. Upon complete consumption of the starting material, the reaction mixture was concentrated in vacuo and purified by reverse phase preparative HPLC. The title compound was obtained as its corresponding trifluoroacetate salt (0.089 g, 38% yield over two steps). $^1$H NMR (400 MHz, CD$_3$OD) δ 8.26 (dd, J=8.3, 1.2 Hz, 1H), 7.97 (dd, J=6.7, 2.6 Hz, 1H), 7.79 (dd, J=7.4, 1.1 Hz, 1H), 7.47 (dd, J=8.2, 7.6 Hz, 1H), 7.40 (m, 1H), 7.27 (t, J=8.9 Hz, 1H), 3.70 (m, 1H), 3.34 (m, 2H), 3.24 (m, 2H), 1.88 (m, 2H) 1.16 (m, 1H), 1.01 (t, J=7.5 Hz, 3H), 0.70 (m, 1H), 0.49 (m, 1H), 0.36 (m, 1H), 0.27 (m, 1H). MS (ESI) m/z=414.10 (M+H)$^+$. LCMS Ret time (UV 214/254): 1.338 min.

Example 51: (R)-N$^2$-(3-chloro-4-fluorophenyl)-N$^4$-(1-cyclopropylpropyl)-8-(1,2,3,6-tetrahydropyridin-4-yl)quinazoline-2,4-diamine

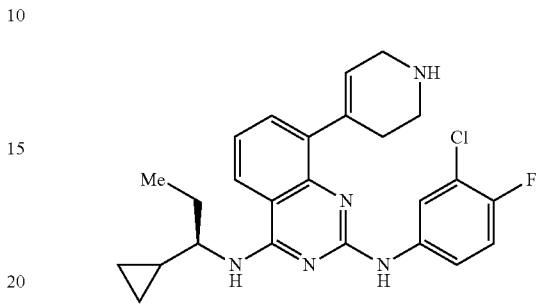

(R)-8-bromo-N$^2$-(3-chloro-4-fluorophenyl)-N$^4$-(1-cyclopropylpropyl)quinazoline-2,4-diamine (0.150 g, 0.334 mmol, 1.0 eq.), which was prepared by a procedure analogous to the procedure used to prepare Example 46, Step C, N-Boc-1,2,3,6-tetrahydropyridine-4-boronic acid pinacol ester (0.155 g, 0.500 mmol, 1.5 eq.), [1,1'-bis(diphenylphosphino)ferrocene]dichloropalladium(II) (0.024 g, 0.033 mmol, 0.1 eq.), and potassium carbonate (0.138 g, 1.001 mmol, 3.0 eq.) were combined in a vial. The vial was sealed and subsequently evacuated/refilled with argon. The evacuation/refill cycle was repeated two additional times and then degassed N,N-dimethylformamide/ethanol (4:1 v/v) (1.4 mL) was added. The mixture was heated to 90° C. and the progress of the reaction was monitored by LCMS. Upon complete consumption of the starting material, the reaction mixture was allowed to cool to room temperature and diluted with CH$_2$Cl$_2$ (15 mL) and saturated aqueous NH$_4$Cl (10 mL). The resulting biphasic mixture was passed through a phase separator and concentrated in vacuo. The residue was redissolved in CH$_2$Cl$_2$ (4 mL) and cooled to 0° C. Trifluoroacetic acid (1 mL) was added and the reaction mixture was allowed to warm to room temperature. The progress of the reaction was monitored by LCMS. Upon complete consumption of the starting material, the reaction mixture was concentrated in vacuo and purified by reverse phase preparative HPLC. The title compound was obtained as its corresponding trifluoroacetate salt (0.157 g, 83% yield over two steps). $^1$H NMR (400 MHz, CD$_3$OD) δ 8.28 (dd, J=8.3, 1.2 Hz, 1H), 7.91 (dd, J=6.6, 2.6 Hz, 1H), 7.71 (dd, J=7.5, 1.2 Hz, 1H), 7.51 (t, J=7.9 Hz, 1H), 7.38 (ddd, J=9.0, 4.1, 2.7 Hz, 1H), 7.28 (t, J=8.9 Hz, 1H), 6.00 (br s, 1H), 3.91 (br d, J=2.8 Hz, 2H), 3.67 (dt, J=9.1, 7.5 Hz, 1H), 3.61 (t, J=6.1 Hz, 2H), 2.75 (br m, 2H), 1.87 (m, 2H), 1.14 (m, 1H), 0.99 (t, J=7.4 Hz, 3H), 0.69 (m, 1H), 0.48 (m, 1H), 0.34 (sext, J=4.7 Hz, 1H), 0.27 (sext, J=4.9 Hz, 1H). MS (ESI) m/z=452.10 (M+H)$^+$. LCMS Ret time (UV 214/254): 1.376 min.

Example 52: (R)—N²-(3-chloro-4-fluorophenyl)-N⁴-(1-cyclopropylethyl)-8-(piperazin-1-yl)quinazoline-2,4-diamine

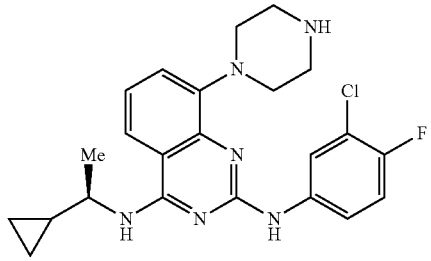 [SMILES: C[C@@H](Nc1nc(Nc2ccc(F)c(Cl)c2)nc2c(N3CCNCC3)cccc12)C1CC1]

(R)-8-bromo-N²-(3-chloro-4-fluorophenyl)-N⁴-(1-cyclopropylethyl)quinazoline-2,4-diamine (0.075 g, 0.172 mmol, 1.00 eq.), which was prepared by a procedure analogous to the procedure used to prepare Example 46, Step C, N-Boc-piperazine (0.035 g, 0.189 mmol, 1.10 eq.), palladium(II) acetate (0.004 g, 0.017 mmol, 0.10 eq.), 2,2'-bis(diphenylphosphino)-1,1'-binaphthalene ((±)-BINAP) (0.012 g, 0.019 mmol, 0.11 eq.) and sodium tert-butoxide (0.023 g, 0.241 mmol, 1.40 eq.) were combined in a vial. The vial was sealed and subsequently evacuated/refilled with argon. The evacuation/refill cycle was repeated two additional times and then degassed toluene (0.6 mL) was added. The reaction mixture was heated to 80° C. and the progress of the reaction was monitored by LCMS. Upon complete consumption of the starting material, the reaction mixture cooled to room temperature and diluted with CH₂Cl₂ (5 mL) and saturated aqueous NH₄Cl (5 mL). The resulting biphasic mixture was passed through a phase separator into a vial, which was then cooled to 0° C. Trifluoroacetic acid (1 mL) was added and the reaction mixture was allowed to warm to room temperature. The progress of the reaction was monitored by LCMS. Upon complete consumption of the starting material, the reaction mixture was concentrated in vacuo and purified by reverse phase preparative HPLC. The title compound was obtained as its corresponding trifluoroacetate salt (0.072 g, 75% yield over two steps). ¹H NMR (400 MHz, CD₃OD) δ 8.15 (dd, J=8.3, 1.0 Hz, 1H), 8.00 (dd, J=6.6, 2.6 Hz, 1H), 7.81 (dd, J=7.8, 1.0 Hz, 1H), 7.51 (t, J=8.1 Hz, 1H), 7.40 (m, 1H), 7.31 (t, J=8.7 Hz, 1H), 3.84 (m, 1H), 3.59 (br s, 4H), 3.25 (br m, 4H), 1.45 (d, J=6.7 Hz, 3H) 1.20 (m, 1H), 0.66 (m, 1H), 0.54 (m, 1H), 0.33 (m, 2H). MS (ESI) m/z=441.10 (M+H)⁺. LCMS Ret time (UV 214/254): 1.224 min.

Example 53: (R)—N²-(3-chloro-4-fluorophenyl)-N⁴-(1-cyclopropylethyl)-N⁸-(3-(dimethylamino)propyl)quinazoline-2,4,8-triamine

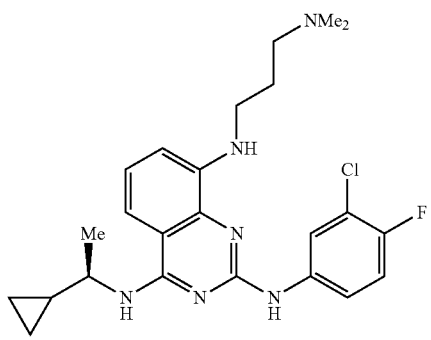 [SMILES: C[C@@H](Nc1nc(Nc2ccc(F)c(Cl)c2)nc2c(NCCCN(C)C)cccc12)C1CC1]

(R)-8-bromo-N²-(3-chloro-4-fluorophenyl)-N⁴-(1-cyclopropylethyl)quinazoline-2,4-diamine (0.060 g, 0.138 mmol, 1.0 eq.), 1,1-dimethyl-1,3-diaminopropane (0.52 mL, 4.131 mmol, 30.0 eq.), which was prepared by a procedure analogous to the procedure used to prepare Example 46, Step C, palladium(II) acetate (0.003 g, 0.014 mmol, 0.1 eq.), 2,2'-bis(diphenylphosphino)-1,1'-binaphthalene ((±)-BINAP) (0.009 g, 0.014 mmol, 0.1 eq.) and sodium tert-butoxide (0.040 g, 0.413 mmol, 3.0 eq.) were combined in a vial. The vial was sealed and subsequently evacuated/refilled with argon. Degassed dioxane (0.08 mL) was then added. The reaction mixture was heated to 150° C. for 30 min in a microwave reactor. The mixture was then diluted with EtOAc (25 mL) and filtered over Celite. The filtrate was washed with water, brine, dried over Na₂SO₄, and concentrated in vacuo. The residue was purified by reverse phase preparative HPLC. The title compound was obtained as its corresponding trifluoroacetate salt (0.028 g, 36% yield). ¹H NMR (400 MHz, CD₃OD) δ 8.03 (dd, J=6.7, 2.7 Hz, 1H), 7.57 (dd, J=8.2, 0.9 Hz, 1H), 7.41 (ddd, J=8.9, 4.0, 2.7 Hz, 1H), 7.33 (t, J=8.1 Hz, 1H), 7.25 (t, J=8.9 Hz, 1H), 7.09 (d, J=8.0 Hz, 1H), 3.84 (dq, J=12.4, 6.7 Hz, 1H), 3.37 (m, 2H), 2.92 (s, 6H), 2.19 (m, 2H), 1.44 (d, J=6.7 Hz, 3H), 1.19 (m, 1H), 0.65 (m, 1H), 0.53 (m, 1H), 0.33 (m, 2H). MS (ESI) m/z=457.20 (M+H)⁺. LCMS Ret time (UV 214/254): 1.435 min.

Example 54: (R)-2-((2-((3-chloro-4-fluorophenyl)amino)-4-((1-cyclopropylethyl)amino)quinazolin-8-yl)amino)ethan-1-ol

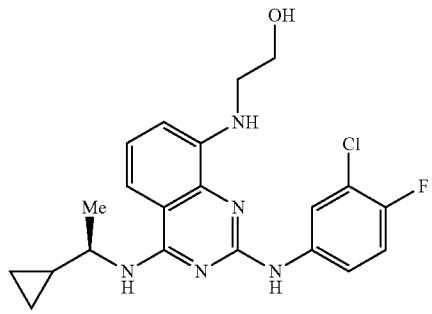 [SMILES: C[C@@H](Nc1nc(Nc2ccc(F)c(Cl)c2)nc2c(NCCO)cccc12)C1CC1]

(R)-8-bromo-N²-(3-chloro-4-fluorophenyl)-N⁴-(1-cyclopropylethyl)quinazoline-2,4-diamine (0.100 g, 0.229 mmol, 1.0 eq.), 2-amino-1-ethanol (0.28 mL, 4.590 mmol, 20.0 eq.), and copper(II) sulfate (0.037 g, 0.229 mmol, 1.0 eq.) were combined in a vial. The vial was sealed and subsequently evacuated/refilled with argon. The evacuation/refill cycle was repeated two additional times and then degassed 1-methyl-2-pyrrolidinone (0.23 mL) was added. The reaction mixture was heated to 110° C. and the progress of the reaction was monitored by LCMS. Upon complete consumption of the starting material, the mixture was allowed to cool to room temperature. Water (30 mL) was added and the resulting mixture was extracted with EtOAc. The organic phases were combined, washed with water, brine, dried over Na₂SO₄, and concentrated in vacuo. The residue was purified first by silica gel chromatography and then by reverse phase preparative HPLC. The title compound was obtained as its corresponding trifluoroacetate salt (0.037 g, 30% yield). ¹H NMR (400 MHz, CD₃OD) δ 7.98 (dd, J=6.7, 2.6 Hz, 1H), 7.57 (d, J=8.1 Hz, 1H), 7.38 (ddd, J=8.9, 4.1, 2.7 Hz, 1H), 7.32 (t, J=8.1 Hz, 1H), 7.26 (t, J=8.9 Hz, 1H), 7.12

(d, J=7.9 Hz, 1H), 3.88 (t, J=5.7 Hz, 2H), 3.82 (dq, J=12.7, 6.8 Hz, 1H), 3.35 (t, J=5.7 Hz, 2H), 1.43 (d, J=6.7 Hz, 3H), 1.18 (m, 1H), 0.64 (m, 1H), 0.52 (m, 1H), 0.32 (m, 2H). MS (ESI) m/z=416.20 (M+H)⁺. LCMS Ret time (UV 214/254): 1.534 min.

Example 55: (R)-2-((3-chloro-4-fluorophenyl)amino)-4-((1-cycloprprpylethyl)amino)quinazoline-8-carbonitrile

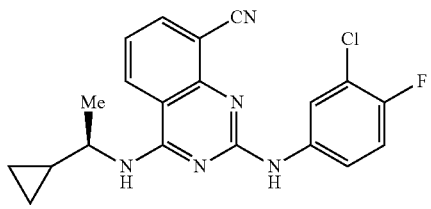 [SMILES: C[C@@H](Nc1nc(Nc2ccc(F)c(Cl)c2)nc2c(C#N)cccc12)C1CC1]

(R)-8-bromo-N²-(3-chloro-4-fluorophenyl)-N⁴-(1-cyclopropylethyl)quinazoline-2,4-diamine (0.500 g, 1.147 mmol, 1.0 eq.), which was prepared by a procedure analogous to Example 46, and copper(I) cyanide (0.617 g, 6.885 mmol, 6.0 eq.) were suspended in 1-methyl-2-pyrrolidinone (4.0 mL). The mixture was heated to 150° C. and the progress of the reaction was monitored by LCMS. Upon complete consumption of the starting material, the mixture was allowed to cool to room temperature. EtOAc (50 mL) and saturated aqueous NH₄Cl/NH₄OH (9:1 v/v) (50 mL) were then added and the resulting biphasic mixture stirred vigorously for 30 min before being filtered over a plug of cotton. The layers of the filtrate were separated and the aqueous phase was extracted with EtOAc. The organic phases were combined, washed with brine, dried over Na₂SO₄, and concentrated in vacuo. The residue was purified by silica gel chromatography to provide (R)-2-((3-chloro-4-fluorophenyl)amino)-4-((1-cyclopropylethyl)amino)quinazoline-8-carbonitrile (0.396 g, 90% yield). ¹H NMR (400 MHz, CD₃OD) δ 8.52 (d, J=8.2 Hz, 1H), 8.17 (d, J=7.6 Hz, 1H), 8.02 (br d, J=3.7 Hz, 1H), 7.52 (t, J=7.8 Hz, 1H), 7.42 (br s, 1H), 7.27 (t, J=8.9 Hz, 1H), 3.83 (m, 1H), 1.43 (d, J=6.6 Hz, 3H), 1.18 (m, 1H), 0.66 (m, 1H), 0.53 (m, 1H), 0.34 (m, 2H). MS (ESI) m/z=382.00 (M+H)⁺. LCMS Ret time (UV 214/254): 1.488 min.

Example 56: (R)-8-(aminomethyl)-N²-(3-chloro-4-fluorophenyl)-N⁴-(1-cyclopropylethyl)quinazoline-2,4-diamine

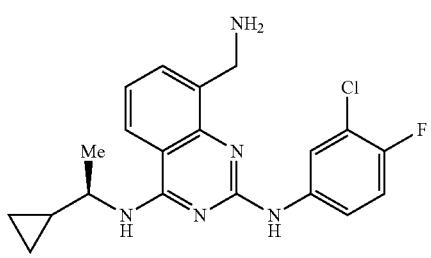 [SMILES: C[C@@H](Nc1nc(Nc2ccc(F)c(Cl)c2)nc2c(CN)cccc12)C1CC1]

Zinc(II) Chloride (0.022 g, 0.164 mmol, 1.1 eq.) was suspended in THF (0.2 mL). Lithium borohydride (2.0 M solution in THF) (0.164 mL, 0.328 mmol, 2.2 eq.) was added and the mixture heated to 50° C. After 50 min, a solution of (R)-2-((3-chloro-4-fluorophenyl)amino)-4-((1-cyclopropylethyl)amino)quinazoline-8-carbonitrile trifluoroacetate (0.074 g, 0.149 mmol, 1.0 eq.), which was prepared by a procedure analogous to the procedure used to prepare Example 55, in THF (0.4+0.4 mL) was added. The temperature was increased to 60° C. and the progress of the reaction was monitored by LCMS. After 18 h, a second portion of Zn(BH₄)₂ (0.082 mmol)—prepared as above—was added. After an additional 3 h, the reaction mixture was allowed to cool to room temperature and quenched by the dropwise addition of water (15 mL). When the effervescence had ceased, the mixture was extracted with CH₂Cl₂. The organic phases were combined, washed with brine, passed through a phase separator, and concentrated in vacuo. The residue was purified by reverse phase preparative HPLC. The title compound was obtained as its corresponding trifluoroacetate salt (0.037 g, 50% yield). ¹H NMR (400 MHz, CD₃OD) δ 8.34 (m, 1H), 8.04 (m, 1H), 7.90 (m, 1H), 7.47 (2m ovlp, 2H), 7.26 (t, J=8.8 Hz, 1H), 4.53 (s, 2H), 3.85 (m, 1H), 1.44 (d, J=6.7 Hz, 3H), 1.19 (m, 1H), 0.65 (m, 1H), 0.53 (m, 1H), 0.32 (m, 2H). MS (ESI) m/z=386.10 (M+H)⁺. LCMS Ret time (UV 214/254): 1.266 min.

Example 57: (R)-2-((3-chloro-4-fluorophenyl)amino)-4-((1-cyclopropylethyl)amino)quinazoline-8-carboximidamide

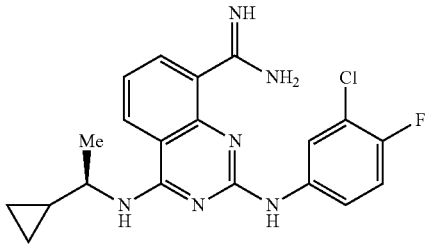 [SMILES: C[C@@H](Nc1nc(Nc2ccc(F)c(Cl)c2)nc2c(C(=N)N)cccc12)C1CC1]

Ammonium chloride (0.024 g, 0.440 mmol, 2.1 eq.) was suspended in toluene (0.15 mL) and the mixture was cooled to 0° C. Trimethyl aluminum (2.0 M solution in toluene) (0.210 mL, 0.419 mmol, 2.0 eq.) was added and the mixture was allowed to warm to room temperature. After 30 min, a solution of (R)-2-((3-chloro-4-fluorophenyl)amino)-4-((1-cyclopropylethyl)amino)quinazoline-8-carbonitrile (0.080 g, 0.210 mmol, 1.0 eq.), which was prepared by a procedure analogous to the procedure used to prepare Example 55, in THF/toluene (1:1 v/v) (0.4+0.4 mL) was added. The temperature was increased to 80° C. and the progress of the reaction was monitored by LCMS. After 18 h, a second portion of MeAl(C₁)NH₂ (0.419 mmol)—prepared as above—was added and the temperature increased to 100° C. After an additional 2 h, a final portion of MeAl(Cl)NH₂ (1.68 mmol) was added. Two hours later, the reaction mixture was cooled to 0° C., poured into a slurry of SiO₂ in CH₂Cl₂/MeOH (2:1 v/v) (45 mL), and stirred overnight. The mixture was then filtered and concentrated in vacuo. The residue was purified by reverse phase preparative HPLC. The title compound was obtained as its corresponding trifluoroacetate salt (0.037 g, 34% yield). ¹H NMR (400 MHz, CD₃OD) δ 8.47 (dd, J=8.2, 1.1 Hz, 1H), 8.17 (dd, J=7.6, 1.1 Hz, 1H), 8.03 (dd, J=6.7, 2.6 Hz, 1H), 7.43 (t, J=7.9 Hz, 1H), 7.39 (ddd, J=9.0, 3.9, 2.8 Hz, 1H), 7.23 (t, J=8.9 Hz, 1H), 3.89 (dq, J=12.4, 6.7 Hz, 1H), 1.44 (d, J=6.7

Hz, 3H), 1.18 (m, 1H), 0.64 (m, 1H), 0.52 (m, 1H), 0.39 (sext, J=4.9 Hz, 1H), 0.32 (sext, J=4.9 Hz, 1H). MS (ESI) m/z=400.00 (M+H)$^+$. LCMS Ret time (UV 214/254): 1.280 min.

Example 58: (R)—N$^2$-(3-chloro-4-fluorophenyl)-N$^4$-(1-cyclopropylethyl)-8-((methylamino)methyl)quinazoline-2,4-diamine

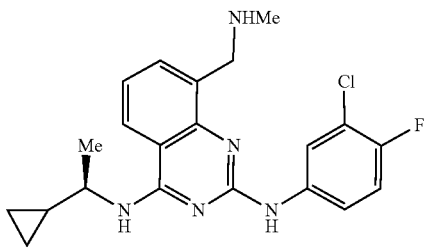 [SMILES: CNCc1cccc2c(N[C@H](C)C3CC3)nc(Nc3ccc(F)c(Cl)c3)nc12]

Step A: (R)-2-((3-chloro-4-fluorophenyl)amino)-4-((1-cyclopropylethyl)amino)quinazoline-8-carbonitrile (0.198 g, 0.519 mmol, 1.0 eq.), which was prepared by a procedure analogous to the procedure used to prepare Example 55, was dissolved in THF (2.6 mL) and the solution cooled to −78° C. Diisobutylaluminum hydride (1.0 M solution in toluene) (2.33 mL, 2.333 mmol, 4.5 eq.) was added dropwise. The mixture was allowed to warm to room temperature and the progress of the reaction was monitored by LCMS. After 90 min, the mixture was recooled to −78° C. and quenched with 50% aqueous potassium sodium tartrate (25 mL). EtOAc (10 mL) was added and the mixture was allowed to warm to room temperature. After stirring vigorously for 2 h, the layers were separated and the aqueous phase was extracted with EtOAc. The organic phases were combined, washed with brine, dried over Na$_2$SO$_4$, and concentrated in vacuo to give (R)-2-((3-chloro-4-fluorophenyl)amino)-4-((1-cyclopropylethyl)amino)quinazoline-8-carbaldehyde, which was used without further purification.

Step B: (R)-2-((3-chloro-4-fluorophenyl)amino)-4-((1-cyclopropylethyl)amino)quinazoline-8-carbaldehyde, prepared by a procedure analogous to Step A, (0.519 mmol, 1.0 eq.) and methylamine hydrochloride (0.875 g, 12.964 mmol, 25.0 eq.) were dissolved in methanol (5 mL). NaBH$_3$CN (0.163 g, 2.593 mmol, 5.0 eq.) was added and the progress of the reaction was monitored by LCMS. After 14 h, the mixture was heated to 50° C. and more NaBH$_3$CN (0.163 g, 2.593 mmol) was added. After an additional 6 h, the reaction mixture was allowed to cool to room temperature, diluted with water (40 mL), and extracted with EtOAc. The organic phases were combined, washed with brine, dried over Na$_2$SO$_4$, and concentrated in vacuo. The residue was purified by reverse phase preparative HPLC. The title compound was obtained as its corresponding trifluoroacetate salt (0.080 g, 30% yield over two steps). $^1$H NMR (400 MHz, CD$_3$OD) δ 8.38 (dd, J=8.3, 1.0 Hz, 1H), 8.01 (dd, J=6.7, 2.6 Hz, 1H), 7.94 (d, J=7.4 Hz, 1H), 7.51 (t, J=7.8 Hz, 1H), 7.43 (ddd, J=9.0, 4.0, 2.7 Hz, 1H), 7.21 (t, J=9.0 Hz, 1H), 4.59 (m, 2H), 3.84 (dq, J=12.5, 6.7 Hz, 1H), 2.92 (s, 3H), 1.45 (d, J=6.7 Hz, 3H), 1.20 (m, 1H), 0.66 (m, 1H), 0.53 (m, 1H), 0.33 (m, 2H). MS (ESI) m/z=400.10 (M+H)$^+$. LCMS Ret time (UV 214/254): 1.281 min.

Example 59: (R)-1-((2-((3-chloro-4-fluorophenyl)amino)-4-((1-cyclopropylethyl)amino)quinazolin-8-yl)methyl)guanidine

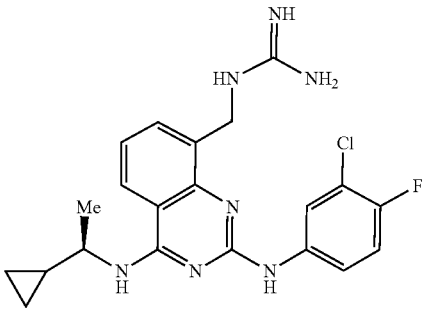 [SMILES: C[C@@H](Nc1nc(Nc2ccc(F)c(Cl)c2)nc2c(CNC(=N)N)cccc12)C1CC1]

(R)-8-(aminomethyl)-N$^2$-(3-chloro-4-fluorophenyl)-N$^4$-(1-cyclopropylethyl)quinazoline-2,4-diamine (0.164 g, 0.424 mmol, 1.0 eq.), which was prepared by a procedure analogous to the procedure used to prepare Example 56, was dissolved in N,N-dimethylformamide (1.5 mL). N,N-Diisopropylethylamine (0.081 mL, 0.466 mmol, 1.1 eq.) was added, followed by 1H-pyrazole-1-carboxamidine hydrochloride (0.068 g, 0.466 mmol, 1.1 eq.). The progress of the reaction was monitored by LCMS. After 16 h, the mixture was concentrated in vacuo and purified by reverse phase preparative HPLC. The title compound was obtained as its corresponding trifluoroacetate salt (0.065 g, 28% yield). $^1$H NMR (400 MHz, CD$_3$OD) δ 8.29 (d, J=8.3 Hz, 1H), 8.00 (m, 1H), 7.83 (d, J=7.5 Hz, 1H), 7.51 (t, J=7.9 Hz, 1H), 7.42 (m, 1H), 7.27 (m, 1H), 4.74 (s, 2H), 3.84 (m, 1H), 1.45 (d, J=6.7 Hz, 3H), 1.20 (m, 1H), 0.66 (m, 1H), 0.53 (m, 1H), 0.32 (m, 2H). MS (ESI) m/z=428.10 (M+H)$^+$. LCMS Ret time (UV 214/254): 1.248 min.

Example 60: (R)-8-(2-aminoethyl)-N$^2$-(3-chloro-4-fluorophenyl)-N$^4$-(1-cyclopropylethyl)quinazoline-2,4-diamine The title compound was prepared according to a procedure analogous to general procedure E, using (R)-8-bromo-N$^2$-(3-chloro-4-fluorophenyl)-N$^4$-(1-cyclopropylethyl)quinazoline-2,4-diamine, which was prepared according to a procedure analogous to general procedure A. $^1$H NMR (400 MHz, CD$_3$OD) δ 8.25 (d, J=8.2 Hz, 1H), 8.01 (dd, J=6.5, 2.4 Hz, 1H), 7.78 (d, J=7.4 Hz, 1H), 7.47 (t, J=8.0 Hz, 1H), 7.42 (m, 1H), 7.30 (m, 1H), 3.85 (m, 1H), 3.34 (m, 2H), 3.25 (m, 2H), 1.45 (d, J=6.7 Hz, 3H), 1.20 (m, 1H), 0.66 (m, 1H), 0.54 (m, 1H), 0.33 (m, 2H). MS (ESI) m/z=400.20 (M+H)$^+$. LCMS Ret time (UV 214/254): 1.330 min.

Example 61: (R)-8-(azetidin-3-yl)-N²-(3-chloro-4-fluorophenyl)-N⁴-(1-cyclopropylethyl)quinazoline-2,4-diamine

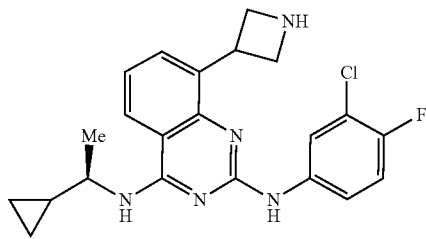 [SMILES: C[C@@H](Nc1nc(Nc2ccc(F)c(Cl)c2)nc2c(C3CNC3)cccc12)C1CC1]

The title compound was prepared according to a procedure analogous to general procedure E, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.22 (m, 1H), 8.03 (m, 1H), 7.91 (m, 1H), 7.48 (m, 1H), 7.39 (m, 1H), 7.27 (m, 1H), 4.71 (m, 1H), 4.62 (m, 2H), 4.39 (t, J=7.9 Hz, 2H), 3.86 (m, 1H), 1.43 (d, J=6.7 Hz, 3H), 1.18 (m, 1H), 0.65 (m, 1H), 0.52 (m, 1H), 0.33 (m, 2H). MS (ESI) m/z=412.10 (M+H)⁺. LCMS Ret time (UV 214/254): 1.281 min.

Example 62: (R)—N²-(3-chloro-4-fluorophenyl)-N⁴-(1-cyclopropylethyl)-8-(1,2,3,6-tetrahydropyridin-4-yl)quinazoline-2,4-diamine

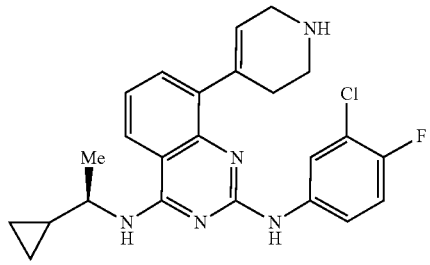 [SMILES: C[C@@H](Nc1nc(Nc2ccc(F)c(Cl)c2)nc2c(C3=CCNCC3)cccc12)C1CC1]

The title compound was prepared according to a procedure analogous to general procedure F, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.27 (dd, J=8.2, 1.4 Hz, 1H), 7.95 (dt, J=6.7, 2.5 Hz, 1H), 7.70 (dd, J=7.4, 1.4 Hz, 1H), 7.51 (td, J=8.0, 2.6 Hz, 1H), 7.39 (m, 1H), 7.29 (td, J=8.8, 2.5 Hz, 1H), 6.00 (br s, 1H), 3.91 (br s, 2H), 3.82 (m, 1H), 3.60 (m, 2H), 2.75 (br s, 2H), 1.44 (dd, J=6.5, 2.5 Hz, 3H), 1.18 (m, 1H), 0.66 (m, 1H), 0.52 (m, 1H), 0.32 (m, 2H). MS (ESI) m/z=438.10 (M+H)⁺. LCMS Ret time (UV 214/254): 1.349 min.

Example 63: (R)—N²-(2-(1H-imidazol-4-yl)ethyl)-N⁴-(1-cyclopropylethyl)-8-(1,2,3,6-tetrahydropyridin-4-yl)quinazoline-2,4-diamine

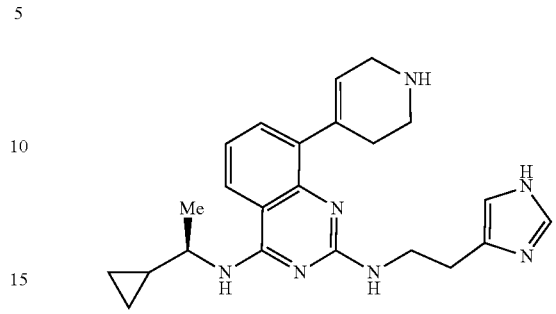

The title compound was prepared using general procedure F, using (R)—N²-(2-(1H-imidazol-4-yl)ethyl)-8-bromo-N⁴-(1-cyclopropylethyl)quinazoline-2,4-diamine, which was prepared according to a procedure analogous to general procedure A. ¹H NMR (400 MHz, CD₃OD) δ 8.81 (d, J=1.4 Hz, 1H), 8.23 (dd, J=8.2, 1.3 Hz, 1H), 7.63 (dd, J=7.4, 1.2 Hz, 1H), 7.44 (t, J=8.0 Hz, 1H), 7.39 (br s, 1H), 5.93 (br m, 1H), 3.95 (m, 1H), 3.85 (m, 4H), 3.57 (t, J=6.2 Hz, 2H), 3.10 (t, J=6.5 Hz, 2H), 2.68 (br d, J=2.0 Hz, 2H), 1.44 (d, J=6.7 Hz, 3H), 1.20 (m, 1H), 0.66 (m, 1H), 0.57 (m, 1H), 0.38 (m, 2H). MS (ESI) m/z=404.20 (M+H)⁺. LCMS Ret time (UV 214/254): 0.869 min.

Example 64: (R)—N²-(3-chloro-4-fluorophenyl)-N⁴-(1-cyclopropylpropyl)-8-(piperazin-1-yl)quinazoline-2,4-diamine

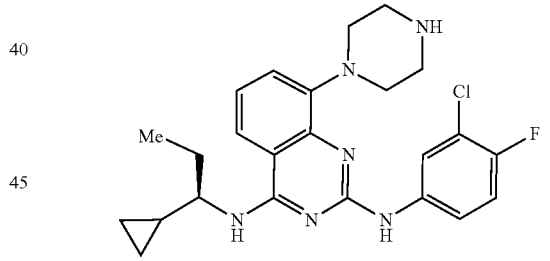

The title compound was prepared according to a procedure analogous to general procedure G, using (R)-8-bromo-N²-(3-chloro-4-fluorophenyl)-N⁴-(1-cyclopropylpropyl)quinazoline-2,4-diamine, which was prepared by a procedure analogous to general procedure A using (R)-1-cyclopropylpropan-1-amine hydrochloride, which was prepared by a procedure analogous to the procedure used to prepare Example 46, Step C. ¹H NMR (400 MHz, CD₃OD) δ 8.16 (dd, J=8.2, 0.8 Hz, 1H), 7.97 (dd, J=6.6, 2.6 Hz, 1H), 7.82 (dd, J=7.8, 0.7 Hz, 1H), 7.51 (t, J=8.1 Hz, 1H), 7.39 (m, 1H), 7.31 (t, J=8.8 Hz, 1H), 3.70 (m, 1H), 3.58 (br s, 4H), 3.25 (br m, 4H), 1.88 (m, 2H), 1.15 (m, 1H), 1.01 (t, J=7.5 Hz, 3H), 0.70 (m, 1H), 0.49 (m, 1H), 0.36 (m, 1H), 0.29 (m, 1H). MS (ESI) m/z=455.10 (M+H)⁺. LCMS Ret time (UV 214/254): 1.274 min.

Example 65: (R)—N⁸-(2-aminoethyl)-N²-(3-chloro-4-fluorophenyl)-N⁴-(1-cyclopropylethyl)quinazoline-2,4,8-triamine

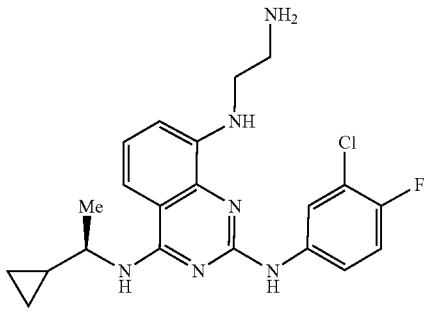 [SMILES: C[C@@H](Nc1nc(Nc2ccc(F)c(Cl)c2)nc2c(NCCN)cccc12)C1CC1]

The title compound was prepared according to a procedure analogous to general procedure I, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.04 (dd, J=6.8, 2.7 Hz, 1H), 7.68 (d, J=8.1 Hz, 1H), 7.45 (ddd, J=9.0, 4.0, 2.8 Hz, 1H), 7.36 (t, J=8.0 Hz, 1H), 7.26 (t, J=8.9 Hz, 1H), 7.18 (d, J=7.8 Hz, 1H), 3.86 (dq, J=12.5, 6.8 Hz, 1H), 3.54 (dd, J=7.0, 5.1 Hz, 2H), 3.35 (dd, J=7.2, 5.2 Hz, 2H), 1.44 (d, J=6.7 Hz, 3H), 1.19 (m, 1H), 0.66 (m, 1H), 0.53 (m, 1H), 0.33 (m, 2H). MS (ESI) m/z=415.10 (M+H)⁺. LCMS Ret time (UV 214/254): 1.354 min.

Example 66: (R)—N⁸-(3-aminopropyl)-N²-(3-chloro-4-fluorophenyl)-N⁴-(1-cyclopropylethyl)quinazoline-2,4,8-triamine

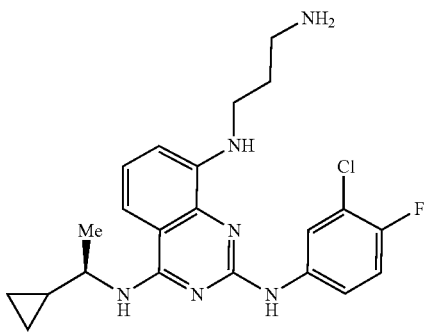

The title compound was prepared according to a procedure analogous to general procedure H using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.02 (dd, J=6.5, 2.5 Hz, 1H), 7.58 (d, J=8.2 Hz, 1H), 7.41 (ddd, J=9.1, 4.0, 2.7 Hz, 1H), 7.34 (t, J=8.1 Hz, 1H), 7.26 (td, J=8.9, 2.8 Hz, 1H), 7.11 (d, J=8.0 Hz, 1H), 3.85 (dq, J=12.4, 6.8 Hz, 1H), 3.39 (t, J=6.4 Hz, 2H), 3.20 (t, J=7.2 Hz, 2H), 2.14 (quint, J=6.8 Hz, 2H), 1.44 (d, J=6.7 Hz, 3H), 1.19 (m, 1H), 0.65 (m, 1H), 0.53 (m, 1H), 0.33 (m, 2H). MS (ESI) m/z=429.10 (M+H)⁺. LCMS Ret time (UV 214/254): 1.348 min.

Example 67: (R)—N²-(3-chloro-4-fluorophenyl)-N⁴-(1-cyclopropylethyl)-N8-(2-(dimethylamino)ethyl)quinazoline-2,4,8-triamine

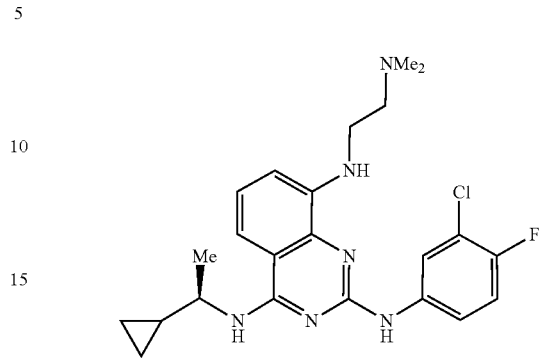

The title compound was prepared according to a procedure analogous to general procedure H using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.03 (dd, J=6.7, 2.7 Hz, 1H), 7.69 (d, J=8.2 Hz, 1H), 7.43 (ddd, J=9.0, 3.9, 2.7 Hz, 1H), 7.37 (t, J=8.1 Hz, 1H), 7.26 (t, J=8.9 Hz, 1H), 7.22 (d, J=8.0 Hz, 1H), 3.85 (dq, J=12.6, 6.7 Hz, 1H), 3.68 (t, J=5.3 Hz, 2H), 3.55 (t, J=6.0 Hz, 2H), 2.99 (s, 6H), 1.44 (d, J=6.7 Hz, 3H), 1.20 (m, 1H), 0.66 (m, 1H), 0.53 (m, 1H), 0.33 (m, 2H). MS (ESI) m/z=443.10 (M+H)⁺. LCMS Ret time (UV 214/254): 1.424 min.

Example 68: (R)-8-(aminomethyl)-N²-(3-chloro-4-fluorophenyl)-N⁴-(1-cyclopropylpropyl)quinazoline-2,4-diamine

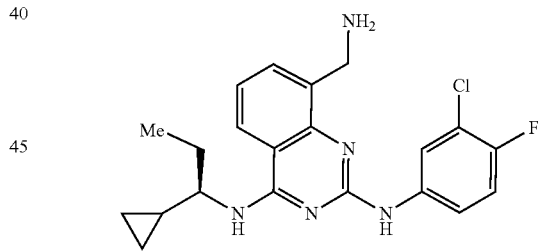

Step A: (R)-2-((3-chloro-4-fluorophenyl)amino)-4-((1-cyclopropylpropyl)amino)quinazoline-8-carbonitrile was prepared by a procedure analogous to general procedure J, using (R)-8-bromo-N²-(3-chloro-4-fluorophenyl)-N⁴-(1-cyclopropylpropyl)quinazoline-2,4-diamine, which was prepared by a procedure analogous to general procedure A using (R)-1-cyclopropylpropan-1-amine hydrochloride, which was prepared by a procedure analogous to the procedure used to prepare Example 46, Step C.

Step B: The title compound was prepared according to procedures analogous to general procedure K, using (R)-2-((3-chloro-4-fluorophenyl)amino)-4-((1-cyclopropylpropyl)amino)quinazoline-8-carbonitrile. ¹H NMR (400 MHz, CD₃OD) δ 8.39 (d, J=8.2 Hz, 1H), 7.98 (dd, J=6.7, 2.6 Hz, 1H), 7.95 (d, J=7.4 Hz, 1H), 7.54 (t, J=8.0 Hz, 1H), 7.43 (ddd, J=8.9, 4.1, 2.7 Hz, 1H), 7.28 (t, J=8.9 Hz, 1H), 4.55 (s, 2H), 3.71 (dt, J=9.1, 7.3 Hz, 1H), 1.88 (m, 2H), 1.16 (m, 1H), 1.01 (t, J=7.5 Hz, 3H), 0.70 (m, 1H), 0.49 (m, 1H), 0.36 (sext, J=4.8 Hz, 1H), 0.27 (sext, J=4.8 Hz, 1H). MS (ESI) m/z=400.00 (M+H)⁺. LCMS Ret time (UV 214/254): 1.280 min.

Example 69: (R)-2-(3-chloro-4-fluorophenoxy)-N-(1-cyclopropylethyl)-8-(1,2,3,6-tetrahydropyridin-4-yl)quinazolin-4-amine

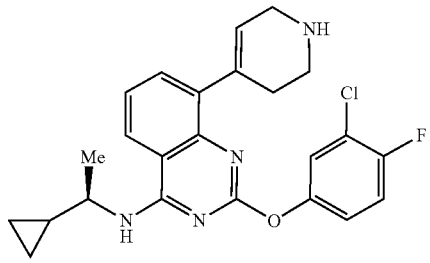 [SMILES: C[C@@H](Nc1nc(Oc2ccc(F)c(Cl)c2)nc2c(C3=CCNCC3)cccc12)C1CC1]

The title compound was prepared according to a procedure analogous to general procedure F, using (R)-8-bromo-2-(3-chloro-4-fluorophenoxy)-N-(1-cyclopropylethyl)quinazolin-4-amine, which was prepared according to a procedure analogous to general procedure C. ¹H NMR (400 MHz, CD₃OD) δ 8.28 (dd, J=8.3, 1.1 Hz, 1H), 7.72 (dd, J=7.3, 1.1 Hz, 1H), 7.53 (2m ovlp, 2H), 7.38 (t, J=8.9 Hz, 1H), 7.26 (m, 1H), 5.94 (br s, 1H), 3.87 (br d, J=2.7 Hz, 2H), 3.50 (2m ovlp, 3H), 2.77 (m, 2H), 1.31 (d, J=6.7 Hz, 3H), 1.07 (m, 1H), 0.57 (sep, J=4.5 Hz, 1H), 0.45 (sep, J=4.6 Hz, 1H), 0.22 (sext, J=5.0 Hz, 1H), 0.11 (sext, J=4.7 Hz, 1H). MS (ESI) m/z=439.00 (M+H)⁺. LCMS Ret time (UV 214/254): 1.198 min.

Example 70: (R)—N⁴-(1-cyclopropylethyl)-N²-(1H-pyrazol-3-yl)-8-(1,2,3,6-tetrahydropyridin-4-yl)quinazoline-2,4-diamine

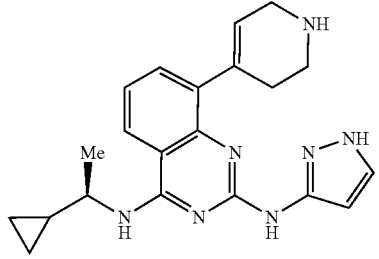 [SMILES: C[C@@H](Nc1nc(Nc2cc[nH]n2)nc2c(C3=CCNCC3)cccc12)C1CC1]

The title compound was prepared according to a procedure analogous to general procedure F, using (R)-8-bromo-N⁴-(1-cyclopropylethyl)-N-(1H-pyrazol-3-yl)quinazoline-2,4-diamine, which was obtained according to a procedure analogous to general procedure D. ¹H NMR (400 MHz, CD₃OD) δ 8.30 (dd, J=8.2, 1.0 Hz, 1H), 7.77 (2 d ovlp, 2H), 7.57 (t, J=7.9 Hz, 1H), 6.17 (br s and dd ovlp, 2H), 4.11 (br d, J=2.1 Hz, 2H), 4.02 (m, 1H), 3.63 (t, J=6.0 Hz, 2H), 2.80 (br m, 2H), 1.46 (d, J=6.7 Hz, 3H), 1.21 (m, 1H), 0.67 (m, 1H), 0.56 (m, 1H), 0.47 (sext, J=4.9 Hz, 1H), 0.36 (sext, J=4.8 Hz, 1H). MS (ESI) m/z=376.20 (M+H)⁺. LCMS Ret time (UV 214/254): 0.982 min.

Example 71: (R)—N⁴-(1-cyclopropylethyl)-N²-(1-methyl-1H-pyrazol-3-yl)-8-(1,2,3,6-tetrahydropyridin-4-yl)quinazoline-2,4-diamine

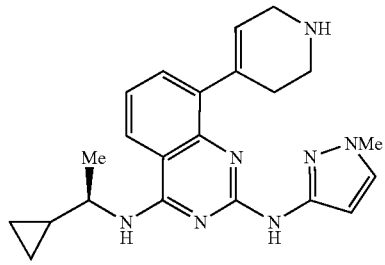 [SMILES: C[C@@H](Nc1nc(Nc2ccn(C)n2)nc2c(C3=CCNCC3)cccc12)C1CC1]

The title compound was prepared according to a procedure analogous to general procedure F, using (R)-8-bromo-N⁴-(1-cyclopropylethyl)-N²-(1-methyl-1H-pyrazol-3-yl)quinazoline-2,4-diamine which was obtained according to a procedure analogous to general procedure D. ¹H NMR (400 MHz, CD₃OD) δ 8.32 (d, J=8.2 Hz, 1H), 7.77 (d, J=7.3 Hz, 1H), 7.64 (s, 1H), 7.57 (t, J=7.7 Hz, 1H), 6.18 (br s, 1H), 6.09 (br s, 1H), 4.01 (2br s ovlp, 6H), 3.61 (t, J=6.0 Hz, 2H), 2.83 (br s, 2H), 1.45 (d, J=6.7 Hz, 3H), 1.22 (m, 1H), 0.65 (m, 1H), 0.55 (m, 1H), 0.46 (m, 1H), 0.35 (m, 1H). MS (ESI) m/z=390.10 (M+H)⁺. LCMS Ret time (UV 214/254): 0.962 min.

Example 72: (R)—N⁴-(1-cyclopropylethyl)-N²-(oxazol-2-ylmethyl)-8-(1,2,3,6-tetrahydropyridin-4-yl)quinazoline-2,4-diamine

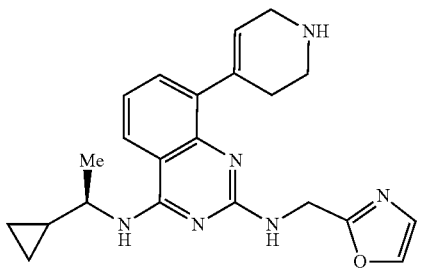 [SMILES: C[C@@H](Nc1nc(NCc2ncco2)nc2c(C3=CCNCC3)cccc12)C1CC1]

The title compound was prepared according to a procedure analogous to general procedure F, using (R)-8-bromo-N⁴-(1-cyclopropylethyl)-N²-(oxazol-2-ylmethyl)quinazoline-2,4-diamine, which was obtained according to a procedure analogous to general procedure A. ¹H NMR (400 MHz, CD₃OD) δ 8.20 (d, J=8.2 Hz, 1H), 7.90 (s, 1H), 7.66 (d, J=7.6 Hz, 1H), 7.46 (td, J=7.9, 1.9 Hz, 1H), 7.15 (s, 1H), 5.98 (br s, 1H), 4.78 (m, 2H), 3.90 (d, J=2.8 Hz, 2H), 3.75 (m, 1H), 3.59 (t, J=6.0 Hz, 2H), 2.72 (br m, 2H), 1.32 (d, J=6.6 Hz, 3H), 1.10 (m, 1H), 0.61 (m, 1H), 0.46 (m, 1H), 0.31 (sext, J=4.7 Hz, 1H), 0.18 (sext, J=4.9 Hz, 1H). MS (ESI) m/z=391.20 (M+H)⁺. LCMS Ret time (UV 214/254): 1.004 min.

Example 73: N²-(cyclohexylmethyl)-N⁴-(dicyclopropylmethyl)-8-(1,2,3,6-tetrahydropyridin-4-yl)quinazoline-2,4-diamine

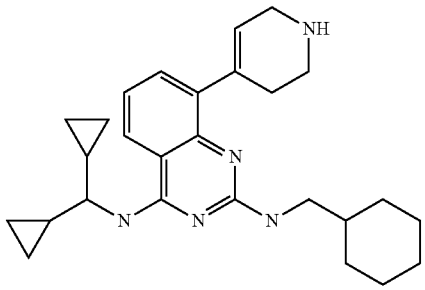 [SMILES: C1=C(c2cccc3c(NC(C4CC4)C4CC4)nc(NCC4CCCCC4)nc23)CCNC1]

The title compound was prepared according to a procedure analogous to general procedure F, using 8-bromo-N²-(cyclohexylmethyl)-N⁴-(dicyclopropylmethyl)quinazoline-2,4-diamine, which was obtained according to a procedure analogous to general procedure A. ¹H NMR (400 MHz, CD₃OD) δ 9.29 (d, J=8.3 Hz, 1H), 8.21 (dd, J=8.3, 1.1 Hz, 1H), 7.63 (dd, J=7.4, 1.1 Hz, 1H), 7.43 (t, J=8.0 Hz, 1H), 5.96 (s, 1H), 3.88 (m, 2H), 3.56 (t, J=6.1 Hz, 2H), 3.50 (m, 1H), 3.28 (d, J=6.7 Hz, 2H), 2.70 (m, 2H), 1.76 (d, J=11.2 Hz, 4H), 1.64 (ddd, J=17.2, 11.2, 6.7 Hz, 2H), 1.27 (m, 5H), 1.00 (dd, J=21.5, 11.4 Hz, 2H), 0.70 (m, 2H), 0.48 (dtd, J=18.6, 9.5, 5.1 Hz, 4H), 0.36 (dt, J=8.8, 5.0 Hz, 2H). MS (ESI) m/z=432.30 (M+H)⁺. LCMS Ret time (UV 214/254): 1.495 min.

Example 74: 8-(2-aminoethyl)-N²-(cyclohexylmethyl)-N⁴-(dicyclopropylmethyl)quinazoline-2,4-diamine

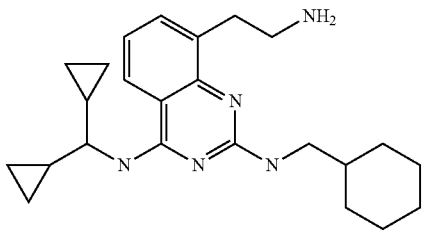 [SMILES: NCCc1cccc2c(NC(C3CC3)C3CC3)nc(NCC3CCCCC3)nc12]

The title compound was prepared according to a procedure analogous to general procedure E, using 8-bromo-N²-(cyclohexylmethyl)-N⁴-(dicyclopropylmethyl)quinazoline-2,4-diamine, which was obtained according to a procedure analogous to general procedure A. ¹H NMR (400 MHz, CD₃OD) δ 8.19 (dd, J=8.3, 1.2 Hz, 1H), 7.71 (dd, J=7.4, 1.0 Hz, 1H), 7.40 (t, J=7.8 Hz, 1H), 3.51 (t, J=8.8 Hz, 1H), 3.32 (app m, 4H), 3.22 (s, 2H), 1.78 (m, 4H), 1.64 (m, 3H), 1.28 (m, 6H), 1.02 (dd, J=22.0, 10.8 Hz, 2H), 0.70 (m, 2H), 0.47 (m, 4H), 0.36 (m, 2H). MS (ESI) m/z=394.20 (M+H)⁺. LCMS Ret time (UV 214/254): 1.455 min.

Example 75: 8-(aminomethyl)-N²-(cyclohexylmethyl)-N⁴-(dicyclopropylmethyl)quinazoline-2,4-diamine

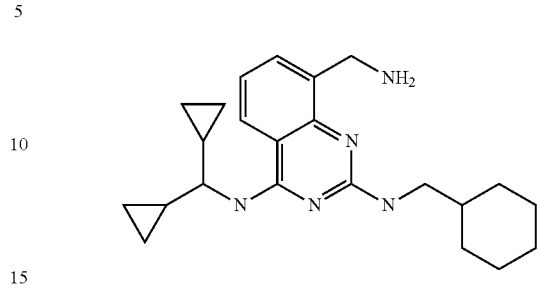

Step A: 2-((cyclohexylmethyl)amino)-4-((dicyclopropylmethyl)amino)quinazoline-8-carbonitrile was prepared according to a procedure analogous to general procedure J, using 8-bromo-N²-(cyclohexylmethyl)-N⁴-(dicyclopropylmethyl)quinazoline-2,4-diamine, which was obtained according to a procedure analogous to general procedure A.

Step B: The title compound was prepared according to a procedure analogous to general procedure K using 2-((cyclohexylmethyl)amino)-4-((dicyclopropylmethyl)amino)quinazoline-8-carbonitrile. ¹H NMR (400 MHz, CD₃OD) δ 8.33 (dd, J=8.3, 1.2 Hz, 1H), 7.87 (dd, J=7.5, 1.1 Hz, 1H), 7.48 (t, J=7.8 Hz, 1H), 4.45 (s, 2H), 3.51 (t, J=8.8 Hz, 1H), 3.33 (app d, 2H), 1.78 (d, J=9.9 Hz, 4H), 1.65 (ddd, J=15.7, 11.2, 6.2 Hz, 3H), 1.29 (m, 6H), 1.03 (dd, J=21.8, 10.5 Hz, 2H), 0.70 (m, 2H), 0.48 (m, 4H), 0.35 (m, 2H). MS (ESI) m/z=380.20 (M+H)⁺. LCMS Ret time (UV 214/254): 1.333 min.

Example 76: (R)—N²-(cyclohexylmethyl)-N⁴-(1-cyclopropylethyl)-8-(1,2,3,6-tetrahydropyridin-4-yl)quinazoline-2,4-diamine

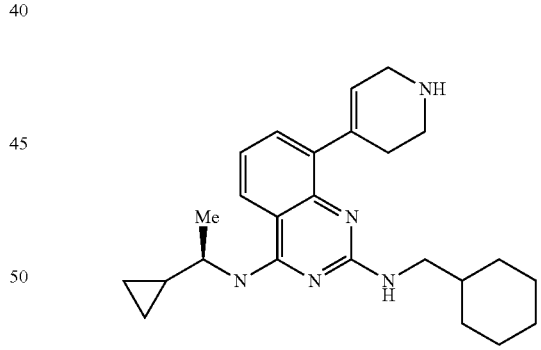

The title compound was prepared according to a procedure analogous to general procedure F, using (R)-8-bromo-N²-(cyclohexylmethyl)-N⁴-(1-cyclopropylethyl)quinazoline-2,4-diamine, which was obtained according to a procedure analogous to general procedure A. ¹H NMR (400 MHz, CD₃OD) δ 9.11 (d, J=7.8 Hz, 1H), 8.19 (dd, J=8.3, 1.2 Hz, 1H), 7.62 (dd, J=7.4, 1.1 Hz, 1H), 7.42 (t, J=8.0 Hz, 1H), 5.95 (m, 1H), 3.95 (m, 1H), 3.88 (m, 2H), 3.56 (t, J=6.1 Hz, 2H), 3.34 (ddd, J=15.0, 13.4, 6.6 Hz, 2H), 2.70 (m, 2H), 1.78 (t, J=11.2 Hz, 4H), 1.64 (m, 2H), 1.45 (d, J=6.7 Hz, 3H), 1.23 (m, 4H), 1.00 (m, 2H), 0.67 (m, 1H), 0.55 (m, 1H), 0.37 (m, 2H). MS (ESI) m/z=406.20 (M+H)⁺. LCMS Ret time (UV 214/254): 1.405 min.

Example 77: ((R)-8-(2-aminoethyl)-N²-(cyclohexylmethyl)-N⁴-(1-cycloprrpylethyl)quinazoline-2,4-diamine

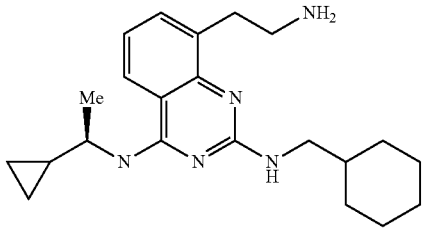 [SMILES: C[C@@H](Nc1nc(NCC2CCCCC2)nc2c(CCN)cccc12)C1CC1]

The title compound was prepared according to a procedure analogous to general procedure E, using (R)-8-bromo-N²-(cyclohexylmethyl)-N⁴-(1-cyclopropylethyl)quinazoline-2,4-diamine, which was obtained according to a procedure analogous to general procedure A. $^1$H NMR (400 MHz, CD$_3$OD) δ 8.17 (dd, J=8.3, 1.1 Hz, 1H), 7.70 (dd, J=7.4, 0.9 Hz, 1H), 7.39 (t, J=8.0 Hz, 1H), 3.95 (td, J=13.1, 6.4 Hz, 1H), 3.38 (m, 2H), 3.22 (m, 4H), 1.80 (t, J=14.9 Hz, 4H), 1.65 (m, 2H), 1.44 (d, J=6.7 Hz, 3H), 1.23 (m ovlp, 4H), 1.04 (dd, J=22.3, 10.6 Hz, 2H), 0.67 (m, 1H), 0.55 (m, 1H), 0.37 (m, 2H). MS (ESI) m/z=368.20 (M+H)$^+$. LCMS Ret time (UV 214/254): 1.385 min.

Example 78: (R)-8-(aminomethyl)-N²-(cyclohexylmethyl)-N⁴-(1-cyclopropylethyl)quinazoline-2,4-diamine

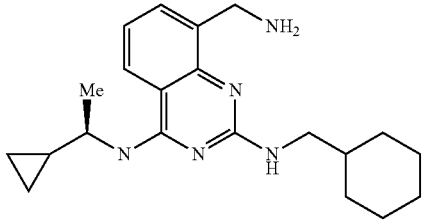 [SMILES: C[C@@H](Nc1nc(NCC2CCCCC2)nc2c(CN)cccc12)C1CC1]

Step A: (R)-2-((cyclohexylmethyl)amino)-4-((1-cyclopropylethyl)amino)quinazoline-8-carbonitrile was prepared according to a procedure analogous to general procedure J using (R)-8-bromo-N²-(cyclohexylmethyl)-N⁴-(1-cyclopropylethyl)quinazoline-2,4-diamine, which was obtained according to a procedure analogous to general procedure A.

Step B: The title compound was prepared according to a procedure analogous to general procedure K, using (R)-2-((cyclohexylmethyl)amino)-4-((1-cyclopropylethyl)amino)quinazoline-8-carbonitrile. $^1$H NMR (400 MHz, CD$_3$OD) δ 8.31 (dd, J=8.2, 0.9 Hz, 1H), 7.87 (d, J=7.4 Hz, 1H), 7.46 (t, J=7.9 Hz, 1H), 4.46 (s, 2H), 3.95 (dq, J=13.4, 6.6 Hz, 1H), 3.39 (m ovlp, 5H), 1.79 (t, J=14.2 Hz, 4H), 1.66 (m, 2H), 1.45 (d, J=6.7 Hz, 3H), 1.22 (tdd, J=13.3, 10.4, 5.0 Hz, 4H), 1.04 (m, 2H), 0.67 (m, 1H), 0.55 (m, 1H), 0.37 (m, 2H). MS (ESI) m/z=354.30 (M+H)$^+$. LCMS Ret time (UV 214/254): 1.297 min.

Example 79: (R)—N²-(3-chloro-4-fluorophenyl)-N⁴-(3,3-dimethylbutan-2-yl)-8-(1,2,3,6-tetrahydropyridin-4-yl)quinazoline-2,4-diamine

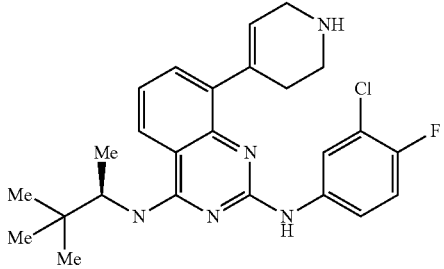 [SMILES: C[C@@H](Nc1nc(Nc2ccc(F)c(Cl)c2)nc2c(C3=CCNCC3)cccc12)C(C)(C)C]

The title compound was prepared according to a procedure analogous to general procedure F, using (R)-8-bromo-N²-(3-chloro-4-fluorophenyl)-N⁴-(3,3-dimethylbutan-2-yl)quinazoline-2,4-diamine, which was obtained according to a procedure analogous to general procedure A. $^1$H NMR (400 MHz, CD$_3$OD) δ 8.33 (dd, J=8.3, 1.2 Hz, 1H), 8.00 (dd, J=6.6, 2.6 Hz, 1H), 7.71 (dd, J=7.5, 1.2 Hz, 1H), 7.52 (dd, J=8.1, 7.6 Hz, 1H), 7.41 (ddd, J=8.9, 4.2, 2.6 Hz, 1H), 7.32 (t, J=8.9 Hz, 1H), 6.01 (br s, 1H), 4.57 (q, J=7.0 Hz, 1H), 3.91 (m, 2H), 3.60 (t, J=6.1 Hz, 2H), 2.76 (m, 2H), 1.30 (d, J=6.9 Hz, 3H), 1.01 (s, 9H). MS (ESI) m/z=454.20 (M+H)$^+$. LCMS Ret time (UV 214/254): 1.420 min.

Example 80: (R)—N⁴-(3,3-dimethylbutan-2-yl)-N²-(3-fluoro-5-methylphenyl)-8-(1,2,3,6-tetrahydropyridin-4-yl)quinazoline-2,4-diamine

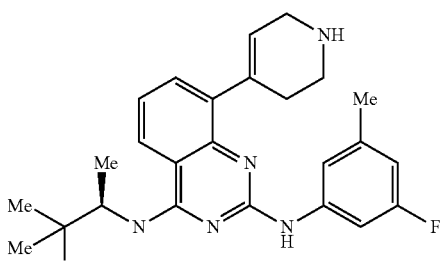

The title compound was prepared according to a procedure analogous to general procedure F, using (R)-8-bromo-N⁴-(3,3-dimethylbutan-2-yl)-N²-(3-fluoro-5-methylphenyl)quinazoline-2,4-diamine, which was obtained according to a procedure analogous to general procedure A. $^1$H NMR (400 MHz, CD$_3$OD) δ 8.78 (d, J=9.3 Hz, 1H), 8.33 (dd, J=8.3, 1.2 Hz, 1H), 7.72 (dd, J=7.5, 1.2 Hz, 1H), 7.52 (t, J=7.7 Hz, 1H), 7.38 (d, J=10.7 Hz, 1H), 7.21 (s, 1H), 6.82 (d, J=9.4 Hz, 1H), 6.01 (m, 1H), 4.63 (q, J=7.0 Hz, 1H), 3.91 (m, 2H), 3.60 (t, J=6.1 Hz, 2H), 2.76 (m, 2H), 2.39 (s, 3H), 1.31 (d, J=6.9 Hz, 3H), 1.02 (s, 9H). MS (ESI) m/z=434.20 (M+H)$^+$. LCMS Ret time (UV 214/254): 1.416 min.

Example 81: (R)—N²-(cyclohexylmethyl)-N⁴-(3,3-dimethylbutan-2-yl)-8-(1,2,3,6-tetrahydropyridin-4-yl)quinazoline-2,4-diamine

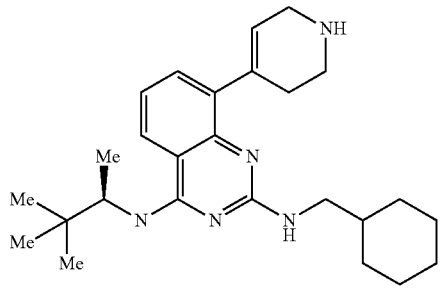 [SMILES: C[C@@H](Nc1nc(NCC2CCCCC2)nc2c(C3=CCNCC3)cccc12)C(C)(C)C]

The title compound was prepared according to a procedure analogous to general procedure F, using (R)-8-bromo-N²-(cyclohexylmethyl)-N⁴-(3,3-dimethylbutan-2-yl)quinazoline-2,4-diamine, which was obtained according to a procedure analogous to general procedure A. ¹H NMR (400 MHz, CD$_3$OD) δ 8.50 (d, J=9.2 Hz, 1H), 8.25 (dd, J=8.3, 1.2 Hz, 1H), 7.63 (dd, J=7.4, 1.1 Hz, 1H), 7.43 (t, J=8.0 Hz, 1H), 5.96 (br s, 1H), 4.71 (m, 1H), 3.88 (m, 2H), 3.57 (t, J=6.1 Hz, 2H), 3.46 (dd, J=13.4, 6.3 Hz, 1H), 3.28 (d, J=7.2 Hz, 1H), 2.71 (m, 2H), 1.77 (m, 4H), 1.69 (dt, J=14.6, 7.0 Hz, 2H), 1.31 (d, J=6.9 Hz, 3H), 1.26 (m, 2H), 1.04 (s, 11H). MS (ESI) m/z=422.20 (M+H)⁺. LCMS Ret time (UV 214/254): 1.526 min.

Example 82: (R)-8-(2-aminoethyl)-N²-(3-chloro-4-fluorophenyl)-N⁴-(3,3-dimethylbutan-2-yl)quinazoline-2,4-diamine

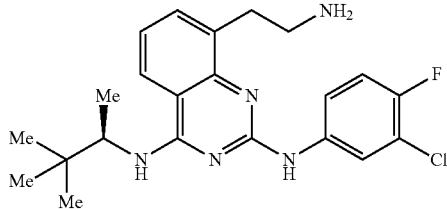 [SMILES: C[C@@H](Nc1nc(Nc2ccc(F)c(Cl)c2)nc2c(CCN)cccc12)C(C)(C)C]

The title compound was prepared according to a procedure analogous to general procedure E, using (R)-8-bromo-N²-(3-chloro-4-fluorophenyl)-N⁴-(3,3-dimethylbutan-2-yl)quinazoline-2,4-diamine, which was obtained according to a procedure analogous to general procedure A. ¹H NMR (400 MHz, CD$_3$OD) δ 8.75 (d, J=9.0 Hz, 1H), 8.31 (dd, J=8.3, 1.1 Hz, 1H), 8.07 (dd, J=6.6, 2.6 Hz, 1H), 7.79 (d, J=6.6 Hz, 1H), 7.48 (t, J=7.7 Hz, 1H), 7.43 (ddd, J=8.9, 4.1, 2.7 Hz, 1H), 7.32 (t, J=8.9 Hz, 1H), 4.60 (m, 1H), 3.29 (m, 4H), 1.31 (d, J=6.9 Hz, 3H), 1.02 (s, 9H). MS (ESI) m/z=416.20 (M+H)⁺. LCMS Ret time (UV 214/254): 1.390 min.

Example 83: (R)-8-(2-aminoethyl)-N⁴-(3,3-dimethylbutan-2-yl)-N²-(3-fluoro-5-methylphenyl)quinazoline-2,4-diamine

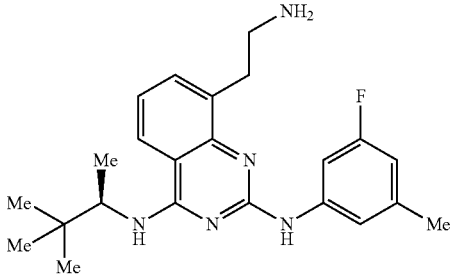 [SMILES: Cc1cc(F)cc(Nc2nc(N[C@H](C)C(C)(C)C)c3cccc(CCN)c3n2)c1]

The title compound was prepared according to a procedure analogous to general procedure E using (R)-8-bromo-N⁴-(3,3-dimethylbutan-2-yl)-N²-(3-fluoro-5-methylphenyl)quinazoline-2,4-diamine, which was obtained according to a procedure analogous to general procedure A. ¹H NMR (400 MHz, CD$_3$OD) δ 8.76 (d, J=9.4 Hz, 1H), 8.31 (dd, J=8.3, 1.1 Hz, 1H), 7.79 (d, J=6.5 Hz, 1H), 7.46 (m, 2H), 7.24 (s, 1H), 6.83 (d, J=9.3 Hz, 1H), 4.67 (quint, J=7.0 Hz, 1H), 3.29 (m, 4H), 2.40 (s, 3H), 1.32 (d, J=6.9 Hz, 3H), 1.03 (s, 9H). MS (ESI) m/z=396.30 (M+H)⁺. LCMS Ret time (UV 214/254): 1.332 min.

Example 84: (R)-8-(2-aminoethyl)-N²-(cyclohexylmethyl)-N⁴-(3,3-dimethylbutan-2-yl)quinazoline-2,4-diamine

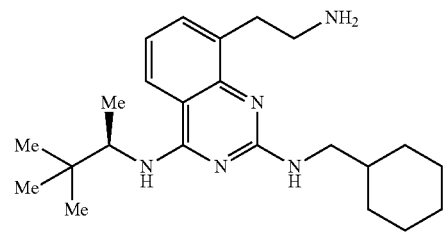 [SMILES: C[C@@H](Nc1nc(NCC2CCCCC2)nc2c(CCN)cccc12)C(C)(C)C]

The title compound was prepared according to a procedure analogous to general procedure E, using (R)-8-bromo-N²-(cyclohexylmethyl)-N⁴-(3,3-dimethylbutan-2-yl)quinazoline-2,4-diamine, which was obtained according to a procedure analogous to general procedure A. ¹H NMR (400 MHz, CD$_3$OD) δ 8.49 (d, J=9.3 Hz, 1H), 8.24 (dd, J=8.3, 1.1 Hz, 1H), 7.71 (dd, J=7.4, 0.9 Hz, 1H), 7.40 (t, J=7.7 Hz, 1H), 4.71 (m, 1H), 3.49 (dd, J=13.4, 6.3 Hz, 1H), 3.35 (d, J=7.2 Hz, 1H), 3.22 (m, 4H), 2.66 (s, 1H), 1.81 (m, 4H), 1.69 (m, 2H), 1.30 (t, J=7.3 Hz, 3H), 1.25 (m, 2H), 1.03 (s, 9H). MS (ESI) m/z=385.30 (M+H)⁺. LCMS Ret time (UV 214/254): 1.411 min.

Example 85: (R)-8-(2-aminoethyl)-N²-(3-chloro-2-fluorobenzyl)-N⁴-(3,3-dimethylbutan-2-yl)quinazoline-2,4-diamine

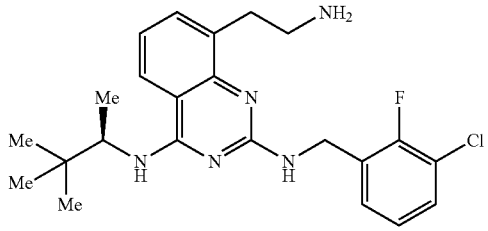 [SMILES: C[C@@H](Nc1nc(NCc2cccc(Cl)c2F)nc2c(CCN)cccc12)C(C)(C)C]

The title compound was prepared according to a procedure analogous to general procedure E, using (R)-8-bromo-N²-(3-chloro-2-fluorobenzyl)-N⁴-(3,3-dimethylbutan-2-yl)quinazoline-2,4-diamine, which was obtained according to a procedure analogous to general procedure A. ¹H NMR (400 MHz, CD₃OD) δ 8.52 (d, J=9.3 Hz, 1H), 8.22 (dd, J=8.3, 1.1 Hz, 1H), 7.73 (d, J=7.4 Hz, 1H), 7.40 (dd, J=14.7, 7.1 Hz, 3H), 7.15 (t, J=7.4 Hz, 1H), 4.82 (m, 2H), 4.59 (m, 1H), 3.23 (m, 4H), 1.21 (d, J=6.9 Hz, 3H), 0.92 (s, 9H). MS (ESI) m/z=430.20 (M+H)⁺. LCMS Ret time (UV 214/254): 1.325 min.

Example 86: (R)-8-(aminomethyl)-N²-(cyclohexylmethyl)-N⁴-(3,3-dimethylbutan-2-yl)quinazoline-2,4-diamine

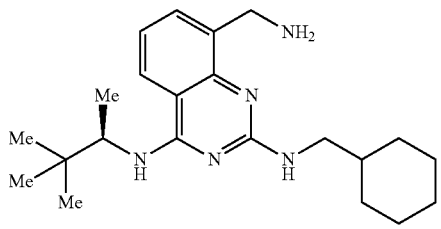 [SMILES: C[C@@H](Nc1nc(NCC2CCCCC2)nc2c(CN)cccc12)C(C)(C)C]

Step A: (R)-2-((cyclohexylmethyl)amino)-4-((3,3-dimethylbutan-2-yl)amino)quinazoline-8-carbonitrile was prepared according to a procedure analogous to general procedure J using (R)-8-bromo-N²-(cyclohexylmethyl)-N⁴-(3,3-dimethylbutan-2-yl)quinazoline-2,4-diamine, which was obtained according to a procedure analogous to general procedure A.

Step B: The title compound was prepared according to a procedure analogous to general procedure K, using (R)-2-((cyclohexylmethyl)amino)-4-((3,3-dimethylbutan-2-yl)amino)quinazoline-8-carbonitrile. ¹H NMR (400 MHz, CD₃OD) δ 8.56 (d, J=9.0 Hz, 1H), 8.37 (dd, J=8.3, 1.1 Hz, 1H), 7.88 (dd, J=7.5, 0.9 Hz, 1H), 7.47 (t, J=7.9 Hz, 1H), 4.71 (q, J=7.0 Hz, 1H), 4.46 (s, 2H), 3.50 (dd, J=13.4, 6.3 Hz, 1H), 3.36 (dd, J=13.4, 7.1 Hz, 1H), 1.75 (m, 6H), 1.32 (d, J=6.9 Hz, 3H), 1.25 (m, 4H), 1.09 (m, 2H), 1.04 (s, 9H). MS (ESI) m/z=370.30 (M+H)⁺. LCMS Ret time (UV 214/254): 1.359 min.

Example 87: (R)-8-(aminomethyl)-N²-(3-chloro-2-fluorobenzyl)-N⁴-(3,3-dimethylbutan-2-yl)quinazoline-2,4-diamine

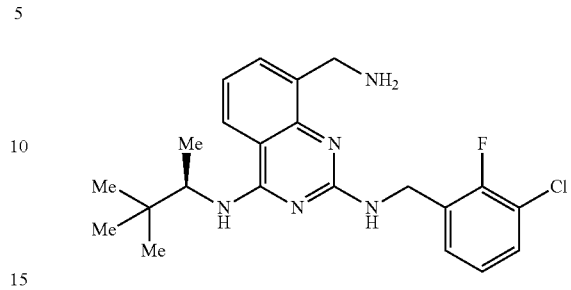

Step A: (R)-2-((3-chloro-2-fluorobenzyl)amino)-4-((3,3-dimethylbutan-2-yl)amino)-4-((3,3-dimethylbutan-2-yl)amino)quinazoline-8-carbonitrile was prepared according to a procedure analogous to general procedure J, using (R)-8-bromo-N²-(3-chloro-2-fluorobenzyl)-N⁴-(3,3-dimethylbutan-2-yl)quinazoline-2,4-diamine, which was obtained according to a procedure analogous to general procedure A.

Step B: The title compound was prepared from (R)-2-((3-chloro-2-fluorobenzyl)amino)-4-((3,3-dimethylbutan-2-yl)amino)quinazoline-8-carbonitrile according to a procedure analogous to general procedure K. ¹H NMR (400 MHz, CD₃OD) δ 8.35 (dd, J=8.3, 1.1 Hz, 1H), 7.90 (d, J=6.6 Hz, 1H), 7.48 (t, J=7.9 Hz, 1H), 7.39 (m, 2H), 7.14 (td, J=7.9, 0.9 Hz, 1H), 4.82 (m, 2H), 4.57 (q, J=6.9 Hz, 1H), 4.49 (s, 2H), 1.21 (d, J=6.9 Hz, 3H), 0.91 (s, 9H). MS (ESI) m/z=416.10 (M+H)⁺. LCMS Ret time (UV 214/254): 1.280 min.

Example 88: (R)—N²-(3-chloro-4-fluorophenyl)-8-(1,2,3,6-tetrahydropyridin-4-yl)-N⁴-(1-(thiophen-2-yl)ethyl)quinazoline-2,4-diamine

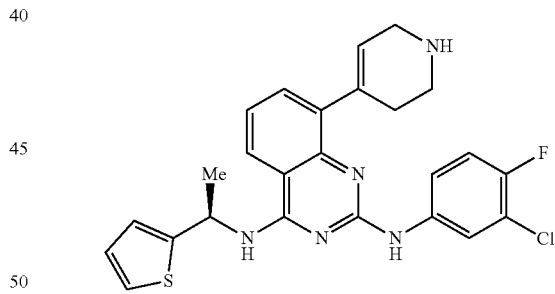

The title compound was obtained according to a procedure analogous to general procedure F, using (R)-8-bromo-N²-(3-chloro-4-fluorophenyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. ¹H NMR (400 MHz, CD₃OD) δ 8.29 (dd, J=8.3, 1.1 Hz, 1H), 7.81 (dd, J=6.6, 2.6 Hz, 1H), 7.72 (dd, J=7.4, 1.1 Hz, 1H), 7.51 (m, 1H), 7.43 (ddd, J=8.9, 4.1, 2.7 Hz, 1H), 7.31 (m, 1H), 7.28 (t, J=8.9 Hz, 1H), 7.02 (d, J=3.5 Hz, 1H), 6.97 (dd, J=5.0, 3.6 Hz, 1H), 6.01 (m, 1H), 5.84 (q, J=6.8 Hz, 1H), 3.92 (m, 2H), 3.61 (t, J=6.1 Hz, 2H), 2.76 (m, 2H), 2.03 (s, 1H), 1.80 (d, J=7.0 Hz, 3H). MS (ESI) m/z=480.00 (M+H)⁺. LCMS Ret time (UV 214/254): 1.330 min.

Example 89: (R)—N²-(3-fluoro-5-methylphenyl)-8-(1,2,3,6-tetrahydropyridin-4-yl)-N⁴-(1-(thiophen-2-yl)ethyl)quinazoline-2,4-diamine

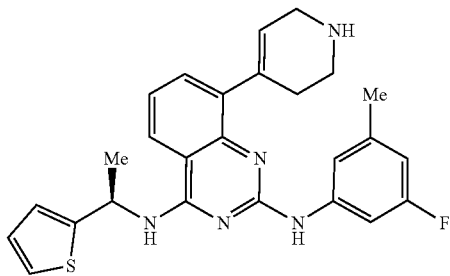 [SMILES: Cc1cc(F)cc(Nc2nc(N[C@H](C)c3cccs3)c3cccc(C4=CCNCC4)c3n2)c1]

The title compound was obtained according to a procedure analogous to general procedure F, using (R)-8-bromo-N²-(3-fluoro-5-methylphenyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. ¹H NMR (400 MHz, CD₃OD) δ 8.29 (dd, J=8.3, 1.3 Hz, 1H), 7.72 (dd, J=7.5, 1.3 Hz, 1H), 7.51 (dd, J=8.2, 7.6 Hz, 1H), 7.31 (dd, J=5.1, 1.2 Hz, 1H), 7.25 (dt, J=10.4, 1.9 Hz, 1H), 7.19 (s, 1H), 7.05 (dt, J=3.5, 1.0 Hz, 1H), 6.97 (dd, J=5.1, 3.6 Hz, 1H), 6.81 (d, J=9.4 Hz, 1H), 6.02 (m, 1H), 5.92 (q, J=6.9 Hz, 1H), 3.91 (m, 2H), 3.60 (t, J=6.1 Hz, 2H), 2.76 (m, 2H), 2.33 (s, 3H), 2.03 (s, 1H), 1.81 (d, J=7.0 Hz, 3H). MS (ESI) m/z=460.20 (M+H)⁺. LCMS Ret time (UV 214/254): 1.295 min.

Example 90: (R)—N²-(cyclohexylmethyl)-8-(1,2,3,6-tetrahydropyridin-4-yl)-N⁴-(1-(thiophen-2-yl)ethyl)quinazoline-2,4-diamine

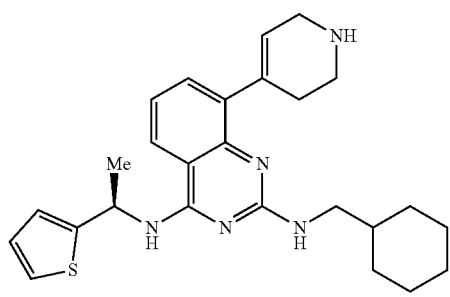 [SMILES: C[C@@H](Nc1nc(NCC2CCCCC2)nc2c(C3=CCNCC3)cccc12)c1cccs1]

The title compound was obtained according to a procedure analogous to general procedure F, using (R)-8-bromo-N²-(cyclohexylmethyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. ¹H NMR (400 MHz, CD₃OD) δ 9.46 (d, J=7.3 Hz, 1H), 8.22 (dd, J=8.3, 1.2 Hz, 1H), 7.64 (dd, J=7.5, 1.2 Hz, 1H), 7.43 (dd, J=8.1, 7.6 Hz, 1H), 7.31 (dd, J=5.1, 1.2 Hz, 1H), 7.10 (dd, J=2.5, 1.0 Hz, 1H), 6.99 (dd, J=5.1, 3.6 Hz, 1H), 5.95 (m, 2H), 3.88 (m, 2H), 3.56 (t, J=6.1 Hz, 2H), 3.48 (m, 1H), 3.31 (dd, J=13.4, 6.4 Hz, 1H), 2.71 (m, 2H), 1.81 (d, J=7.0 Hz, 3H), 1.64 (m, 6H), 1.21 (m, 4H), 0.97 (m, 2H). MS (ESI) m/z=448.30 (M+H)⁺. LCMS Ret time (UV 214/254): 1.384 min.

Example 91: (R)-8-(2-aminoethyl)-N²-(3-chloro-4-fluorophenyl)-N⁴-(1-(thiophen-2-yl)ethyl)quinazoline-2,4-diamine

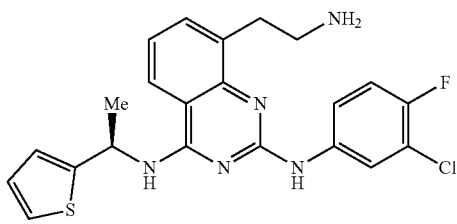 [SMILES: C[C@@H](Nc1nc(Nc2ccc(F)c(Cl)c2)nc2c(CCN)cccc12)c1cccs1]

The title compound was obtained according to a procedure analogous to general procedure E, using (R)-8-bromo-N²-(3-chloro-4-fluorophenyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. ¹H NMR (400 MHz, CD₃OD) δ 8.24 (d, J=8.3 Hz, 1H), 7.90 (dd, J=6.5, 2.3 Hz, 1H), 7.76 (d, J=7.2 Hz, 1H), 7.46 (m, 2H), 7.29 (d, J=5.2 Hz, 1H), 7.26 (t, J=8.9 Hz, 1H), 7.04 (d, J=3.5 Hz, 1H), 6.97 (dd, J=5.0, 3.6 Hz, 1H), 5.88 (q, J=6.9 Hz, 1H), 3.32 (m, 4H), 1.80 (d, J=7.0 Hz, 3H). MS (ESI) m/z=442.00 (M+H)⁺. LCMS Ret time (UV 214/254): 1.295 min.

Example 92: (R)-8-(2-aminoethyl)-N²-(3-fluoro-5-methylphenyl)-N⁴-(1-(thiophen-2-yl)ethyl)quinazoline-2,4-diamine

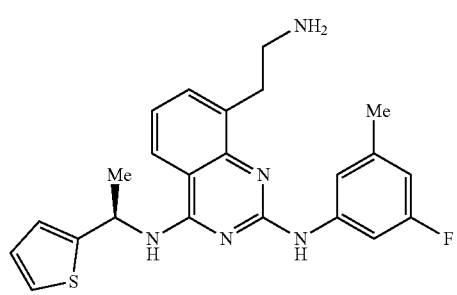 [SMILES: Cc1cc(F)cc(Nc2nc(N[C@H](C)c3cccs3)c3cccc(CCN)c3n2)c1]

The title compound was obtained according to a procedure analogous to general procedure E, using (R)-8-bromo-N²-(3-fluoro-5-methylphenyl)-1V-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. ¹H NMR (400 MHz, CD₃OD) δ 8.27 (dd, J=8.3, 1.2 Hz, 1H), 7.80 (dd, J=7.4, 1.1 Hz, 1H), 7.48 (m, 1H), 7.31 (m, 2H), 7.22 (s, 1H), 7.06 (m, 1H), 6.97 (dd, J=5.1, 3.6 Hz, 1H), 6.81 (d, J=9.4 Hz, 1H), 5.94 (q, J=7.1 Hz, 1H), 3.28 (m, 4H), 2.33 (s, 3H), 1.81 (d, J=7.0 Hz, 3H). MS (ESI) m/z=422.20 (M+H)⁺. LCMS Ret time (UV 214/254): 1.293 min.

Example 93: (R)-8-(2-aminoethyl)-N²-(cyclohexylmethyl)-N⁴-(1-(thiophen-2-yl)ethyl)quinazoline-2,4-diamine

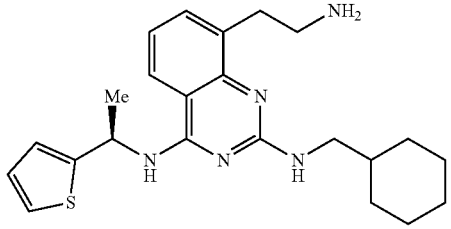 [SMILES: C[C@@H](Nc1nc(NCC2CCCCC2)nc2c(CCN)cccc12)c1cccs1]

The title compound was obtained according to a procedure analogous to general procedure E, using (R)-8-bromo-N²-(cyclohexylmethyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. $^1$H NMR (400 MHz, CD$_3$OD) δ 8.21 (dd, J=8.3, 1.2 Hz, 1H), 7.72 (dd, J=7.4, 1.1 Hz, 1H), 7.40 (dd, J=8.1, 7.6 Hz, 1H), 7.31 (dd, J=5.1, 1.2 Hz, 1H), 7.11 (dd, J=2.5, 1.0 Hz, 1H), 6.99 (dd, J=5.1, 3.6 Hz, 1H), 5.96 (q, J=7.1 Hz, 1H), 3.51 (dd, J=13.5, 6.8 Hz, 1H), 3.35 (dd, 1H), 3.23 (d, J=3.2 Hz, 4H), 1.81 (d, J=7.0 Hz, 3H), 1.66 (m, 6H), 1.23 (m, 3H), 0.99 (m, 2H). MS (ESI) m/z=410.20 (M+H)$^+$. LCMS Ret time (UV 214/254): 1.370 min.

Example 94: (R)-8-(2-aminoethyl)-N²-(3-chloro-2-fluorobenzyl)-N⁴-(1-(thiophen-2-yl)ethyl)quinazoline-2,4-diamine

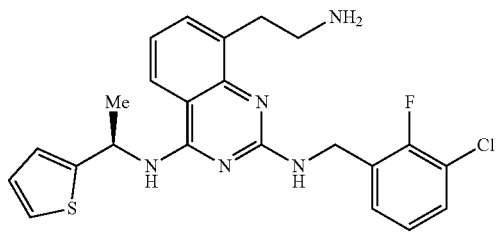 [SMILES: C[C@@H](Nc1nc(NCc2cccc(Cl)c2F)nc2c(CCN)cccc12)c1cccs1]

The title compound was obtained according to a procedure analogous to general procedure E, using (R)-8-bromo-N²-(3-chloro-2-fluorobenzyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. $^1$H NMR (400 MHz, CD$_3$OD) δ 8.22 (dd, J=8.3, 1.2 Hz, 1H), 7.75 (dd, J=7.4, 1.1 Hz, 1H), 7.42 (td, J=7.1, 3.6 Hz, 2H), 7.34 (m, 1H), 7.30 (dd, J=5.1, 1.2 Hz, 1H), 7.11 (td, J=7.9, 1.1 Hz, 1H), 7.04 (dt, J=3.5, 1.0 Hz, 1H), 6.96 (dd, J=5.1, 3.6 Hz, 1H), 5.98 (q, J=7.1 Hz, 1H), 3.25 (m, 4H), 1.77 (d, J=7.0 Hz, 3H). MS (ESI) m/z=456.20 (M+H)$^+$. LCMS Ret time (UV 214/254): 1.284 min.

Example 95: (R)-8-(aminomethyl)-N²-(3-fluoro-5-methylphenyl)-N⁴-(1-(thiophen-2-yl)ethyl)quinazoline-2,4-diamine

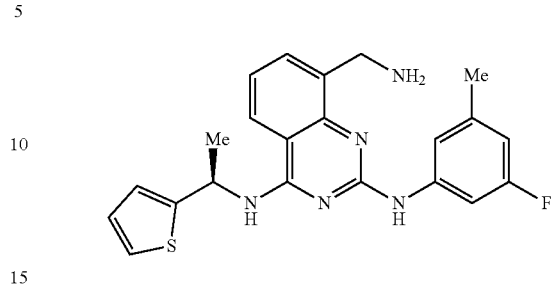

Step A: (R)-2-((3-fluoro-5-methylphenyl)amino)-4-((1-(thiophen-2-yl)ethyl)amino)quinazoline-8-carbonitrile was obtained according to a procedure analogous to general procedure J, using (R)-8-bromo-N²-(3-fluoro-5-methylphenyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B.

Step B: The title compound was obtained from (R)-2-((3-fluoro-5-methylphenyl)amino)-4-((1-(thiophen-2-yl)ethyl)amino)quinazoline-8-carbonitrile according to a procedure analogous to general procedure K. $^1$H NMR (400 MHz, CD$_3$OD) δ 8.32 (d, J=7.4 Hz, 1H), 7.86 (d, J=7.0 Hz, 1H), 7.44 (t, J=7.8 Hz, 1H), 7.38 (d, J=10.9 Hz, 1H), 7.29 (dd, J=5.1, 1.2 Hz, 1H), 7.23 (s, 1H), 7.07 (dt, J=3.5, 1.0 Hz, 1H), 6.97 (dd, J=5.1, 3.6 Hz, 1H), 6.73 (d, J=9.3 Hz, 1H), 5.96 (q, J=6.9 Hz, 1H), 4.52 (d, J=3.8 Hz, 2H), 2.33 (s, 3H), 1.80 (d, J=7.0 Hz, 3H). MS (ESI) m/z=408.20 (M+H)$^+$. LCMS Ret time (UV 214/254): 1.254 min.

Example 96: (R)-8-(aminomethyl)-N²-(cyclohexylmethyl)-N⁴-(1-(thiophen-2-yl)ethyl)quinazoline-2,4-diamine

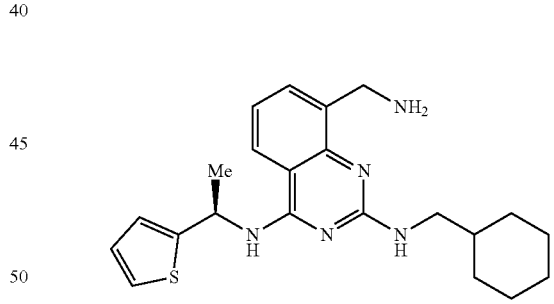

Step A: (R)-2-((cyclohexylmethyl)amino)-4-((1-(thiophen-2-yl)ethyl)amino)quinazoline-8-carbonitrile was obtained according to a procedure analogous to general procedure J, using (R)-8-bromo-N²-(cyclohexylmethyl)-N⁴-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B.

Step B: The title compound was obtained from (R)-2-((cyclohexylmethyl)amino)-4-((1-(thiophen-2-yl)ethyl)amino)quinazoline-8-carbonitrile according to a procedure analogous to general procedure K. $^1$H NMR (400 MHz, CD$_3$OD) δ 8.34 (d, J=8.2 Hz, 1H), 7.88 (d, J=7.5 Hz, 1H), 7.47 (t, J=7.9 Hz, 1H), 7.31 (dd, J=5.1, 1.1 Hz, 1H), 7.11 (dd, J=2.5, 1.0 Hz, 1H), 6.99 (dd, J=5.1, 3.6 Hz, 1H), 5.96 (q, J=6.9 Hz, 1H), 4.46 (d, J=1.3 Hz, 2H), 3.52 (dd, J=13.3, 6.7 Hz, 1H), 3.36 (dd, J=1.4, 7.0 Hz, 1H), 1.81 (d, J=7.0 Hz, 3H), 1.67 (m, 6H), 1.24 (m, 3H), 1.00 (m, 2H). MS (ESI) m/z=396.30 (M+H)$^+$. LCMS Ret time (UV 214/254): 1.268 min.

Example 97: (R)-8-(aminomethyl)-N$^2$-(3-chloro-2-fluorobenzyl)-N$^4$-(1-(thiophen-2-yl)ethyl)quinazoline-2,4-diamine

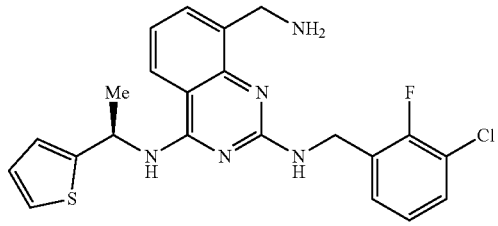 [SMILES: C[C@@H](Nc1nc(NCc2cccc(Cl)c2F)nc2c(CN)cccc12)c1cccs1]

Step A: (R)-2-((3-chloro-2-fluorobenzyl)amino)-4-((1-(thiophen-2-yl)ethyl)amino)quinazoline-8-carbonitrile was obtained according to a procedure analogous to general procedure J, using (R)-8-bromo-N$^2$-(3-chloro-2-fluorobenzyl)-N$^4$-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B
Step B: The title compound was obtained from (R)-2-((3-chloro-2-fluorobenzyl)amino)-4-((1-(thiophen-2-yl)ethyl)amino)quinazoline-8-carbonitrile according to a procedure analogous to general procedure K. $^1$H NMR (400 MHz, CD$_3$OD) δ 8.31 (d, J=8.0 Hz, 1H), 7.87 (s, 1H), 7.47 (m, 1H), 7.38 (t, J=8.3 Hz, 1H), 7.32 (t, J=6.7 Hz, 1H), 7.27 (dd, J=5.1, 1.1 Hz, 1H), 7.09 (td, J=7.9, 1.0 Hz, 1H), 7.02 (d, J=3.5 Hz, 1H), 6.94 (dd, J=5.1, 3.6 Hz, 1H), 5.95 (q, J=7.1 Hz, 1H), 4.85 (m, 2H), 4.46 (m, 2H), 2.66 (s, 1H), 1.74 (d, J=7.0 Hz, 3H). MS (ESI) m/z=442.20 (M+H)$^+$. LCMS Ret time (UV 214/254): 1.228 min.

Example 98: N$^2$-(3-chloro-4-fluorophenyl)-N$^4$-(2-ethylbutyl)-8-(1,2,3,6-tetrahydropyridin-4-yl)quinazoline-2,4-diamine

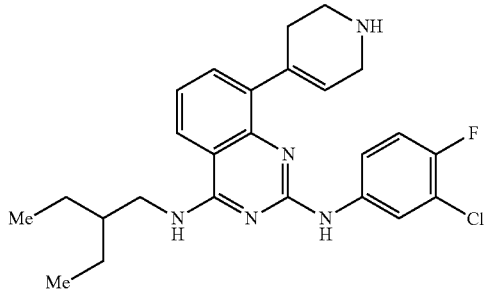 [SMILES: CCC(CC)CNc1nc(Nc2ccc(F)c(Cl)c2)nc2c(C3=CCNCC3)cccc12]

The title compound was obtained according to a procedure analogous to general procedure F, using 8-bromo-N$^2$-(3-chloro-4-fluorophenyl)-N$^4$-(2-ethylbutyl)quinazoline-2,4-diamine, which was prepared by a procedure analogous to general procedure A. MS (ESI) m/z=454.46 (M+H)$^+$. LCMS Ret time (UV 214/254): 1.483 min.

Example 99: 2-((3-chloro-4-fluorophenyl)amino)-4-((2-ethylbutyl)amino)quinazoline-8-carbonitrile

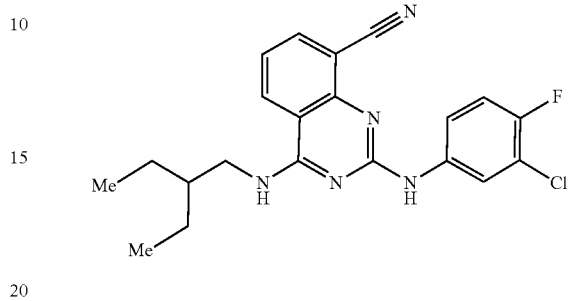

The title compound was obtained according to a procedure analogous to general procedure J, using 8-bromo-N$^2$-(3-chloro-4-fluorophenyl)-N$^4$-(2-ethylbutyl)quinazoline-2,4-diamine, which was prepared by a procedure analogous to general procedure A. $^1$H NMR (400 MHz, CD$_3$OD) δ 8.24 (br s, 1H), 8.13 (dd, J=8.4, 1.2 Hz, 1H), 7.88 (dd, J=7.2, 1.2 Hz, 1H), 7.42 (br d, J=8.4 Hz, 1H), 7.14 (t, J=7.6 Hz, 1H), 7.04 (t, J=9.0 Hz, 1H), 3.49 (d, J=7.2 Hz, 2H), 1.69 (m, 2H), 1.39 (m, 5H), 0.87 (t, J=7.4 Hz, 6H). MS (ESI) m/z=398.40 (M+H)$^+$. LCMS Ret time (UV 214/254): 2.421 min.

Example 100: (R)—N$^2$-(3-chloro-4-fluorophenyl)-8-(1,2,3,6-tetrahydropyridin-4-yl)-N$^4$-(1-(thiophen-2-yl)propyl)quinazoline-2,4-diamine

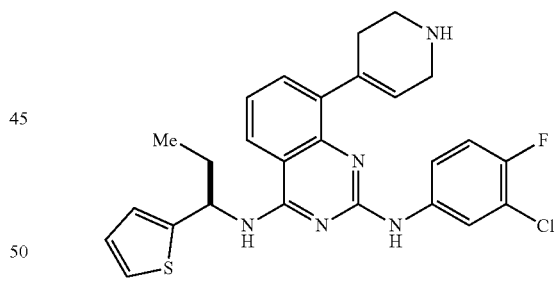

The title compound was prepared using a procedure analogous to general procedure F, using (R)-8-bromo-N$^2$-(3-chloro-4-fluorophenyl)-N$^4$-(1-(thiophen-2-yl)propyl)quinazoline-2,4-diamine, which was prepared by a procedure analogous to general procedure A using (R)-1-(thiophen-2-yl)propan-1-amine hydrochloride, which was prepared by a procedure analogous to general procedure B. $^1$H NMR (400 MHz, CD$_3$OD) δ 8.14 (d, J=7.6 Hz, 1H), 8.04 (br s, 1H), 7.55 (br d, J=6.8 Hz, 1H), 7.39 (m, 1H), 7.33 (m, 1H), 7.22 (2m ovlp, 2H), 7.02 (d, J=3.6 Hz, 1H), 6.90 (dd, J=4.8, 3.2 Hz, 1H), 5.90 (s, 1H), 5.65 (t, J=7.4 Hz, 1H), 3.90 (d, J=2.4 Hz, 2H), 3.54 (t, J=5.6 Hz, 2H), 2.80 (br s, 2H), 2.11 (quint, J=7.2 Hz, 2H), 1.00 (t, J=7.2 Hz, 3H). MS (ESI) m/z=494.70 (M+H)$^+$. LCMS Ret time (UV 214/254): 1.381 min.

Example 101: (R)—N²-(3-chloro-4-fluorophenyl)-8-(piperazin-1-yl)-N⁴-(1-(thiophen-2-yl)propyl)quinazoline-2,4-diamine

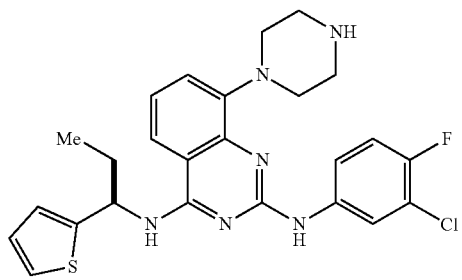 [SMILES: CC[C@@H](Nc1nc(Nc2ccc(F)c(Cl)c2)nc2c(N3CCNCC3)cccc12)c1cccs1]

The title compound was prepared using a procedure analogous to general procedure G, using (R)-8-bromo-N²-(3-chloro-4-fluorophenyl)-N⁴-(1-(thiophen-2-yl)propyl)quinazoline-2,4-diamine, which was prepared by a procedure analogous to general procedure A using (R)-1-(thiophen-2-yl)propan-1-amine hydrochloride, which was prepared by a procedure analogous to general procedure B. ¹H NMR (400 MHz, CD₃OD) δ 8.05 (br d, J=2.4 Hz, 1H), 7.98 (d, J=7.6 Hz, 1H), 7.53 (br d, J=2.4 Hz, 1H), 7.44 (m, 1H), 7.32 (m, 1H), 7.21 (2m ovlp, 2H), 7.01 (d, J=2.4 Hz, 1H), 6.90 (dd, J=5.2, 3.6 Hz, 1H), 5.64 (t, J=7.2 Hz, 1H), 3.54 (br s, 4H), 3.26 (br s, 4H), 2.11 (quint, J=7.2 Hz, 2H), 0.99 (t, J=7.2 Hz, 6H). MS (ESI) m/z=497.67 (M+H)⁺. LCMS Ret time (UV 214/254): 1.370 min.

Example 102: N²-(3-chloro-4-fluorophenyl)-N⁴-(2-ethylbutyl)-8-(piperazin-1-yl)quinazoline-2,4-diamine

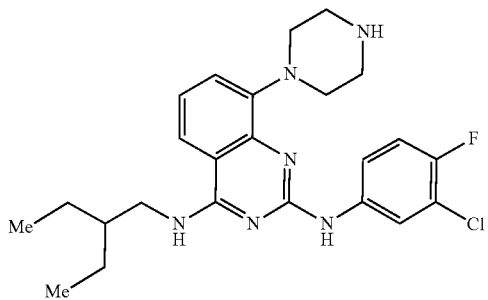 [SMILES: CCC(CC)CNc1nc(Nc2ccc(F)c(Cl)c2)nc2c(N3CCNCC3)cccc12]

The title compound was obtained according to a procedure analogous to general procedure G, using 8-bromo-N²-(3-chloro-4-fluorophenyl)-N⁴-(2-ethylbutyl)quinazoline-2,4-diamine, which was prepared by a procedure analogous to general procedure A. ¹H NMR (400 MHz, CDCl₃) δ 8.14 (dd, J=6.8, 2.4 Hz, 1H), 7.58 (d, J=7.2 Hz, 1H), 7.53 (m, 1H), 7.07 (3m ovlp, 3H), 3.49 (d, J=7.2 Hz, 2H), 3.25 (br s, 2H), 3.17 (br s, 2H), 1.71 (m, 1H), 1.38 (m, 4H), 0.88 (t, J=7.6 Hz, 6H). MS (ESI) m/z=457.97 (M+H)⁺. LCMS Ret time (UV 214/254): 1.361 min.

Example 103: (R)—N²-(cycloheptylmethyl)-N⁴-(1-cyclopropylethyl)-8-(1,2,3,6-tetrahydropyridin-4-yl)quinazoline-2,4-diamine

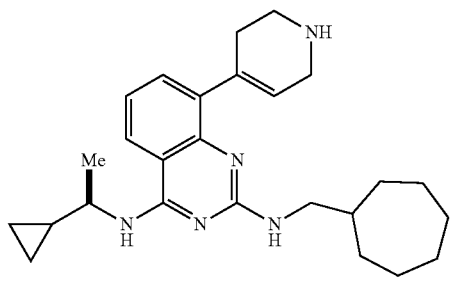 [SMILES: C[C@@H](Nc1nc(NCC2CCCCCC2)nc2c(C3=CCNCC3)cccc12)C1CC1]

The title compound was obtained according to a procedure analogous to general procedure F, using (R)-8-bromo-N²-(cycloheptylmethyl)-N⁴-(1-cyclopropylethyl)quinazoline-2,4-diamine, which was prepared by a procedure analogous to general procedure A. ¹H NMR (400 MHz, CDCl₃) δ 9.05 (br s, 1H), 8.02 (br d, J=7.2 Hz, 1H), 7.83 (br d, J=2.0 Hz, 1H), 7.41 (d, J=7.2 Hz, 1H), 7.28 (t, J=7.6 Hz, 1H), 5.80 (s, 1H), 3.83 (br m, 3H), 2.45 (br m, 2H), 3.29 (t, J=6.4 Hz, 2H), 2.60 (br s, 2H), 1.75 (m, 3H), 1.64 (m, 2H), 1.56 (m, 2H), 1.43 (d, J=6.8 Hz, 3H), 0.65 (m, 1H), 0.55 (m, 1H), 0.39 (m, 1H), 0.35 (m, 1H). MS (ESI) m/z=420.99 (M+H)⁺. LCMS Ret time (UV 214/254): 1.411 min.

Example 104: (R)—N⁴-(1-cyclopropylethyl)-N²-((4-methylcyclohexyl)methyl)-8-(1,2,3,6-tetrahydropyridin-4-yl)quinazoline-2,4-diamine

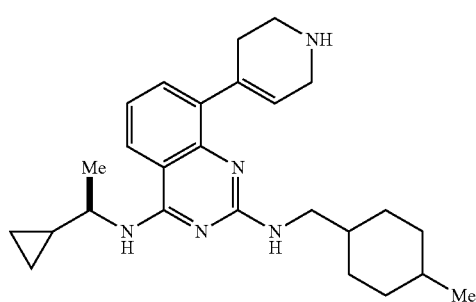 [SMILES: CC1CCC(CNc2nc(N[C@H](C)C3CC3)c3cccc(C4=CCNCC4)c3n2)CC1]

The title compound was obtained according to a procedure analogous to general procedure F, using (R)-8-bromo-N⁴-(1-cyclopropylethyl)-N²-((4-methylcyclohexyl)methyl)quinazoline-2,4-diamine, which was prepared by a procedure analogous to general procedure A. MS (ESI) m/z=420.09 (M+H)⁺. LCMS Ret time (UV 214/254): 1.398 min.

Example 105: (R)—N²-(cyclopentylmethyl)-N⁴-(1-cyclopropylethyl)-8-(1,2,3,6-tetrahydropyridin-4-yl)quinazoline-2,4-diamine

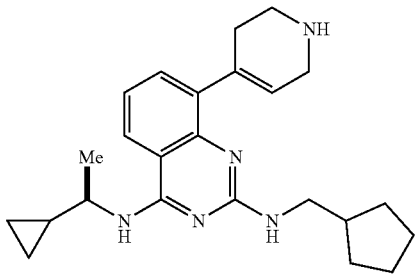 [SMILES: C[C@@H](Nc1nc(NCC2CCCC2)nc2c(C3=CCNCC3)cccc12)C1CC1]

The title compound was obtained according to a procedure analogous to general procedure F, using (R)-8-bromo-N-(cyclopentylmethyl)-N⁴-(1-cyclopropylethyl)quinazoline-2,4-diamine, which was prepared by a procedure analogous to general procedure A. $^1$H NMR (400 MHz, CDCl$_3$) δ 8.99 (d, J=7.6 Hz, 1H), 8.66 (d, J=8.0 Hz, 1H), 8.24 (br t, J=5.4 Hz, 1H), 7.41 (d, J=7.2 Hz, 1H), 7.31 (t, J=8.0 Hz, 1H), 5.84 (s, 1H), 3.90 (br s, 2H), 3.83 (m, 1H), 3.53 (br s, 2H), 3.38 (t, J=6.8 Hz, 2H), 2.73 (br s, 2H), 2.15 (m, 1H), 2.15 (m, 2H), 1.60 (m, 4H), 1.57 (m, 2H), 1.55 (d, J=6.8 Hz, 3H), 1.43 (m, 1H), 1.29 (m, 2H), 0.60 (m, 1H), 0.51 (m, 1H), 0.37 (m, 1H), 0.31 (m, 1H). MS (ESI) m/z=392.09 (M+H)⁺. LCMS Ret time (UV 214/254): 0.702 min.

Example 106: (R)—N²-(cyclobutylmethyl)-N⁴-(1-cyclopropylethyl)-8-(1,2,3,6-tetrahydropyridin-4-yl)quinazoline-2,4-diamine

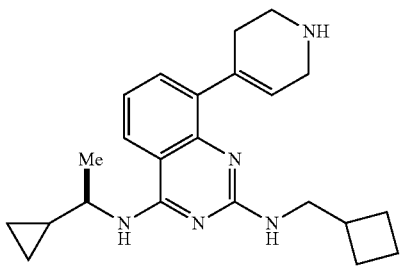 [SMILES: C[C@@H](Nc1nc(NCC2CCC2)nc2c(C3=CCNCC3)cccc12)C1CC1]

The title compound was obtained according to a procedure analogous to general procedure F, using (R)-8-bromo-N²-(cyclobutylmethyl)-N⁴-(1-cyclopropylethyl)quinazoline-2,4-diamine, which was prepared by a procedure analogous to general procedure A. $^1$H NMR (400 MHz, CDCl$_3$) δ 8.91 (d, J=7.6 Hz, 1H), 8.63 (br d, J=7.6 Hz, 1H), 8.17 (t, J=5.2 Hz, 1H), 7.41 (d, J=6.4 Hz, 1H), 7.32 (t, J=6.8 Hz, 1H), 5.85 (s, 1H), 3.90 (br s, 2H), 3.86 (m 1H), 3.49 (br s, 2H), 3.46 (m, 2H), 2.93 (br s, 1H), 2.74 (br s, 1H), 2.58 (quint, J=7.6 Hz, 1H), 2.09 (m, 2H), 1.89 (m, 2H), 1.78 (quint, J=10.4 Hz, 2H), 1.50 (d, J=5.2 Hz, 3H), 1.40 (m, 1H), 0.60 (m, 1H), 0.51 (m, 1H), 0.40 (m, 1H), 0.33 (m, 1H). MS (ESI) m/z=378.00 (M+H)⁺. LCMS Ret time (UV 214/254): 0.936 min.

Example 107: (R)—N⁴-(1-cyclopropylethyl)-N²-(3-fluoro-5-methylphenyl)-8-(1,2,3,6-tetrahydropyridin-4-yl)quinazoline-2,4-diamine

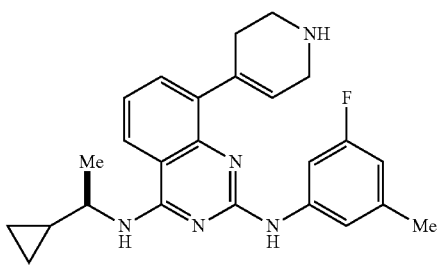 [SMILES: Cc1cc(F)cc(Nc2nc(N[C@H](C)C3CC3)c3cccc(C4=CCNCC4)c3n2)c1]

The title compound was obtained according to a procedure analogous to general procedure F, using (R)-8-bromo-N⁴-(1-cyclopropylethyl)-N²-(3-fluoro-5-methylphenyl)quinazoline-2,4-diamine, which was prepared by a procedure analogous to general procedure A. $^1$H NMR (400 MHz, CDCl$_3$) δ 8.66 (d, J=8.0 Hz, 1H), 8.38 (d, J=8.4 Hz, 1H), 7.51 (d, J=7.2 Hz, 1H), 7.40 (t, J=7.6 Hz, 1H), 7.29 (t, J=7.2 Hz, 1H), 7.06 (s, 1H), 6.70 (d, J=8.2 Hz, 1H), 5.90 (s, 1H), 3.96 (br s, 2H), 3.84 (m, 1H), 2.75 (br m, 2H), 2.32 (s, 3H), 1.48 (d, J=6.8 Hz, 2H), 0.88 (m, 1H), 0.64 (m, 1H), 0.51 (m, 1H), 0.33 (2m ovlp, 2H). MS (ESI) m/z=417.93 (M+H)⁺. LCMS Ret time (UV 214/254): 1.367 min.

Example 108: N⁴-(dicyclopropylmethyl)-N²-(3-fluoro-5-methylphenyl)-8-(1,2,3,6-tetrahydropyridin-4-yl)quinazoline-2,4-diamine

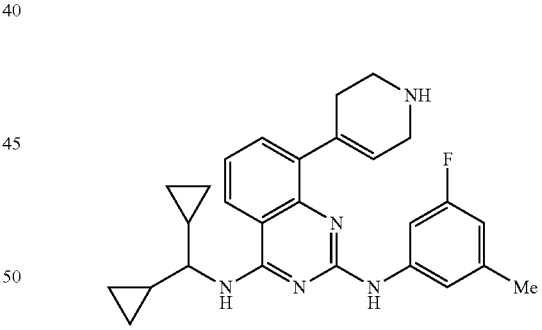

The title compound was obtained according to a procedure analogous to general procedure F, using 8-bromo-N⁴-(dicyclopropylmethyl)-N²-(3-fluoro-5-methylphenyl)quinazoline-2,4-diamine, which was prepared by a procedure analogous to general procedure A. $^1$H NMR (400 MHz, CDCl$_3$) δ 7.93 (d, J=7.2 Hz, 1H), 7.66 (d, J 8.0 Hz, 1H), 7.47 (d, J=7.2 Hz, 1H), 7.17 (t, J=8.0 Hz, 1H), 6.82 (s, 1H), 6.51 (d, J=6.5 Hz, 1H), 6.04 (br s, 1H), 5.86 (br s, 1H), 3.81 (br s, 2H), 3.67 (dd, J=14.6, 8.0 Hz, 1H), 3.42 (t, J=2.4 Hz, 1H), 2.88 (br s, 2H), 2.30 (s, 3H), 1.11 (m, 2H), 0.59 (m, 2H), 0.45 (m, 6H). MS (ESI) m/z=444.51 (M+H)⁺. LCMS Ret time (UV 214/254): 1.316 min.

Example 109: (R)-6-(2-aminoethyl)-N⁴-(1-cyclopropylethyl)-N²-(3,5-difluorophenyl)quinazoline-2,4-diamine

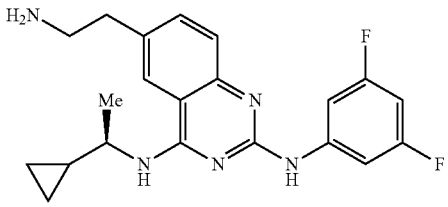 [SMILES: C[C@@H](Nc1nc(Nc2cc(F)cc(F)c2)nc2ccc(CCN)cc12)C1CC1]

The title compound was obtained according to a procedure analogous to general procedure E, using (R)-6-bromo-N⁴-(1-cyclopropylethyl)-N²-(3,5-difluorophenyl)quinazoline-2,4-diamine, which was prepared by a procedure analogous to general procedure A. ¹H NMR (400 MHz, CD₃OD) δ 8.25 (d, J=1.4 Hz, 1H), 7.79 (dd, J=8.6, 1.8 Hz, 1H), 7.58 (d, J=8.5 Hz, 1H), 7.30 (m, 2H), 6.83 (tt, J=9.1, 2.3 Hz, 1H), 3.91 (dq, J=9.1, 6.7 Hz, 1H), 3.30 (m, 2H), 3.13 (t, J=7.8 Hz, 2H), 1.46 (d, J=6.7 Hz, 3H), 1.21 (m, 1H), 0.68 (m, 1H), 0.54 (m, 1H), 0.39 (dt, J=9.6, 5.0 Hz, 1H), 0.32 (dt, J=14.2, 4.7 Hz, 1H). MS (ESI) m/z=384.10. LCMS Ret time (UV 214/254): 1.199 min.

Example 110: (R)—N-(1-cyclopropylethyl)-2-(3,5-difluorobenzyl)quinazolin-4-amine

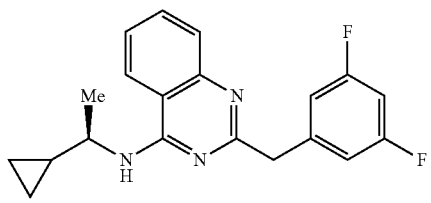 [SMILES: C[C@@H](Nc1nc(Cc2cc(F)cc(F)c2)nc2ccccc12)C1CC1]

Step A: A mixture of methyl 2-aminobenzoate (0.129 mL, 1.00 mmol, 1 eq.) and 2-(3,5-difluorophenyl)acetonitrile (306 mg, 2.00 mmol, 2 eq.) were heated to 100° C. in a solution of 4 M HCl in dioxane (3 mL, 0.33M). After completion of the reaction, the mixture was concentrated in vacuo and suspended in 50% aqueous NaHCO₃. The solid was collected and was washed with water to provide 2-(3,5-difluorobenzyl)quinazolin-4(3H)-one as a crude white solid (258 mg, 95%). ¹H NMR (400 MHz, (CD₃)₂SO) δ 8.06 (dd, J=7.9, 1.3 Hz, 1H), 7.72 (ddd, J=8.4, 7.2, 1.5 Hz, 1H), 7.55 (d, J=8.1 Hz, 1H), 7.42 (ddd, J=8.0, 7.1, 1.0 Hz, 1H), 7.10 (m, 3H), 3.96 (s, 2H). MS (ESI) m/z=273.10 (M+H)⁺. LCMS Ret time (UV 214/254): 1.179 min.
Step B: A mixture of 2-(3,5-difluorobenzyl)quinazolin-4(3H)-one, prepared by a procedure analogous to Step A, (68 mg, 0.25 mmol, 1 eq.), BOP (144 mg, 0.33 mmol, 1.3 eq.), DBU (75 µL, 0.50 mmol, 2 eq.), and (R)-1-cyclopropylethan-1-amine (80 µL, 0.75 mmol, 3 eq.) was stirred in MeCN (2.5 mL, 0.1 M) for 2 h. After reaction completion, the mixture was diluted with 10% aqueous NH₄Cl and the mixture was extracted with CH₂Cl₂ and passed through a phase separator. The organic layer was collected and concentrated in vacuo and purified by reverse phase HPLC (32.5-52.5% MeCN in H₂O) to provide the title compound as its corresponding trifluoroacetate salt (18 mg, 16%). ¹H NMR (400 MHz, CDCl₃) δ 8.05 (d, J=8.1 Hz, 1H), 7.88 (d, J=7.6 Hz, 1H), 7.71 (d, J=7.8 Hz, 1H), 7.50 (td, J=7.6, 1.0 Hz, 1H), 7.44 (td, J=8.2, 1.0 Hz, 1H), 7.04 (m, 2H), 6.76 (tt, J=8.8, 2.3 Hz, 1H), 4.19 (s, 2H), 3.89 (sext, J=6.9 Hz, 1H), 3.69 (br s, 2H), 1.44 (d, J=6.7 Hz, 3H), 1.21 (m, 1H), 0.68 (m, 1H), 0.55 (m, 1H), 0.36 (sext, J=4.9 Hz, 1H), 0.27 (sext, J=4.9 Hz, 1H). MS (ESI) m/z=340.20. LCMS Ret time (UV 214/254): 1.342 min.

Example 111: (R)—N⁸-(azetidin-3-ylmethyl)-N²-(3-chloro-4-fluorophenyl)-N⁴-(1-cyclopropylethyl)quinazoline-2,4,8-triamine

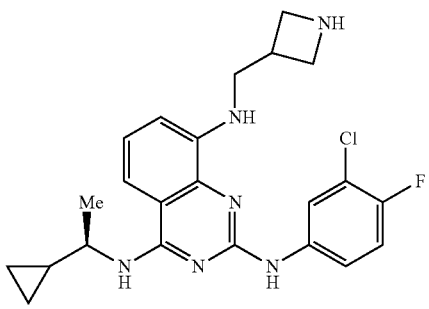 [SMILES: C[C@@H](Nc1nc(Nc2ccc(F)c(Cl)c2)nc2c(NCC3CNC3)cccc12)C1CC1]

The title compound was prepared according to a procedure analogous to general procedure G, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.04 (dd, J=6.6, 2.6 Hz, 1H), 7.58 (d, J=8.2 Hz, 1H), 7.41 (ddd, J=8.9, 4.1, 2.7 Hz, 1H), 7.34 (t, J=8.1 Hz, 1H), 7.26 (t, J=8.9 Hz, 1H), 7.11 (d, J=8.0 Hz, 1H), 4.27 (dd, J=11.2, 8.8 Hz, 2H), 4.00 (dd, J=11.2, 6.9 Hz, 2H), 3.84 (dq, J=9.0, 6.8 Hz, 1H), 3.54 (d, J=7.0 Hz, 2H), 3.34 (m, 1H), 1.43 (d, J=6.7 Hz, 3H), 1.19 (m, 1H), 0.65 (m, 1H), 0.52 (m, 1H), 0.33 (m, 2H). MS (ESI) m/z=441.10 (M+H)⁺. LCMS Ret time (UV 214/254): 1.417 min.

Example 112: (R)—N⁸-(azetidin-3-yl)-N²-(3-chloro-4-fluorophenyl)-N-(1-cyclopropylethyl)quinazoline-2,4,8-triamine

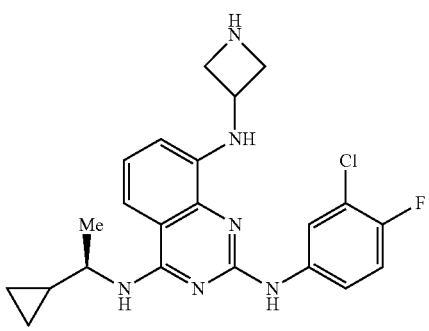 [SMILES: C[C@@H](Nc1nc(Nc2ccc(F)c(Cl)c2)nc2c(NC3CNC3)cccc12)C1CC1]

The title compound was prepared according to a procedure analogous to general procedure G, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.04 (dd, J=6.6, 2.6 Hz, 1H), 7.66 (d, J=8.2 Hz, 1H), 7.41 (ddd, J=8.9, 4.0, 2.8 Hz, 1H), 7.32 (t, J=8.2 Hz, 1H), 7.24 (t, J=9.0 Hz, 1H), 6.87 (d, J=8.0 Hz, 1H), 4.61 (m, 1H), 4.51 (dd, J=10.7, 7.3 Hz, 2H), 4.16 (dd, J=10.9, 6.3 Hz, 2H), 3.85 (dq, J=9.1, 6.7 Hz, 1H), 1.44 (d, J=6.7 Hz, 3H), 1.19 (m, 1H), 0.65 (m, 1H), 0.52 (m, 1H), 0.33 (m, 2H). MS (ESI) m/z=427.20 (M+H)+. LCMS Ret time (UV 214/254): 1.375 min.

Example 113: (R)-8-(azetidin-3-ylmethyl)-N²-(3-chloro-4-fluorophenyl)-N⁴-(1-cyclopropylethyl)quinazoline-2,4-diamine

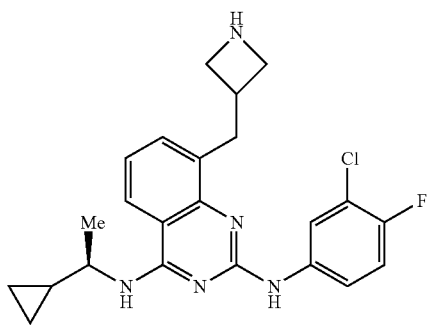 [SMILES: C[C@@H](Nc1nc(Nc2ccc(F)c(Cl)c2)nc2c(CC3CNC3)cccc12)C1CC1]

The title compound was prepared according to a procedure analogous to general procedure E, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.21 (dd, J=8.3, 1.1 Hz, 1H), 8.00 (dd, J=6.6, 2.6 Hz, 1H), 7.71 (d, J=7.2 Hz, 1H), 7.45 (t, J=7.9 Hz, 1H), 7.42 (ddd, J=8.9, 4.1, 2.7 Hz, 1H), 7.29 (t, J=8.8 Hz, 1H), 4.16 (dd, J=10.8, 8.2 Hz, 2H), 3.96 (dd, J=10.9, 6.0 Hz, 2H), 3.83 (dq, J=9.1, 6.7 Hz, 1H), 3.35 (br s, 3H), 1.44 (d, J=6.7 Hz, 3H), 1.18 (m, 1H), 0.66 (m, 1H), 0.52 (m, 1H), 0.32 (m, 2H). MS (ESI) m/z=426.10 (M+H)+. LCMS Ret time (UV 214/254): 1.291 min.

Example 114: (R)-8-((3-aminocyclobutyl)methyl)-N²-(3-chloro-4-fluorophenyl)-N⁴-(1-cyclopropylethyl)quinazoline-2,4-diamine

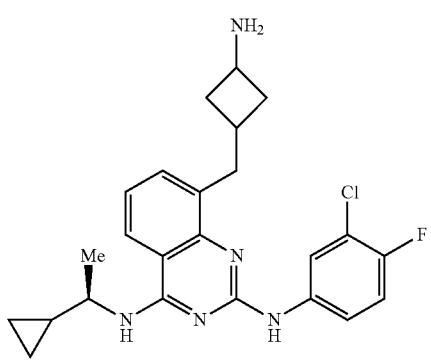 [SMILES: C[C@@H](Nc1nc(Nc2ccc(F)c(Cl)c2)nc2c(CC3CC(N)C3)cccc12)C1CC1]

The title compound was prepared according to a procedure analogous to general procedure E, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.18 (d, J=8.2 Hz, 1H), 8.00 (dt, J=6.7, 2.2 Hz, 1H), 7.68 (dd, J=7.4, 2.0 Hz, 1H), 7.44 (t, J=7.9 Hz, 1H), 7.39 (m, 1H), 7.29 (t, J=8.8 Hz, 1H), 3.97 (quintet, J=6.9 Hz, 0.5H), 3.83 (dq, J=9.1, 6.7 Hz, 1H), 3.65 (quintet, J=8.0 Hz, 0.5H), 3.16 (d, J=8.0 Hz, 1H), 3.09 (d, J=7.1 Hz, 1H), 2.88 (m, 0.5H), 2.57 (m, 0.5H), 2.51 (m, 1H), 2.30 (t, J=6.9 Hz, 2H), 1.96 (m, 1H), 1.44 (d, J=6.8 Hz, 3H), 1.19 (m, 1H), 0.66 (m, 1H), 0.53 (m, 1H), 0.33 (m, 2H). MS (ESI) m/z=440.10 (M+H)+. LCMS Ret time (UV 214/254): 1.331 min.

Example 115: (R)—N²-(3-chloro-4-fluorophenyl)-N⁴-(1-cyclopropylbut-3-en-1-yl)-8-(1,2,3,6-tetrahydropyridin-4-yl)quinazoline-2,4-diamine

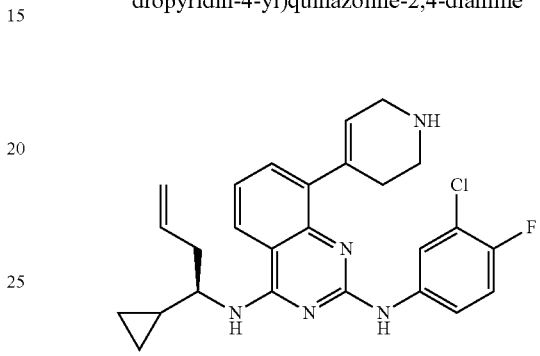

The title compound was prepared according to a procedure analogous to general procedure F, using (R)-8-bromo-N²-(3-chloro-4-fluorophenyl)-N⁴-(1-cyclopropylbut-3-en-1-yl)quinazoline-2,4-diamine, which was prepared by a procedure analogous to general procedure A using (R)-1-cyclopropylbut-3-en-1-amine hydrochloride, which was prepared by procedure B. ¹H NMR (400 MHz, CD₃OD) δ 8.26 (dd, J=8.2, 1.2 Hz, 1H), 7.89 (dd, J=6.6, 2.6 Hz, 1H), 7.71 (dd, J=7.5, 1.2 Hz, 1H), 7.52 (dd, J=8.1, 7.6 Hz, 1H), 7.39 (ddd, J=8.9, 4.1, 2.6 Hz, 1H), 7.29 (t, J=8.9 Hz, 1H), 6.00 (m, 1H), 5.83 (ddt, J=17.1, 10.1, 7.1 Hz, 1H), 5.08 (dd, J=17.1, 1.5 Hz, 1H), 5.01 (d, J=10.2 Hz, 1H), 3.91 (dd, J=5.2, 2.4 Hz, 2H), 3.81 (ddd, J=9.4, 8.0, 5.9 Hz, 1H), 3.60 (t, J=6.1 Hz, 2H), 2.75 (m, 2H), 2.59 (m, 2H), 1.20 (m, 1H), 0.69 (m, 1H), 0.51 (m, 1H), 0.32 (m, 2H). MS (ESI) m/z=464.20 (M+H)+. LCMS Ret time (UV 214/254): 1.362 min.

Example 116: (R)—N⁴-(1-cyclopropylbut-3-en-1-yl)-N²-(3,5-difluorophenyl)-8-(1,2,3,6-tetrahydropyridin-4-yl)quinazoline-2,4-diamine

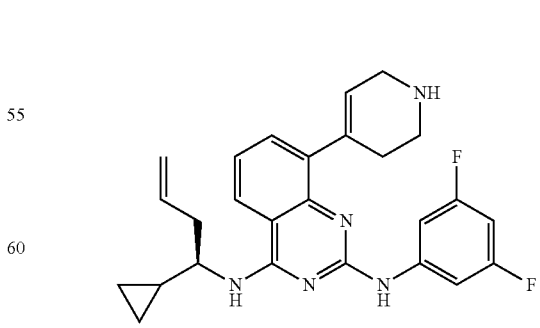

The title compound was prepared according to a procedure analogous to general procedure F, using (R)-8-bromo-N⁴-(1-cyclopropylbut-3-en-1-yl)-N²-(3,5-difluorophenyl)quinazoline-2,4-diamine, which was prepared by a procedure analogous to general procedure A using (R)-1-cyclopropylbut-3-en-1-amine hydrochloride, which was prepared by procedure B. ¹H NMR (400 MHz, CD₃OD) δ 8.28 (dd, J=8.2, 1.2 Hz, 1H), 7.73 (dd, J=7.5, 1.2 Hz, 1H), 7.54 (t, J=7.9 Hz, 1H), 7.30 (m, 2H), 6.82 (tt, J=9.1, 2.3 Hz, 1H), 6.01 (m, 1H), 5.86 (ddt, J=17.1, 10.2, 7.1 Hz, 1H), 5.12 (dd, J=17.1, 1.6 Hz, 1H), 5.03 (d, J=10.2 Hz, 1H), 3.89 (m, 3H), 3.60 (t, J=6.1 Hz, 2H), 2.76 (m, 2H), 2.63 (m, 2H), 1.22 (m, 1H), 0.72 (m, 1H), 0.53 (m, 1H), 0.36 (m, 2H). MS (ESI) m/z=448.30 (M+H)⁺. LCMS Ret time (UV 214/254): 1.345 min.

Example 117: (R)—N²-(cyclohexylmethyl)-N⁴-(1-cyclopropylbut-3-en-1-yl)-8-(1,2,3,6-tetrahydropyridin-4-yl)quinazoline-2,4-diamine

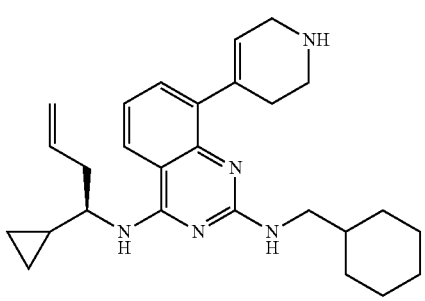 [SMILES: C=CC[C@@H](Nc1nc(NCC2CCCCC2)nc2c(C3=CCNCC3)cccc12)C1CC1]

The title compound was prepared according to a procedure analogous to general procedure F, using (R)-8-bromo-N²-(cyclohexylmethyl)-N⁴-(1-cyclopropylbut-3-en-1-yl)quinazoline-2,4-diamine, which was prepared by a procedure analogous to general procedure A using (R)-1-cyclopropylbut-3-en-1-amine hydrochloride, which was prepared by procedure B. ¹H NMR (400 MHz, CD₃OD) δ 9.11 (br d, J=8.3 Hz, 1H), 8.18 (dd, J=8.2, 1.1 Hz, 1H), 7.63 (dd, J=7.4, 1.0 Hz, 1H), 7.42 (t, J=7.8 Hz, 1H), 5.95 (m, 1H), 5.88 (ddt, J=17.0, 10.2, 7.1 Hz, 1H), 5.12 (dd, J=17.1, 1.6 Hz, 1H), 5.03 (d, J=10.2 Hz, 1H), 3.93 (m, 3H), 3.56 (t, J=6.1 Hz, 2H), 3.34 (m, 2H), 2.64 (m, 4H), 1.78 (m, 5H), 1.65 (m, 2H), 1.23 (m, 3H), 1.00 (m, 2H), 0.72 (m, 1H), 0.54 (m, 1H), 0.39 (m, 2H). MS (ESI) m/z=432.40 (M+H)⁺. LCMS Ret time (UV 214/254): 1.448 min.

Example 118: (R)-8-(2-aminoethyl)-N⁴-(1-cyclopropylethyl)-N²-(3-fluoro-5-methylphenyl)quinazoline-2,4-diamine

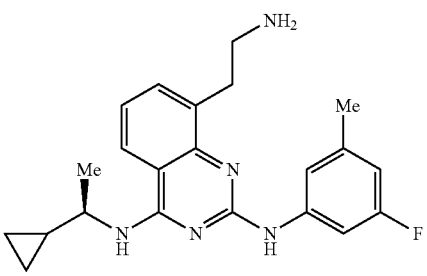 [SMILES: Cc1cc(F)cc(Nc2nc(N[C@H](C)C3CC3)c3cccc(CCN)c3n2)c1]

The title compound was obtained according to a procedure analogous to general procedure E, using (R)-8-bromo-N⁴-(1-cyclopropylethyl)-N²-(3-fluoro-5-methylphenyl)quinazoline-2,4-diamine, which was prepared by a procedure analogous to general procedure A. ¹H NMR (400 MHz, CD₃OD) δ 8.25 (dd, J=8.3, 1.2 Hz, 1H), 7.78 (dd, J=7.4, 1.1 Hz, 1H), 7.47 (t, J=7.8 Hz, 1H), 7.35 (dt, J=10.8, 1.8 Hz, 1H), 7.23 (s, 1H), 6.81 (d, J=9.3 Hz, 1H), 3.91 (dq, J=9.1, 6.7 Hz, 1H), 3.27 (m, 4H), 2.39 (s, 3H), 1.46 (d, J=6.7 Hz, 3H), 1.21 (m, 1H), 0.68 (m, 1H), 0.54 (m, 1H), 0.38 (sext, J=5.0 Hz, 1H), 0.30 (sext, J=4.7 Hz, 1H). MS (ESI) m/z=380.30 (M+H)⁺. LCMS Ret time (UV 214/254): 1.320 min.

Example 119: (R)-8-(2-aminoethyl)-N²-(3-chloro-2-fluorobenzyl)-N⁴-(1-cyclopropylethyl)quinazoline-2,4-diamine

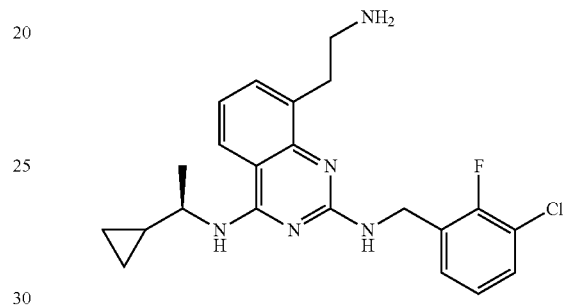

The title compound was prepared according to a procedure analogous to general procedure E using (R)-8-bromo-N²-(3-chloro-4-fluorobenzyl)-N⁴-(1-cyclopropylethyl)quinazoline-2,4-diamine, which was prepared according to a procedure analogous to general procedure A. ¹H NMR (400 MHz, CD₃OD) δ 8.17 (dd, J=8.3, 1.1 Hz, 1H), 7.71 (dd, J=7.4, 1.0 Hz, 1H), 7.39 (m, 3H), 7.15 (td, J=7.9, 0.9 Hz, 1H), 4.77 (q, J=15.5 Hz, 2H), 3.82 (dq, J=9.6, 6.6 Hz, 1H), 3.23 (m, 4H), 1.33 (d, J=6.7 Hz, 3H), 1.11 (m, 1H), 0.61 (m, 1H), 0.45 (m, 1H), 0.32 (sext, J=4.8 Hz, 1H), 0.16 (sext, J=4.8 Hz, 1H). MS (ESI) m/z=414.30 (M+H)⁺. LCMS Ret time (UV 214/254): 1.304 min.

Example 120: (R)—N²-(3-chloro-4-fluorophenyl)-N⁴-(1-cyclopropylethyl)-8-(1-methyl-1,2,3,6-tetrahydropyridin-4-yl)quinazoline-2,4-diamine

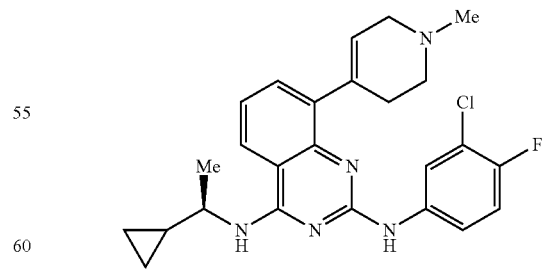

Step A: tert-Butyl (R)-4-(2-((3-chloro-4-fluorophenyl)amino)-4-((1-cyclopropylethyl)amino)quinazolin-8-yl)-3,6-dihydropyridine-1(2H)-carboxylate was prepared according to a procedure analogous to general procedure F using (R)-8-bromo-N²-(3-chloro-4-fluorophenyl)-N⁴-(1-cyclopropylethyl)quinazoline-2,4-diamine, which was prepared according to a procedure analogous to general procedure A.

Step B: A solution of tert-butyl (R)-4-(2-((3-chloro-4-fluorophenyl)amino)-4-((1-cyclopropylethyl)amino)quinazolin-8-yl)-3,6-dihydropyridine-1(2H)-carboxylate (74 mg, 0.138 mmol, 1 equiv.) in THF (1.4 mL, 0.1M) was cooled to 0° C. before addition of LiAlH$_4$ (16 mg, 0.413 mmol, 3 equiv.). The mixture was then heated to 60° C. and stirred for 1 h. Upon completion of the reaction, the mixture was cooled to 0° C. and slowly quenched by the sequential addition of 16 µL of H$_2$O, 16 µL of a 3 M aqueous solution of NaOH, and 48 µL of H$_2$O. The suspension was warmed to room temperature and stirred for 15 min, then filtered over Celite. The filter cake was washed with EtOAc. The filtrate was collected, dried over Na$_2$SO$_4$, and concentrated in vacuo. The residue was purified by reverse phase preparative HPLC (20-60% MeCN in H$_2$O) to provide the title compound as a white solid (27 mg, 35% yield). $^1$H NMR (400 MHz, CDCl$_3$) δ 8.62 (s, 1H), 8.22 (d, J=7.9 Hz, 1H), 7.87 (dd, J=6.6, 2.6 Hz, 1H), 7.50 (d, J=7.3 Hz, 1H), 7.27 (m, 2H), 7.12 (t, J=8.7 Hz, 1H), 5.80 (s, 1H), 3.95 (s, 2H), 3.77 (m, 2H), 3.58 (dd, J=10.9, 5.7 Hz, 1H), 3.05 (m, 1H), 2.99 (s, 3H), 2.51 (d, J=17.1 Hz, 1H), 1.41 (d, J=6.5 Hz, 3H), 1.18 (m, 1H), 0.61 (m, 1H), 0.52 (m, 1H), 0.30 (m, 2H). MS (ESI) m/z=452.10 (M+H)$^+$. LCMS Ret time (UV 214/254): 1.388 min.

Example 121: (R)—N$^2$-(cyclohexylmethyl)-N$^4$-(1-cyclopropylethyl)-8-(1-methyl-1,2,3,6-tetrahydropyridin-4-yl)quinazoline-2,4-diamine

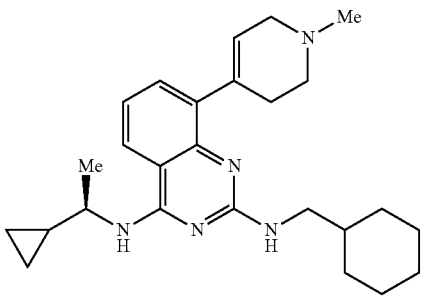 [SMILES: C[C@@H](Nc1nc(NCC2CCCCC2)nc2c(C3=CCN(C)CC3)cccc12)C1CC1]

The title compound was obtained according to a procedure analogous to example 119, which was prepared using a procedure analogous to general procedure F, using (R)-8-bromo-N$^2$-(cyclohexylmethyl)-N$^4$-(1-cyclopropylethyl)quinazoline-2,4-diamine, which was prepared by a procedure analogous to general procedure A. $^1$H NMR (400 MHz, CDCl$_3$) δ 9.03 (s, 1H), 7.90 (d, J=7.7 Hz, 1H), 7.49 (d, J=7.2 Hz, 1H), 7.26 (app t, J=7.3 Hz, 1H), 5.77 (s, 1H), 3.94 (s, 2H), 3.84 (m, 2H), 3.57 (d, J=5.4 Hz, 2H), 3.31 (m, 2H), 3.03 (m, 4H), 2.47 (d, J=15.9 Hz, 1H), 1.76 (m, 4H), 1.64 (m, 2H), 1.42 (d, J=6.6 Hz, 3H), 1.19 (m, 3H), 0.95 (m, 2H), 0.67 (m, 1H), 0.58 (m, 1H), 0.37 (m, 2H). MS (ESI) m/z=420.30 (M+H)$^+$. LCMS Ret time (UV 214/254): 1.395 min.

Example 122: (R)—N$^2$-(3-chloro-4-fluorophenyl)-N$^4$-(1-cyclopropylethyl)-8-(3,6-dihydro-2H-pyran-4-yl)quinazoline-2,4-diamine

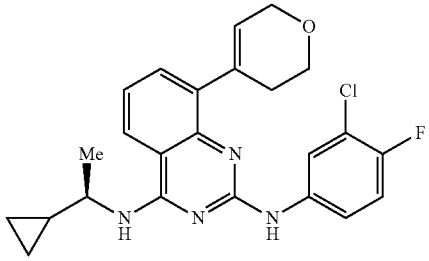 [SMILES: C[C@@H](Nc1nc(Nc2ccc(F)c(Cl)c2)nc2c(C3=CCOCC3)cccc12)C1CC1]

The title compound was prepared according to a procedure analogous to general procedure F using (R)-8-bromo-N$^2$-(3-chloro-4-fluorophenyl)-N$^4$-(1-cyclopropylethyl)quinazoline-2,4-diamine, which was prepared according to a procedure analogous to general procedure A. $^1$H NMR (400 MHz, CDCl$_3$) δ 7.91 (dd, J=6.6, 2.6 Hz, 1H), 7.73 (d, J=7.8 Hz, 1H), 7.57 (d, J=6.8 Hz, 1H), 7.37 (t, J=7.8 Hz, 1H), 7.32 (ddd, J=8.9, 4.0, 2.7 Hz, 1H), 7.09 (t, J=8.7 Hz, 1H), 7.00 (d, J=7.4 Hz, 1H), 5.97 (s, 1H), 4.36 (d, J=2.6 Hz, 2H), 4.10 (t, J=5.4 Hz, 2H), 3.78 (m, 1H), 2.42 (d, J=1.8 Hz, 2H), 1.41 (d, J=6.6 Hz, 3H), 1.08 (m, 1H), 0.68 (m, 1H), 0.55 (m, 1H), 0.36 (m, 2H). MS (ESI) m/z=439.10 (M+H)$^+$. LCMS Ret time (UV 214/254): 1.518 min.

Example 123: (R)—N$^2$-(3-chloro-4-fluorophenyl)-N$^4$-(1-cyclopropylethyl)-8-(2-ethoxyethyl)quinazoline-2,4-diamine

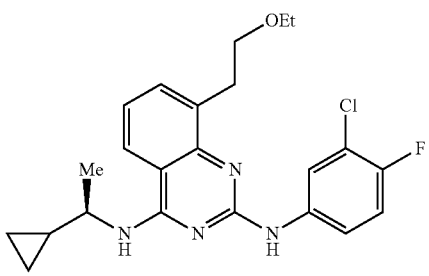 [SMILES: CCOCCc1cccc2c(N[C@H](C)C3CC3)nc(Nc3ccc(F)c(Cl)c3)nc12]

Step A: (R,E)-N$^2$-(3-Chloro-4-fluorophenyl)-N$^4$-(1-cyclopropylethyl)-8-(2-ethoxyvinyl)quinazoline-2,4-diamine, was prepared according to a procedure analogous to general procedure F using (R)-8-bromo-N$^2$-(3-chloro-4-fluorophenyl)-N$^4$-(1-cyclopropylethyl)quinazoline-2,4-diamine, which was prepared according to a procedure analogous to general procedure A.

Step B: The title compound was prepared by hydrogenation of (R,E)-N$^2$-(3-Chloro-4-fluorophenyl)-N$^4$-(1-cyclopropylethyl)-8-(2-ethoxyvinyl)quinazoline-2,4-diamine with 5% Pt/C in 1:1 mix of EtOAc/MeOH. $^1$H NMR (400 MHz, CD$_3$OD) δ 8.19 (d, J=7.8 Hz, 1H), 7.95 (dd, J=6.6, 2.3 Hz, 1H), 7.77 (d, J=7.2 Hz, 1H), 7.46 (t, J=7.8 Hz, 1H), 7.34 (m, 2H), 3.85 (m, 1H), 3.77 (t, J=5.8 Hz, 2H), 3.49 (q, J=7.0 Hz, 2H), 3.14 (t, J=5.8 Hz, 2H), 1.44 (d, J=6.7 Hz, 3H), 1.20 (m, 1H), 1.12 (t, J=7.0 Hz, 3H), 0.67 (m, 1H), 0.54 (m, 1H), 0.34 (m, 2H). MS (ESI) m/z=429.10 (M+H)$^+$. LCMS Ret time (UV 214/254): 1.589 min.

Example 124: (R)—N²-(3-chloro-4-fluorophenyl)-N⁴-(1-cyclopropylethyl)-8-morpholinoquinazoline-2,4-diamine

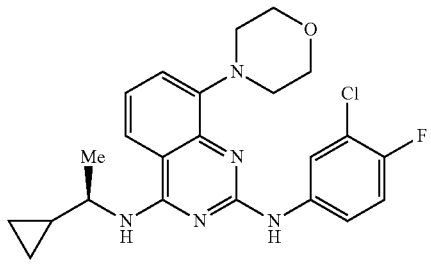 [SMILES: C[C@@H](Nc1nc(Nc2ccc(F)c(Cl)c2)nc2c(N3CCOCC3)cccc12)C1CC1]

The title compound was prepared according to a procedure analogous to general procedure H, using (R)-8-bromo-N²-(3-chloro-4-fluorophenyl)-N⁴-(1-cyclopropylethyl)quinazoline-2,4-diamine, which was prepared according to a procedure analogous to general procedure A. ¹H NMR (400 MHz, CD₃OD) δ 8.09 (dd, J=8.3, 1.0 Hz, 1H), 8.01 (d, J=7.0 Hz, 1H), 7.81 (dd, J=7.8, 0.9 Hz, 1H), 7.50 (t, J=8.1 Hz, 1H), 7.35 (dd, J=6.1, 1.6 Hz, 2H), 3.95 (d, J=8.3 Hz, 4H), 3.86 (m, 1H), 3.00 (m, 4H), 1.46 (d, J=6.7 Hz, 3H), 1.20 (m, 1H), 0.67 (td, J=8.0, 4.0 Hz, 1H), 0.55 (m, 1H), 0.34 (m, 2H). MS (ESI) m/z=442.00 (M+H)⁺. LCMS Ret time (UV 214/254): 1.629 min.

Example 125: (R)—N²-(cyclohexylmethyl)-N⁴-(1-cyclopropylpropyl)-8-(1,2,3,6-tetrahydropyridin-4-yl)quinazoline-2,4-diamine

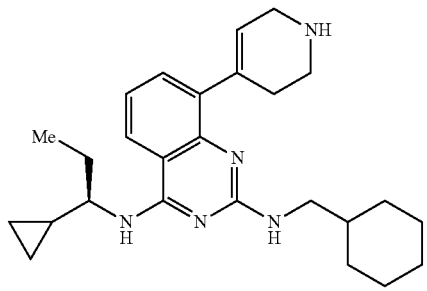 [SMILES: CC[C@@H](Nc1nc(NCC2CCCCC2)nc2c(C3=CCNCC3)cccc12)C1CC1]

The title compound was obtained according to a procedure analogous to general procedure F, using (R)-8-bromo-N-(cyclohexylmethyl)-N⁴-(1-cyclopropylpropyl)quinazoline-2,4-diamine, which was prepared by a procedure analogous to general procedure A using (R)-1-cyclopropylpropan-1-amine hydrochloride, which was prepared by a procedure analogous to general procedure B. ¹H NMR (400 MHz, CD₃OD) δ 9.07 (d, J=8.2 Hz, 1H), 8.20 (dd, J=8.2, 1.1 Hz, 1H), 7.63 (dd, J=7.4, 1.0 Hz, 1H), 7.43 (t, J=7.8 Hz, 1H), 5.96 (m, 1H), 3.89 (m, 2H), 3.81 (m, 1H), 3.56 (t, J=6.1 Hz, 2H), 3.34 (app qd, J=12.2, 5.5 Hz, 2H), 2.71 (m, 2H), 1.90 (m, 2H), 1.78 (m, 4H), 1.65 (m, 2H), 1.26 (m, 3H), 1.16 (m, 1H), 1.02 (t, J=7.4 Hz, 3H), 1.02 (m, 2H), 0.71 (m, 1H), 0.51 (m, 1H), 0.36 (m, 2H). MS (ESI) m/z=420.10 (M+H)⁺. LCMS Ret time (UV 214/254): 1.757 min.

Example 126: (R)—N⁴-(1-cyclopropylpropyl)-N²-(3-fluoro-5-methylphenyl)-8-(1,2,3,6-tetrahydropyridin-4-yl)quinazoline-2,4-diamine

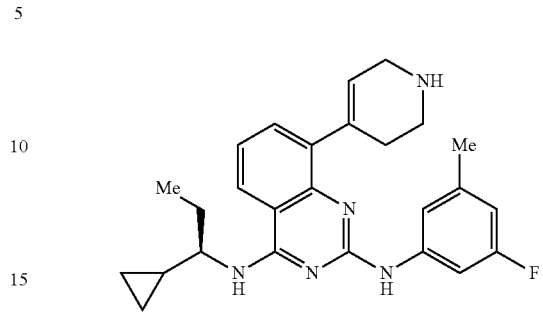

The title compound was obtained according to a procedure analogous to general procedure F, using (R)-8-bromo-N⁴-(1-cyclopropylpropyl)-N²-(3-fluoro-5-methylphenyl)quinazoline-2,4-diamine, which was prepared by a procedure analogous to general procedure A using (R)-1-cyclopropylpropan-1-amine hydrochloride, which was prepared by a procedure analogous to general procedure B. ¹H NMR (400 MHz, CD₃OD) δ 8.28 (dd, J=8.2, 1.1 Hz, 1H), 7.71 (dd, J=7.5, 1.1 Hz, 1H), 7.52 (m, 1H), 7.30 (dt, J=10.8, 2.0 Hz, 1H), 7.15 (s, 1H), 6.82 (d, J=9.3 Hz, 1H), 6.02 (m, 1H), 3.91 (m, 2H), 3.74 (dt, J=9.3, 7.1 Hz, 1H), 3.60 (t, J=6.1 Hz, 2H), 2.76 (m, 2H), 2.38 (s, 3H), 1.88 (m, 2H), 1.16 (m, 1H), 1.01 (t, J=7.5 Hz, 3H), 0.70 (m, 1H), 0.50 (m, 1H), 0.32 (m, 2H). MS (ESI) m/z=432.10 (M+H)⁺. LCMS Ret time (UV 214/254): 1.540 min.

Example 127: (R)-8-(2-aminoethyl)-N²-(cyclohexylmethyl)-N⁴-(1-cyclopropylpropyl)quinazoline-2,4-diamine

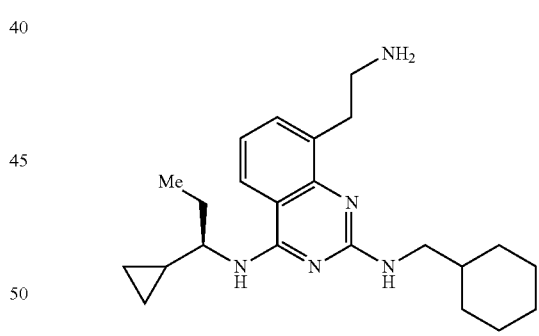

The title compound was obtained according to a procedure analogous to general procedure E, using (R)-8-bromo-N²-(cyclohexylmethyl)-N⁴-(1-cyclopropylpropyl)quinazoline-2,4-diamine, which was prepared by a procedure analogous to general procedure A using (R)-1-cyclopropylpropan-1-amine hydrochloride, which was prepared by a procedure analogous to general procedure B. ¹H NMR (400 MHz, CD₃OD) δ 9.06 (d, J=7.8 Hz, 1H), 8.18 (dd, J=8.2, 0.9 Hz, 1H), 7.71 (d, J=6.8 Hz, 1H), 7.39 (t, J=7.8 Hz, 1H), 3.81 (m, 1H), 3.37 (app qd, J=11.9, 5.2 Hz, 2H), 3.23 (m, 4H), 1.90 (m, 2H), 1.79 (t, J=12.9 Hz, 4H), 1.67 (m, 2H), 1.27 (m, 3H), 1.16 (m, 1H), 1.04 (m, 2H), 1.02 (t, J=7.5 Hz, 3H), 0.71 (m, 1H), 0.51 (m, 1H), 0.36 (n, 2H). MS (ESI) m/z=382.20 (M+H)⁺. LCMS Ret time (UV 214/254): 1.561 min.

Example 128: (R)-8-(2-aminoethyl)-N⁴-(1-cyclopropylpropyl)-N²-(3-fluoro-5-methylphenyl)quinazoline-2,4-diamine

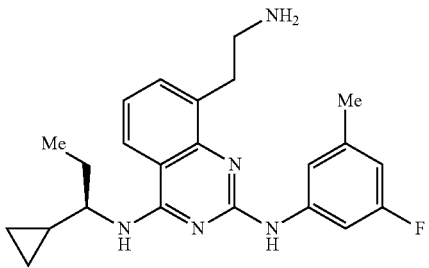 [SMILES: CC[C@@H](Nc1nc(Nc2cc(C)cc(F)c2)nc2c(CCN)cccc12)C1CC1]

The title compound was obtained according to a procedure analogous to general procedure E, using (R)-8-bromo-N⁴-(1-cyclopropylpropyl)-N²-(3-fluoro-5-methylphenyl)quinazoline-2,4-diamine, which was prepared by a procedure analogous to general procedure A using (R)-1-cyclopropylpropan-1-amine hydrochloride, which was prepared by a procedure analogous to general procedure B. $^1$H NMR (400 MHz, CD$_3$OD) δ 8.26 (dd, J=8.3, 1.0 Hz, 1H), 7.79 (d, J=6.7 Hz, 1H), 7.48 (m, 1H), 7.36 (dt, J=10.7, 1.8 Hz, 1H), 7.18 (s, 1H), 6.81 (d, J=9.3 Hz, 1H), 3.76 (dt, J=9.3, 7.1 Hz, 1H), 3.25 (m, 4H), 2.39 (s, 3H), 1.89 (m, 2H), 1.16 (m, 1H), 1.02 (t, J=7.5 Hz, 3H), 0.72 (m, 1H), 0.50 (m, 1H), 0.33 (m, 2H). MS (ESI) m/z=394.20 (M+H)⁺. LCMS Ret time (UV 214/254): 1.441 min.

Example 129: (R)—N²-(3-chloro-2-fluorobenzyl)-N⁴-(3,3-dimethylbutan-2-yl)-8-(1,2,3,6-tetrahydropyridin-4-yl)quinazoline-2,4-diamine

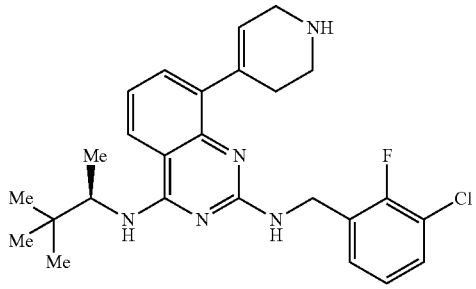 [SMILES: C[C@@H](Nc1nc(NCc2cccc(Cl)c2F)nc2c(C3=CCNCC3)cccc12)C(C)(C)C]

The title compound was prepared according to a procedure analogous to general procedure F, using (R)-8-bromo-N²-(3-chloro-4-fluorobenzyl)-N⁴-(3,3-dimethylbutan-2-yl)quinazoline-2,4-diamine, which was obtained according to a procedure analogous to general procedure A. $^1$H NMR (400 MHz, CD$_3$OD) δ 8.53 (d, J=9.2 Hz, 1H), 8.23 (dd, J=8.3, 1.1 Hz, 1H), 7.65 (dd, J=7.4, 1.1 Hz, 1H), 7.44 (t, J=8.1 Hz, 1H), 7.38 (m, 2H), 7.14 (td, J=7.9, 0.8 Hz, 1H), 5.97 (m, 1H), 4.78 (dd, J=39.9, 15.2 Hz, 2H), 4.57 (m, 1H), 3.90 (m, 2H), 3.59 (t, J=6.1 Hz, 2H), 2.71 (m, 2H), 1.21 (d, J=6.9 Hz, 3H), 0.92 (s, 9H). MS (ESI) m/z=468.10 (M+H)⁺. LCMS Ret time (UV 214/254): 1.426 min.

Example 130: (R)-8-(aminomethyl)-N²-(3-chloro-4-fluorophenyl)-N⁴-(3,3-dimethylbutan-2-yl)quinazoline-2,4-diamine

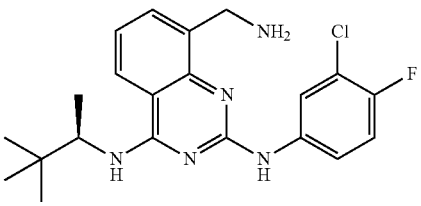 [SMILES: C[C@@H](Nc1nc(Nc2ccc(F)c(Cl)c2)nc2c(CN)cccc12)C(C)(C)C]

The title compound was obtained according to a procedure analogous to general procedure E, using (R)-8-bromo-N⁴-(1-cyclopropylpropyl)-N²-(3-fluoro-5-methylphenyl)quinazoline-2,4-diamine, which was prepared by a procedure analogous to general procedure A. $^1$H NMR (400 MHz, CD$_3$OD) δ 8.39 (d, J=7.5 Hz, 1H), 8.09 (dd, J=6.7, 2.6 Hz, 1H), 7.90 (d, J=7.1 Hz, 1H), 7.47 (m, 2H), 7.30 (t, J=8.9 Hz, 1H), 4.60 (q, J=6.9 Hz, 1H), 4.54 (s, 2H), 1.31 (d, J=6.9 Hz, 3H), 1.02 (s, 9H). MS (ESI) m/z=402.10 (M+H)⁺. LCMS Ret time (UV 214/254): 1.340 min.

Example 131: (R)-8-(aminomethyl)-N⁴-(3,3-dimethylbutan-2-yl)-N²-(3-fluoro-5-methylphenyl)quinazoline-2,4-diamine

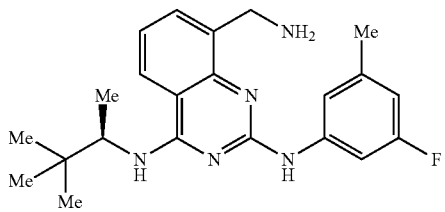 [SMILES: Cc1cc(F)cc(Nc2nc(N[C@H](C)C(C)(C)C)c3cccc(CN)c3n2)c1]

Step A: (R)-4-((3,3-dimethylbutan-2-yl)amino)-2-((3-fluoro-5-methylphenyl)amino)quinazoline-8-carbonitrile was prepared according to a procedure analogous to general procedure J from (R)-8-bromo-N⁴-(1-cyclopropylpropyl)-N²-(3-fluoro-5-methylphenyl)quinazoline-2,4-diamine, which was prepared by a procedure analogous to general procedure A.

Step B: The title compound was prepared according to a procedure analogous to general procedure K using (R)-4-((3,3-dimethylbutan-2-yl)amino)-2-((3-fluoro-5-methylphenyl)amino)quinazoline-8-carbonitrile. $^1$H NMR (400 MHz, CD$_3$OD) δ 8.41 (dd, J=8.3, 1.0 Hz, 1H), 7.92 (d, J=6.7 Hz, 1H), 7.51 (t, J=7.9 Hz, 1H), 7.47 (dt, J=11.0, 1.9 Hz, 1H), 7.26 (s, 1H), 6.80 (d, J=9.4 Hz, 1H), 4.66 (q, J=6.9 Hz, 1H), 4.54 (s, 2H), 2.40 (s, 3H), 1.32 (d, J=6.9 Hz, 3H), 1.03 (s, 9H). MS (ESI) m/z=382.20 (M+H)⁺. LCMS Ret time (UV 214/254): 1.309 min.

Example 132: (R)-8-(aminomethyl)-$N^2$-(3-chloro-4-fluorophenyl)-$N^4$-(1-(thiophen-2-yl)ethyl)quinazoline-2,4-diamine

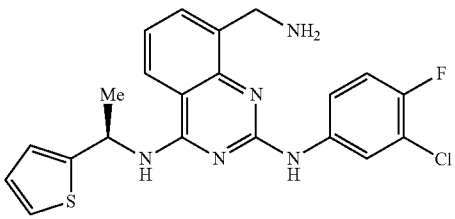 [SMILES: C[C@@H](Nc1nc(Nc2ccc(F)c(Cl)c2)nc2c(CN)cccc12)c1cccs1]

Step A: (R)-2-((3-chloro-4-fluorophenyl)amino)-4-((1-(thiophen-2-yl)ethyl)amino)quinazoline-8-carbonitrile was obtained according to a procedure analogous to general procedure J from (R)-8-bromo-$N^2$-(3-chloro-2-fluorophenyl)-$N^4$-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B.
Step B: The title compound was obtained from (R)-2-((3-chloro-4-fluorophenyl)amino)-4-((1-(thiophen-2-yl)ethyl)amino)quinazoline-8-carbonitrile according to a procedure analogous to general procedure K. $^1$H NMR (400 MHz, $CD_3OD$) δ 8.31 (d, J=8.3 Hz, 1H), 7.90 (dd, J=6.6, 2.6 Hz, 1H), 7.85 (d, J=7.3 Hz, 1H), 7.50 (ddd, J=9.0, 4.0, 2.8 Hz, 1H), 7.43 (t, J=7.8 Hz, 1H), 7.28 (dd, J=5.1, 1.0 Hz, 1H), 7.23 (t, J=8.9 Hz, 1H), 7.05 (d, J=3.5 Hz, 1H), 6.96 (dd, J=5.0, 3.6 Hz, 1H), 5.90 (q, J=6.8 Hz, 1H), 4.51 (m, 2H), 1.79 (d, J=7.0 Hz, 3H). MS (ESI) m/z=428.10 $(M+H)^+$. LCMS Ret time (UV 214/254): 1.263 min.

Example 133: (R)—$N^2$-(3-chloro-2-fluorobenzyl)-8-(1,2,3,6-tetrahydropyridin-4-yl)-$N^4$-(1-(thiophen-2-yl)ethyl)quinazoline-2,4-diamine

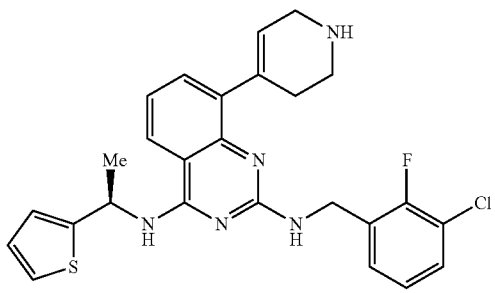 [SMILES: C[C@@H](Nc1nc(NCc2cccc(Cl)c2F)nc2c(C3=CCNCC3)cccc12)c1cccs1]

The title compound was obtained according to a procedure analogous to general procedure F, using (R)-8-bromo-$N^2$-(3-chloro-2-fluorobenzyl)-$N^4$-(1-(thiophen-2-yl)ethyl)quinazoline-2,4-diamine, which was prepared by a procedure analogous to general procedure A using (R)-1-(thiophen-2-yl)ethan-1-amine hydrochloride, which was prepared by a procedure analogous to general procedure B. $^1$H NMR (400 MHz, $CD_3OD$) δ 9.54 (d, J=7.6 Hz, 1H), 8.21 (dd, J=8.3, 1.2 Hz, 1H), 7.66 (dd, J=7.5, 1.2 Hz, 1H), 7.44 (t, J=7.7 Hz, 1H), 7.38 (m, 1H), 7.29 (m, 1H), 7.27 (dd, J=5.1, 1.2 Hz, 1H), 7.08 (td, J=7.9, 1.0 Hz, 1H), 7.02 (m, 1H), 6.94 (dd, J=5.1, 3.6 Hz, 1H), 5.95 (m, 2H), 4.82 (d, J=1.8 Hz, 2H), 3.89 (m, 2H), 3.57 (t, J=6.1 Hz, 2H), 2.71 (m, 2H), 1.75 (d, J=7.0 Hz, 3H). MS (ESI) m/z=494.20 $(M+H)^+$. LCMS Ret time (UV 214/254): 1.293 min.

Biological Examples

Compounds of the present invention were assessed for their ability to affect the function of Ras in biochemical and cell proliferation assays.

A. SOS-Mediated Nucleotide Exchange on Ras

Compounds of the present invention were tested for their ability to modify the rate at which Ras exchanges a labeled nucleotide guanosine diphosphate (GDP) analog for guanosine triphosphate (GTP). Briefly, test compounds, then GTP and the Ras GEF SOS (Son of Sevenless) are added to a buffered solution containing Ras protein loaded with BODIPY-GDP. Changes in fluorescence indicating exchange of the labeled GDP for GTP are monitored over time. Raw fluorescence data was fit to a single exponential decay function and derived rates were plotted as mean values. $EC_{50}$ values were calculated by plotting mean derived rates as a function of compound concentration and fit using a four-parameter dose-response curve. Full assay details are disclosed in: Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" *Proc. Natl. Acad. Sci.* 2014; 11(9): 3401-3406. PMCID: PMC3948241. Many of the exemplified compounds Examples 1-133 were run in the recited assay and the results are reported in the following Table 1. In the following table:

"+" indicates no nucleotide exchange $EC_{50}$ measurement less than 30 µM

"++" indicates at least one nucleotide exchange $EC_{50}$ measurement less than 30 µM but no measurement less than 5 µM; and "+++" indicates at least one nucleotide exchange $EC_{50}$ measurement less than 5 µM but no measurement less than 1 µM; and "++++" indicates at least one nucleotide exchange $EC_{50}$ measurement less than 1 µM.

TABLE 1

Nucleotide exchange activity for example compounds

| Example | Activity |
| --- | --- |
| 1 | ++ |
| 2 | +++ |
| 3 | +++ |
| 4 | +++ |
| 5 | ++ |
| 6 | ++ |
| 7 | ++ |
| 8 | ++ |
| 9 | ++++ |
| 10 | ++ |
| 11 | + |
| 12 | ++ |
| 13 | ++ |
| 14 | +++ |
| 15 | ++ |
| 16 | ++ |
| 17 | ++ |
| 18 | + |
| 19 | ++ |
| 20 | ++ |
| 21 | +++ |
| 22 | + |

TABLE 1-continued

Nucleotide exchange activity for example compounds

| Example | Activity |
|---|---|
| 23 | +++ |
| 24 | +++ |
| 25 | +++ |
| 26 | +++ |
| 27 | ++ |
| 28 | ++ |
| 29 | ++ |
| 30 | ++ |
| 31 | +++ |
| 32 | +++ |
| 33 | ++ |
| 34 | ++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | + |
| 45 | + |
| 46 | + |
| 50 | +++ |
| 51 | +++ |
| 52 | +++ |
| 53 | ++ |
| 54 | + |
| 55 | + |
| 56 | +++ |
| 57 | +++ |
| 58 | ++ |
| 59 | ++ |
| 60 | +++ |
| 61 | +++ |
| 62 | ++++ |
| 63 | + |
| 64 | +++ |
| 65 | ++ |
| 66 | ++ |
| 67 | ++ |
| 68 | +++ |
| 69 | + |
| 70 | + |
| 71 | ++ |
| 72 | ++ |
| 73 | +++ |
| 74 | +++ |
| 75 | ++ |
| 76 | +++ |
| 77 | +++ |
| 78 | +++ |
| 79 | ++ |
| 80 | +++ |
| 81 | +++ |
| 82 | ++ |
| 83 | +++ |
| 84 | ++ |
| 85 | ++ |
| 86 | ++ |
| 87 | ++ |
| 88 | +++ |
| 89 | +++ |
| 90 | +++ |
| 91 | ++ |
| 92 | ++ |
| 93 | ++ |
| 94 | +++ |
| 95 | ++ |
| 96 | +++ |
| 97 | ++ |
| 98 | ++ |
| 99 | +++ |
| 100 | ++ |
| 101 | ++ |
| 102 | ++ |
| 103 | ++ |
| 104 | +++ |
| 105 | +++ |
| 106 | ++++ |
| 107 | +++ |
| 108 | +++ |
| 109 | +++ |
| 110 | ++ |
| 111 | ++ |
| 112 | +++ |
| 113 | +++ |
| 114 | +++ |
| 115 | +++ |
| 116 | +++ |
| 117 | +++ |
| 118 | +++ |
| 119 | +++ |
| 120 | ++ |
| 121 | +++ |
| 122 | + |
| 123 | + |
| 124 | ++ |
| 125 | ++++ |
| 126 | +++ |
| 127 | +++ |
| 128 | +++ |
| 129 | ++ |
| 130 | ++ |
| 131 | ++ |
| 132 | ++ |
| 133 | ++ |

B. Binding to SOS

Compounds of the present invention were tested for their ability to the Ras guanine exchange factor (GEF) Son of Sevenless (SOS). Binding to SOS was measured using a Fluorescence polarization anisotropy (FPA) assay that assesses the ability of a test compound to displace a fluorescent FITC-conjugated compound. Briefly, the labeled probe compound is incubated with SOS in buffer. Changes in anisotropy indicative of displacement of the labeled probe for a test compound are assessed over a dose range of test compound. Data was analyzed by plotting fluorescence anisotropy values as a function of compound concentration. $IC_{50}$ values were determined using a four-parameter dose-response (variable slope) and binding affinities were calculated from this $IC_{50}$ value. This assay is performed in a method analogous to the assay disclosed in: Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" *Proc. Natl. Acad. Sci.* 2014; 11(9): 3401-3406. PMCID: PMC3948241.

Many of the exemplified compounds Examples 1-133 were run in the recited assay and the results are reported in the following Table 2. In the following table:

"+" indicates no binding affinity measurement less than 5 µM

"++" indicates at least one binding affinity measurement less than 5 µM but no measurement less than 1 µM; and "+++" indicates at least one binding affinity measurement less than 1 µM.

TABLE 2

Binding affinities for example compounds

| Example | Activity |
|---|---|
| 2 | + |
| 3 | + |
| 4 | + |
| 5 | + |
| 9 | + |
| 14 | + |
| 19 | + |
| 21 | + |
| 22 | + |
| 23 | + |
| 24 | + |
| 27 | + |
| 32 | + |
| 34 | + |
| 35 | + |
| 36 | + |
| 37 | + |
| 38 | + |
| 39 | + |
| 40 | + |
| 42 | + |
| 51 | +++ |
| 52 | ++ |
| 53 | + |
| 54 | + |
| 55 | + |
| 56 | + |
| 57 | + |
| 58 | + |
| 59 | + |
| 60 | ++ |
| 62 | ++ |
| 63 | + |
| 64 | ++ |
| 65 | + |
| 66 | + |
| 67 | + |
| 68 | + |
| 69 | + |
| 70 | + |
| 71 | + |
| 72 | + |
| 73 | ++ |
| 74 | ++ |
| 75 | + |
| 76 | ++ |
| 77 | +++ |
| 78 | + |
| 81 | + |
| 82 | + |
| 84 | ++ |
| 85 | ++ |
| 86 | + |
| 87 | + |
| 89 | ++ |
| 90 | ++ |
| 91 | ++ |
| 92 | + |
| 93 | +++ |
| 94 | ++ |
| 95 | + |
| 97 | + |
| 98 | ++ |
| 101 | + |
| 102 | + |
| 103 | + |
| 104 | ++ |
| 105 | ++ |
| 106 | ++ |
| 107 | ++ |
| 108 | ++ |
| 111 | + |
| 112 | + |
| 113 | ++ |
| 114 | ++ |
| 115 | ++ |
| 116 | +++ |
| 117 | +++ |
| 118 | ++ |
| 119 | ++ |
| 120 | ++ |
| 121 | ++ |
| 122 | + |
| 123 | + |
| 124 | + |
| 125 | +++ |
| 126 | +++ |
| 127 | +++ |
| 128 | ++ |
| 130 | + |
| 131 | + |
| 132 | ++ |
| 133 | ++ |

C. Inhibition of Cancer Cell Proliferation

Compounds of the present invention were measured for their ability to kill H727 lung cancer cell lines, which contain a G12V K-Ras mutation. Cell proliferation experiments were conducted in 96-well plates. Cells were plated at 1000 cells/well, incubated overnight, followed by treatment with a dose range of compound for 3 days at 37° C. Cell proliferation was assessed using a CellTiter-Glo assay (Promega) according to the manufacturer's protocol. Data were normalized to DMSO control. $IC_{50}$ values were determined using a four-parameter dose-response (variable slope) equation. These assays are performed in a manner analogous to the assay disclosed in: Burns, M. C.; Sun, Q.; Daniels, R. N.; Camper, D. V.; Kennedy, J. P.; Phan, J.; Olejniczak, E. O.; Lee, T.; Waterson, A. G.; Rossanese, O. W.; Fesik, S. W. "Approach for targeting Ras with small molecules that activate SOS-mediated nucleotide exchange" *Proc. Natl. Acad. Sci.* 2014; 11(9): 3401-3406. PMCID: PMC3948241. Many of the exemplified compounds Examples 1-133 were run in the recited assay and the results are reported in the following Table 3. In the following table:

"+" indicates no H727 cancer cell line proliferation $IC_{50}$ less than 20 μM

"++" indicates at least one H727 cancer cell line proliferation $IC_{50}$ less than 20 μM but no measurement less than 5 μM; and "+++" indicates at least H727 cancer cell line proliferation $IC_{50}$ less than 5 μM but no measurement less than 1 μM; and "++++" indicates at least H727 cancer cell line proliferation $IC_{50}$ less than 1 μM.

TABLE 3

Cell proliferation activity for example compounds

| Example | Activity |
|---|---|
| 1 | +++ |
| 5 | +++ |
| 22 | + |
| 39 | ++ |
| 50 | +++ |
| 51 | ++++ |
| 57 | +++ |
| 58 | +++ |
| 59 | ++ |
| 64 | ++++ |
| 68 | +++ |
| 69 | +++ |

TABLE 3-continued

Cell proliferation activity for example compounds

| Example | Activity |
|---|---|
| 70 | ++ |
| 71 | +++ |
| 72 | ++ |
| 73 | ++++ |
| 75 | ++++ |
| 76 | ++++ |
| 78 | ++ |
| 98 | +++ |
| 100 | ++++ |
| 101 | +++ |
| 102 | +++ |
| 104 | ++++ |
| 109 | ++++ |
| 110 | ++ |

We claim:

1. A compound of the following formula:

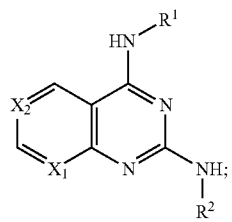

wherein $X_1$ is selected from $C_{1-6}$—$R^A$;
$X_2$ is selected from $C_{1-6}$—$R^B$;
$R^A$ is optionally substituted and selected from

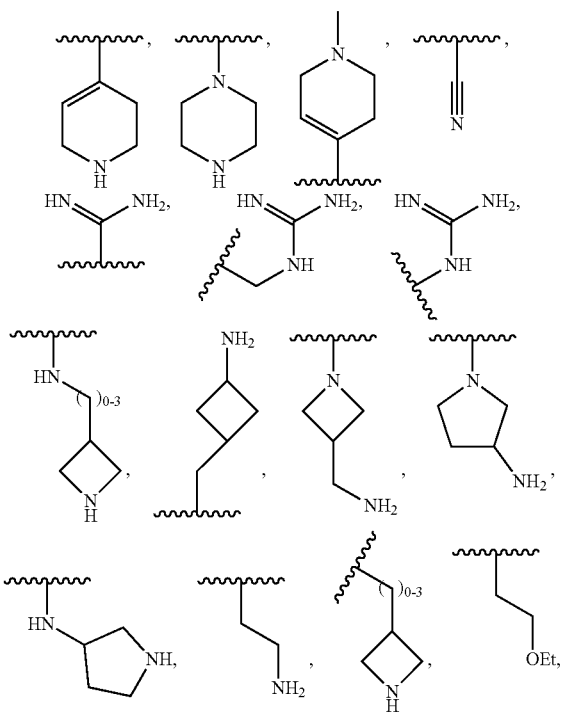

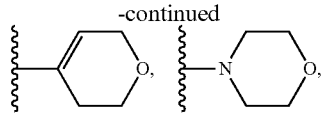

$C_1$-$C_6$ alkylamino, piperazinyl, pyridinyl, $C_1$-$C_6$ alkylalcohol, cycloamino, cycloalkylamino, H, cycloalkenylamino, —$NH_2$, -alkyl$NH_2$, -alkyl-NH-alkyl, —NHMe, —$NMe_2$, —OH, —NH-alkyl-$NH_2$, —NH-alkyl-NHMe, —NH-alkyl-$NMe_2$, —NH-alkyl-OH, bromine, CN;

$R^B$ is optionally substituted with one or more Z and selected from H, alkyl, aminoalkyl, cycloalkyl, alkoxy, halogen, cycloheteroalkyl, aryl, heteroaryl;

provided that $R^A$ and $R^B$ are not both H;

$R^1$ is optionally substituted with one or more Z and selected from alkyl, benzyl, phenyl, cycloalkyl, aryl, heteroaryl, heterocycloalkyl, alkyl-cycloalkyl, alkylaryl, alkyl-heteroaryl, alkenyl-cycloalkyl;

$R^2$ is (i) optionally substituted with one or more Z, and selected from phenyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself; or (ii) benzyl substituted with one or more Z;

Z is independently H, alkyl, halogen, $CF_3$, alkoxy, alkylalkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; provided that when $X^1$ is C—H, $X^2$ is CH, and $R^1$ is furan, $R^2$ is not phenyl and where $X^1$ is C—H, $X^2$ is CH, and $R^1$ is benzyl, $R^2$ is not phenyl.

2. A compound of claim 1 wherein:

$R^1$ is selected from —$(CH_m)_n$-cycloalkyl, —$(CH_m)_n$-heterocycloalkenyl, —$(CH_m)_n$-heteroaryl, or —$(CH_m)_n$-alkyl and optionally substituted with cycloalkyl, methyl, or ethyl;

$R^2$ is selected from —$(CH_2)_n$-cycloalkyl, —$(CH_2)_n$-alkenyl, or $(CH_2)_n$-aryl, and optionally independently substituted with alkyl, cycloalkyl, $CF_3$, one or more halogen such as Cl, F, Br; methyl, or cyano, provided that when $R^2$ is benzyl it is substituted by one or more Z;

m is 1 or 2;

n is 0-3;

$X_2$ is selected from H or ethylaminyl;

or a pharmaceutically acceptable salt thereof or a pharmaceutically acceptable derivative thereof.

3. A compound of claim 1 wherein $R^1$ is optionally substituted and selected from

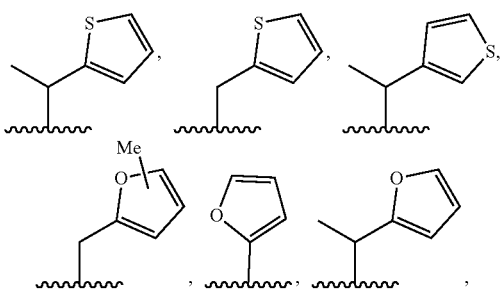

-continued

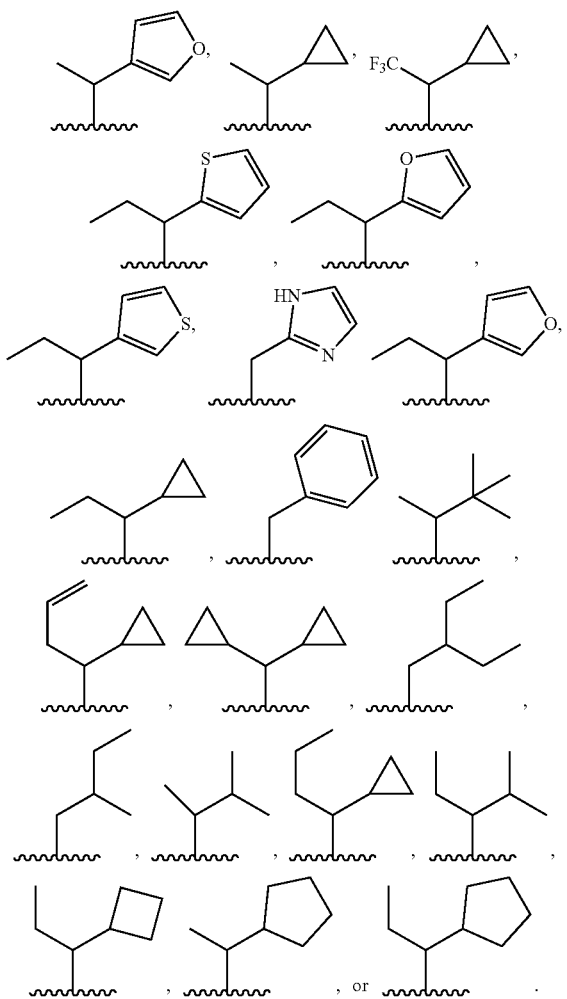

4. A compound of claim 1 wherein $R^2$ is optionally substituted and selected from

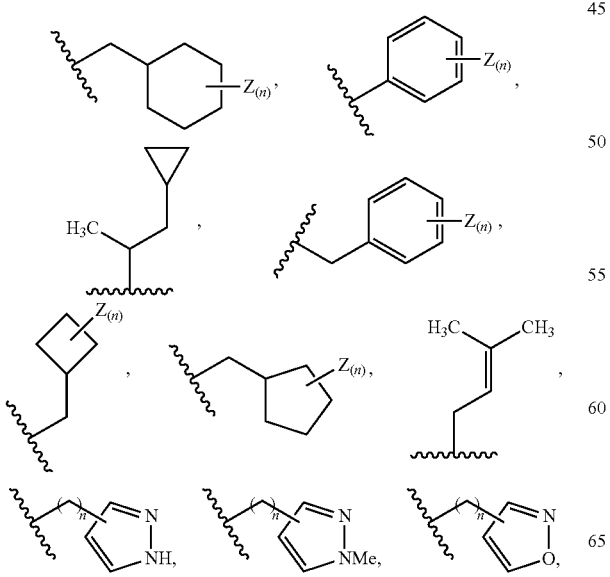

-continued

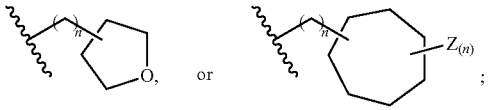

provided that when $R^2$ is benzyl it is substituted by one or more Z;

Z is independently H, Cl, F, Br, cyano, $CF_3$, methoxy, or alkyl, including methyl, ethyl, vinyl, cyclopropyl; or more than one Z joins together to form a 5 or six membered ring;

n is 0-3;

or a pharmaceutically acceptable salt thereof or a pharmaceutically acceptable derivative thereof.

5. A compound of claim 1, wherein $R^2$ and more than one Z together form:

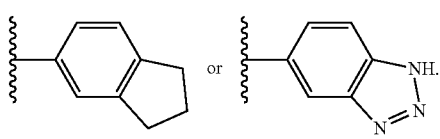

6. A compound of claim 1 wherein $R^4$ is amino.

7. A compound of claim 1 wherein $R^4$ is

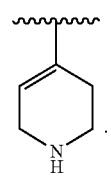 [SMILES: *C1=CCNCC1]

8. A compound of claim 1 wherein $R^4$ is

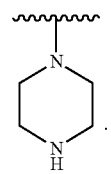

9. A compound of claim 1 wherein $R^1$ is

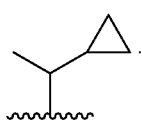 [SMILES: *C(C)C1CC1]

10. A compound of claim 1 wherein $R^1$ is

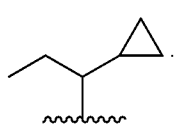 [SMILES: *C(CC)C1CC1]

11. A compound of claim 1 wherein R¹ is

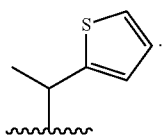 [SMILES: *C(C)c1cccs1]

12. A compound of claim 1 wherein R¹ is

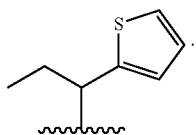 [SMILES: *C(CC)c1cccs1]

13. A compound of claim 1 wherein R¹ is

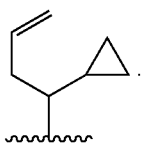 [SMILES: *C(CC=C)C1CC1]

14. A compound of claim 1 wherein R² is

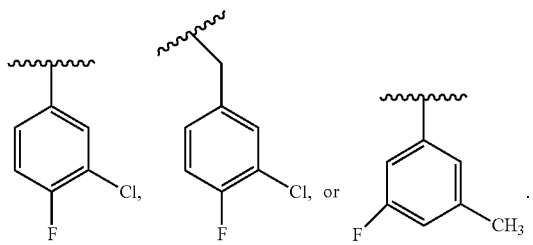

15. A compound of claim 1 wherein R² is

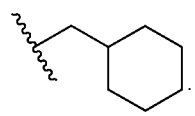

16. A compound of claim 1 wherein R² is

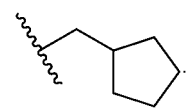 [SMILES: *CC1CCCC1]

17. A method of activating nucleotide exchange on Ras in a patient in need thereof, comprising administering to the patient a Ras nucleotide exchange effective amount of a pharmaceutical composition comprising a compound of claim 1 and a pharmaceutically acceptable carrier.

18. The method of claim 17, wherein the compound binds to SOS.

19. The method of claim 17, wherein the nucleotide exchange on Ras is in a tumor cell.

20. A method of modulating Ras activity in a patient in need thereof, comprising administering to the patient an effective Ras activity modulating amount of a compound of claim 1 or a pharmaceutically acceptable carrier.

21. A method of inhibiting Ras pathway activity in a tumor cell, the method comprising contacting the cell with a compound of claim 1.

22. A method of affecting levels of phosphoERK in a tumor cell, the method comprising contacting the cell with an effective amount of a compound of claim 1.

23. A method of affecting levels of phosphoAkt in a tumor cell, the method comprising contacting the cell with an effective amount of a compound of claim 1.

24. A method of inhibiting the proliferation of cells associated with a malignant or non-malignant disease or pathological state, the method comprising: administering to a patient in need thereof an effective Ras-inhibiting amount of a compound of claim 1.

25. A method of inhibiting proliferation of cells associated with a malignant or non-malignant disease or pathological state, with a compound that affects nucleotide exchange on Ras, the method comprising: administering to a patient in need thereof an effective Ras-modulating amount of a compound of claim 1.

26. A method of modulating angiogenesis, tumor progression, and/or metastasis comprising the step of administering to a tissue or a subject associated with a disease condition a therapeutically effective amount of a compound of claim 1.

27. The method of claim 20, wherein said modulating inhibits angiogenesis, tumor progression, and/or metastasis.

28. The method of claim 24, wherein said inhibition involves inhibiting Ras pathway activity.

29. The method of claim 17, further comprising co-administration with a known anti-cancer medication.

30. A method of inhibiting cell proliferation of cells associated with a malignant disease or pathological state, comprising administering an effective SOS binding amount of a compound of claim 1.

31. The method of claim 30, further comprising co-administration with a known anti-cancer medication.

32. A pharmaceutical composition, comprising a compound of claim 1 a pharmaceutically acceptable carrier.

33. A compound of claim 1 of the following formula:

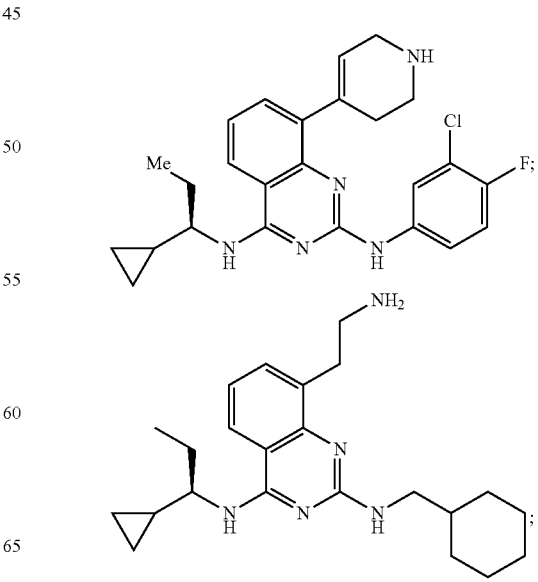

133
-continued
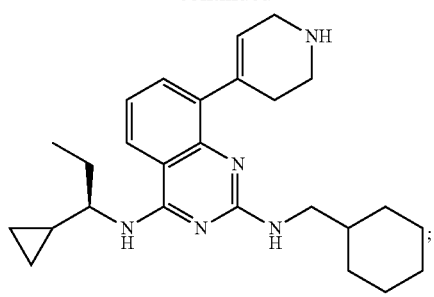
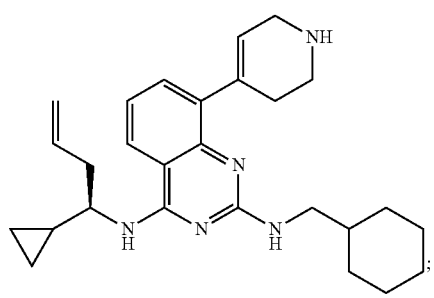
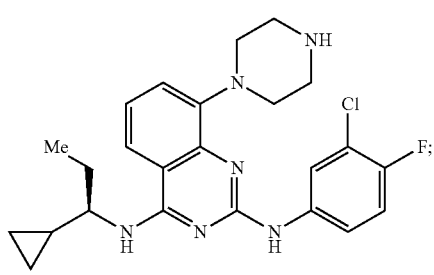
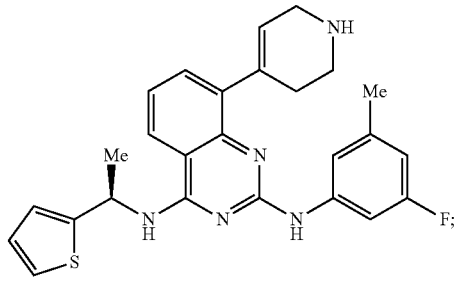
or a pharmaceutically acceptable salt thereof.
34. A compound of claim 1, of the following formula:
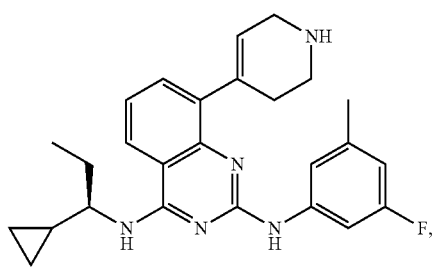
-continued
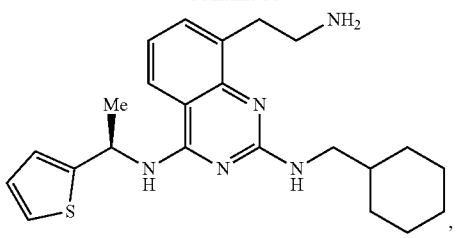
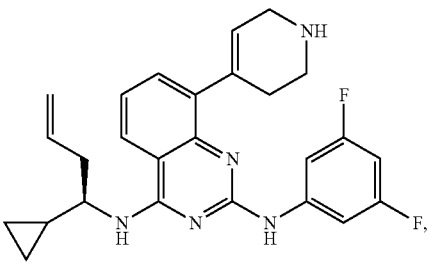
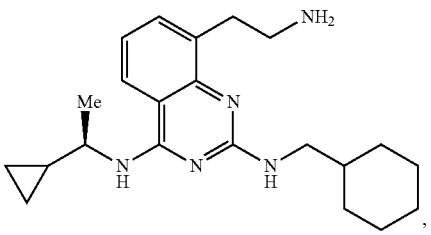
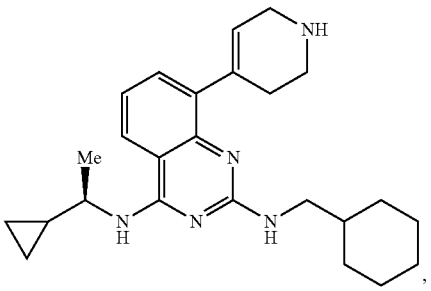
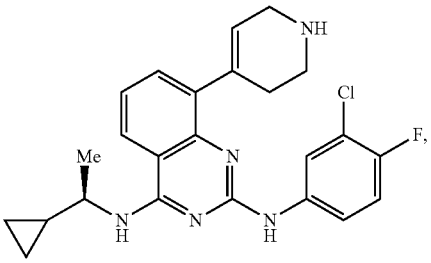

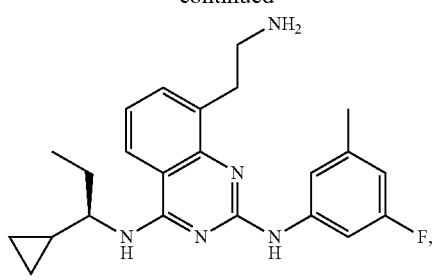
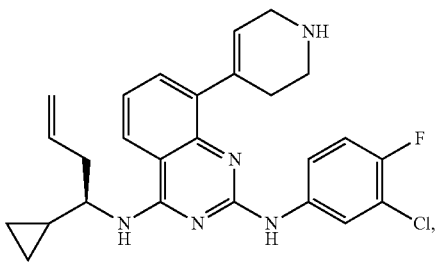
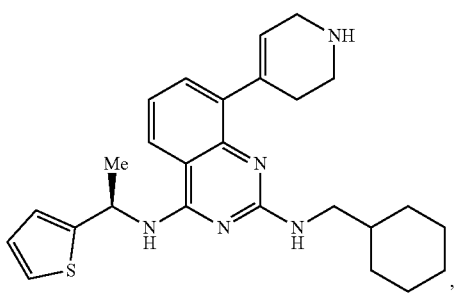
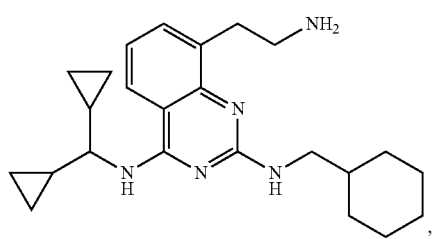
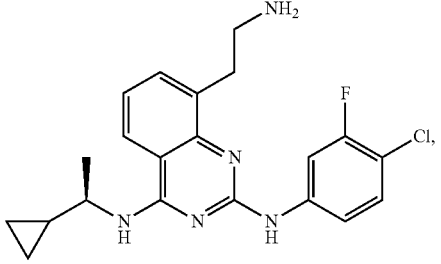
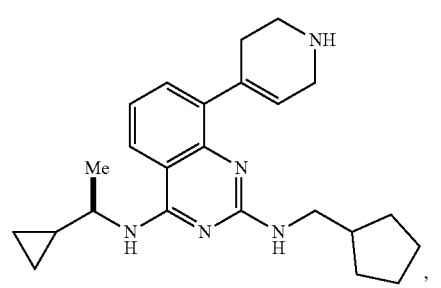
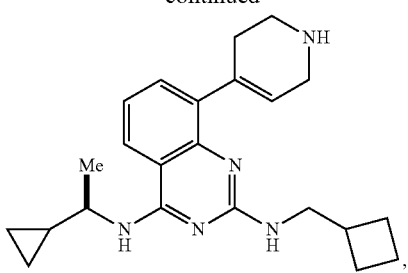
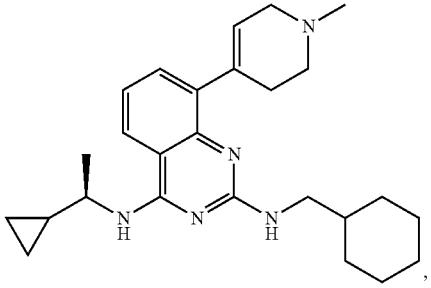
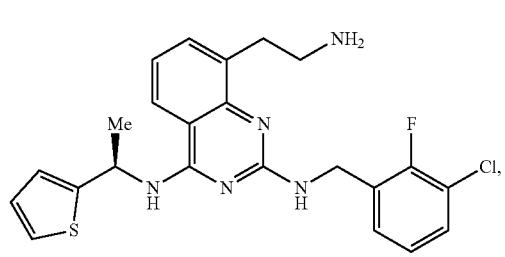
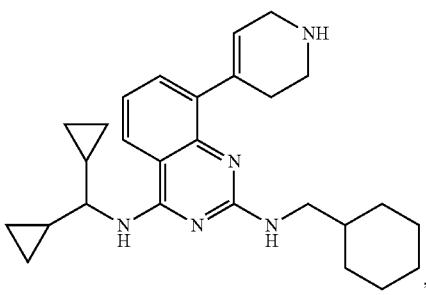
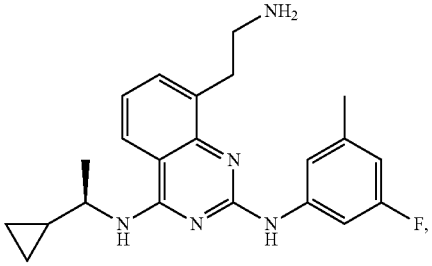
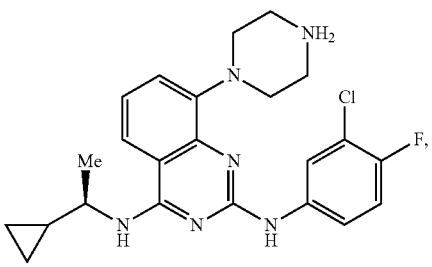

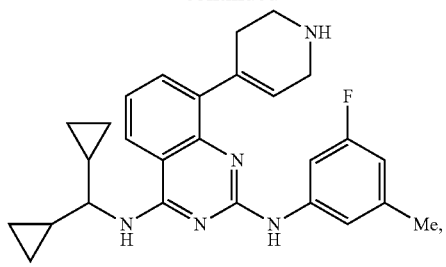
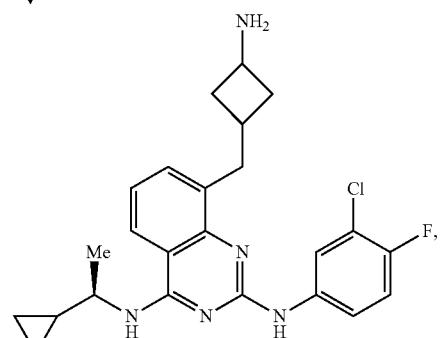
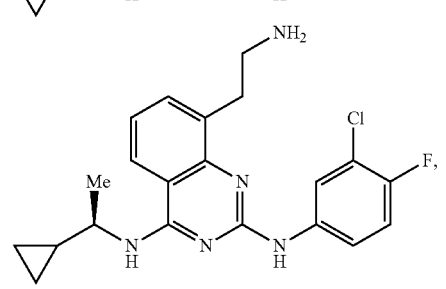
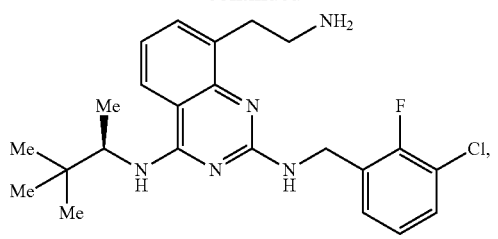
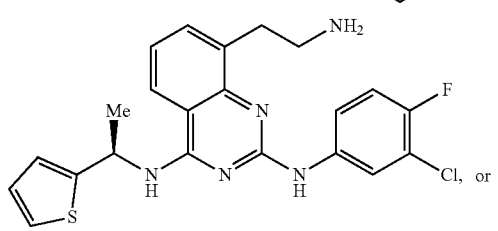
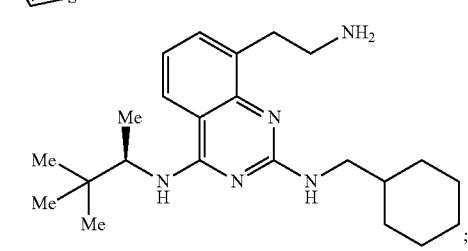
or a pharmaceutically acceptable salt thereof.
35. A compound of claim 1, of the following formula:
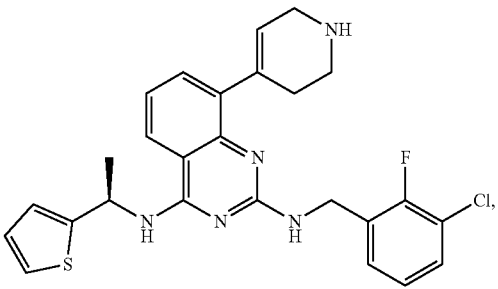
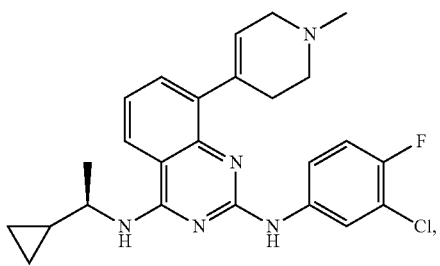
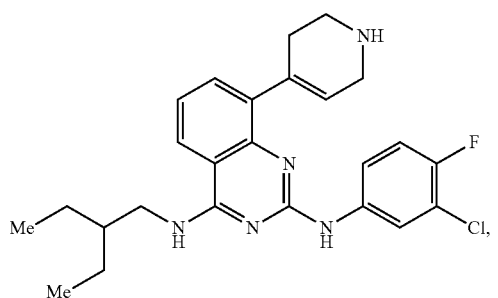

139
-continued
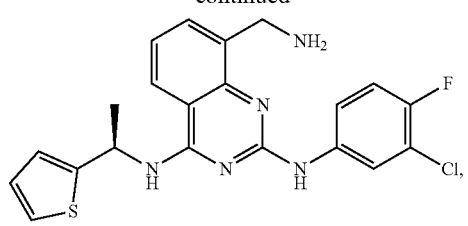
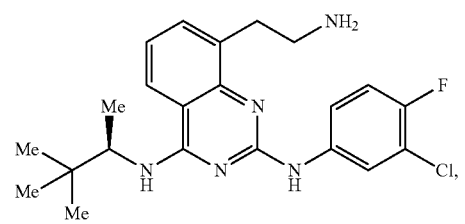
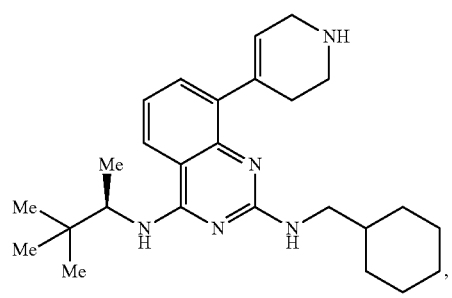
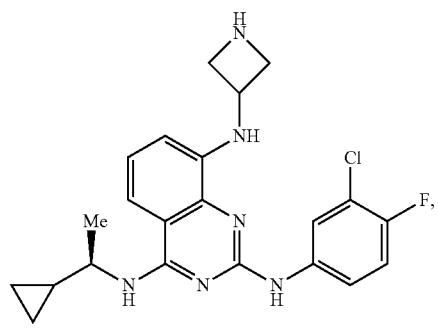
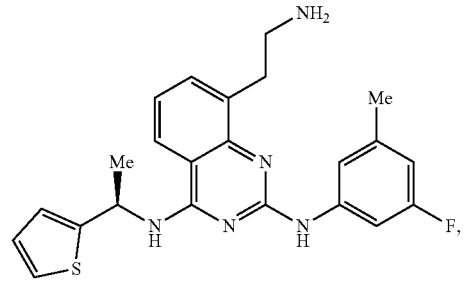
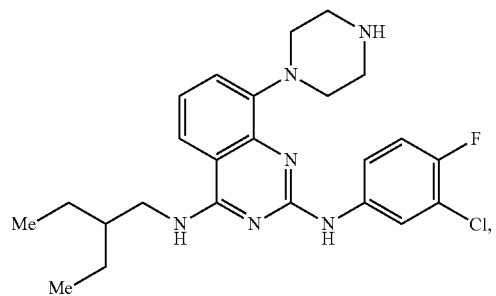
140
-continued
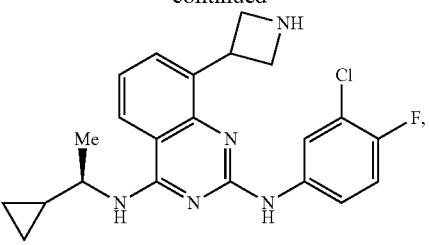
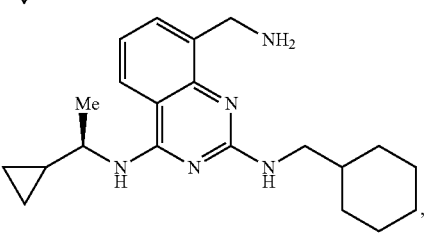
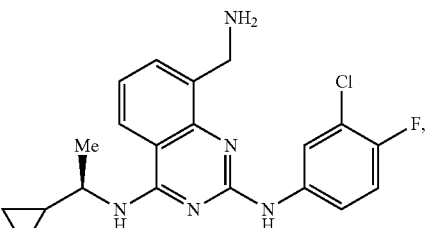
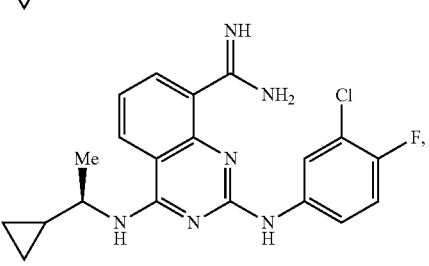
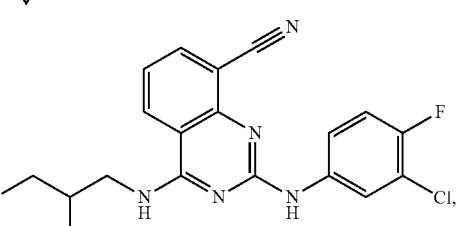
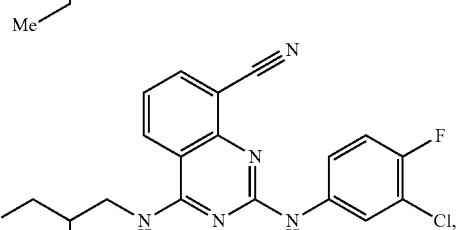
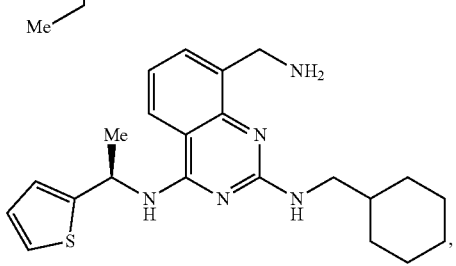

141
-continued
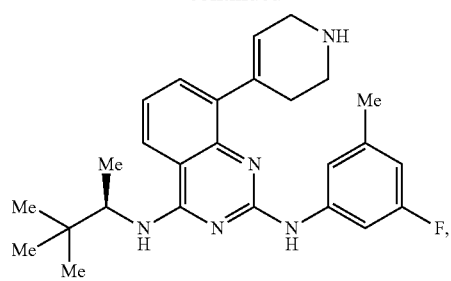
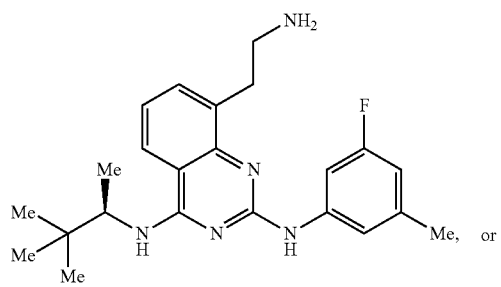
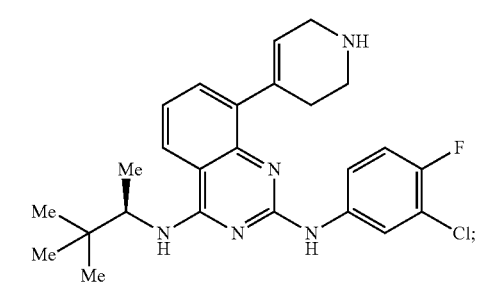
or a pharmaceutically acceptable salt thereof.
36. A compound of claim 1, of the following formula:
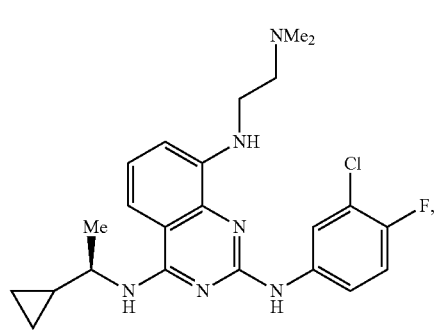
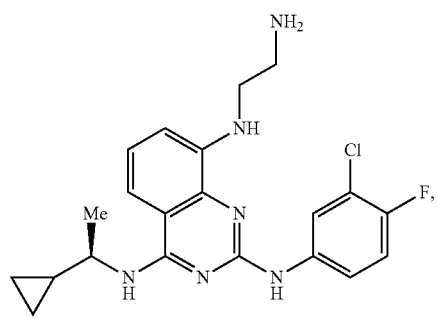
142
-continued
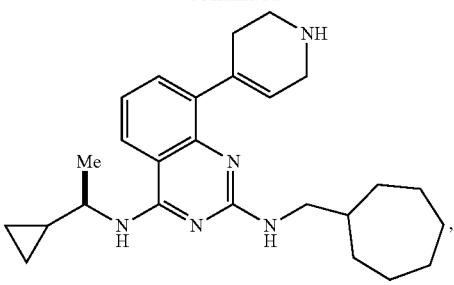
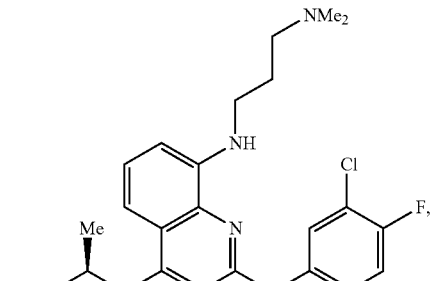
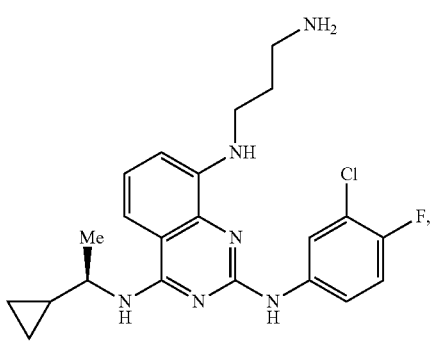
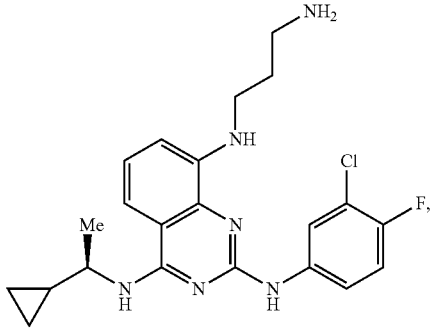
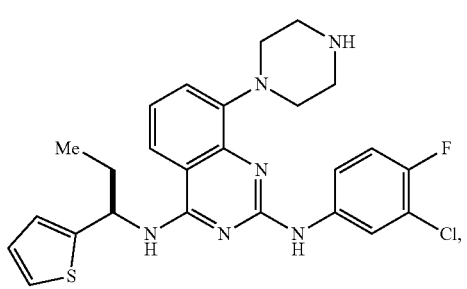

143
-continued
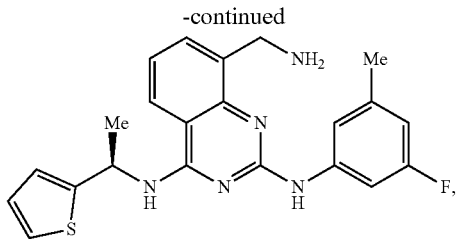
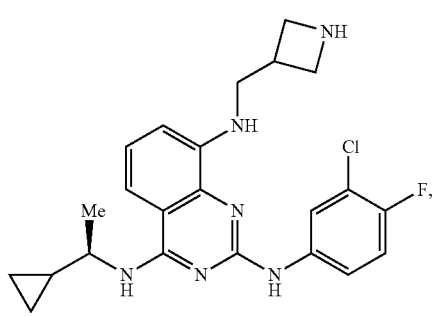
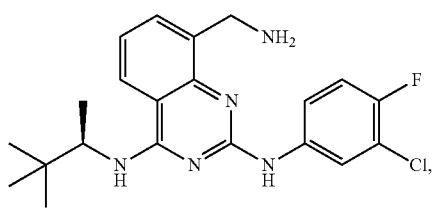
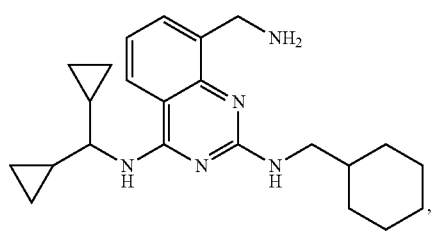
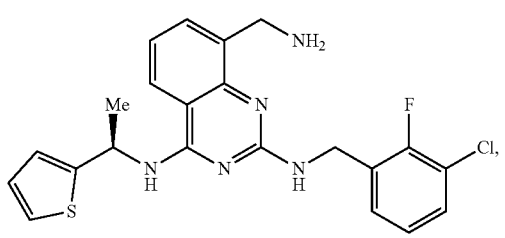
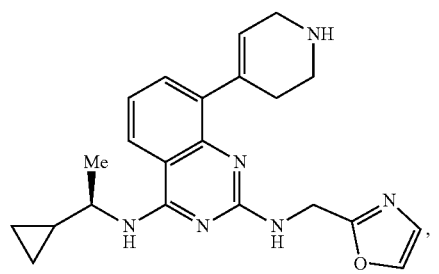
144
-continued
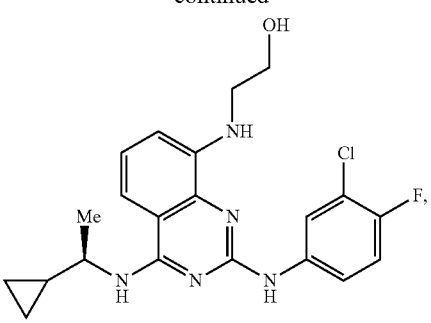
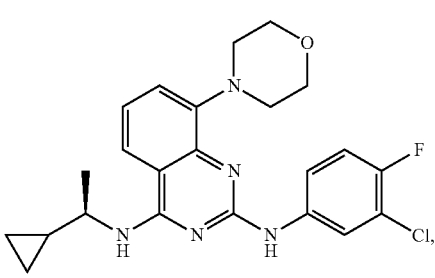
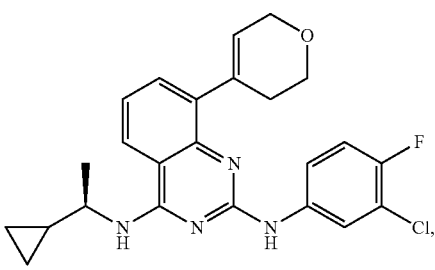
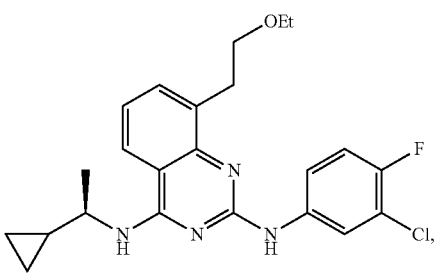
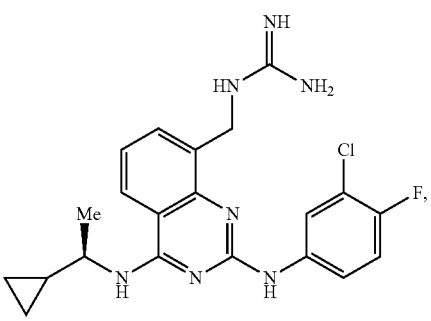
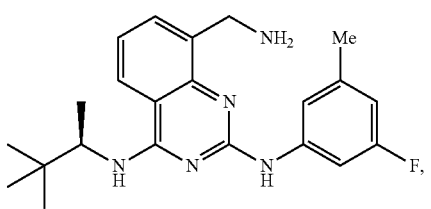

145
-continued
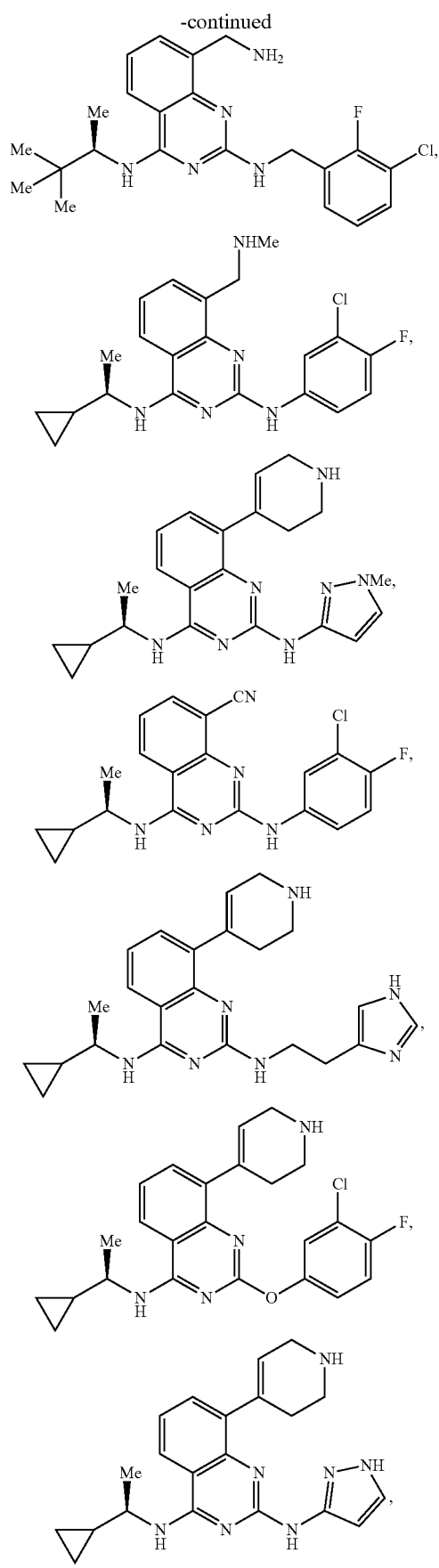
146
-continued
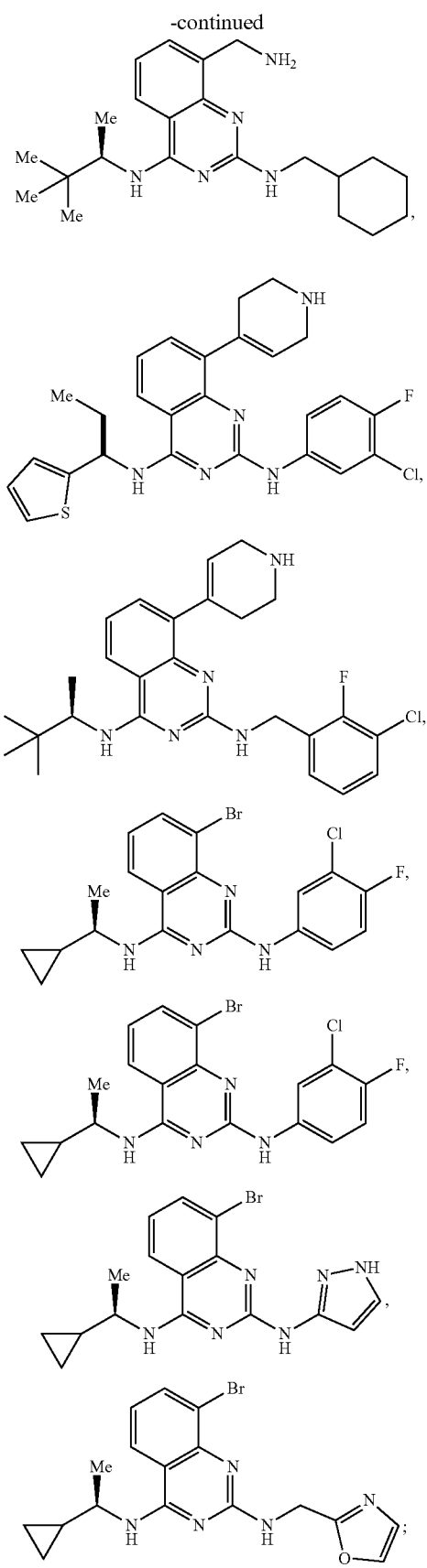
or a pharmaceutically acceptable salt thereof.

37. A compound of claim 1, of the following formula:

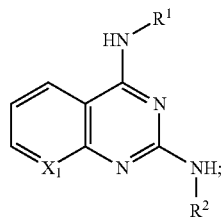

wherein $X_1$ is selected from $C_{1-6}$—$R^4$;

$R^4$ is selected from

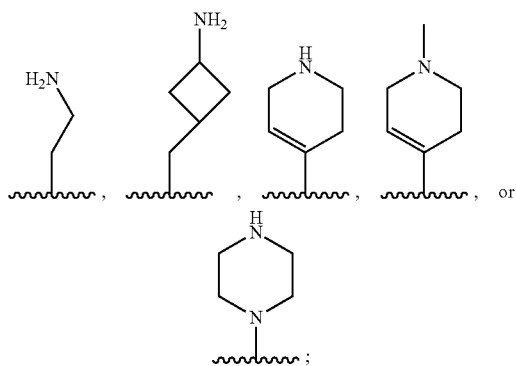

$R^1$ is optionally substituted with one or more Z and selected from alkyl-cycloalkyl, alkenyl-cycloalkyl, or alkyl-thiophene;

$R^2$ is (i) optionally substituted with one or more Z, and selected from phenyl, benzyl, alkyl-cycloalkyl; or (ii) benzyl substituted with one or more Z;

Z is independently H, alkyl, halogen;

or a pharmaceutically acceptable salt thereof or a pharmaceutically acceptable derivative thereof.

38. A compound of the following formula:

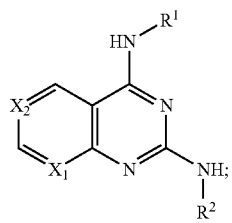

wherein $X_1$ is CH;

$X_2$ is CH or

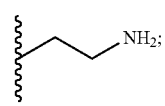 [SMILES: *CCN]

$R^1$ is optionally substituted and selected from

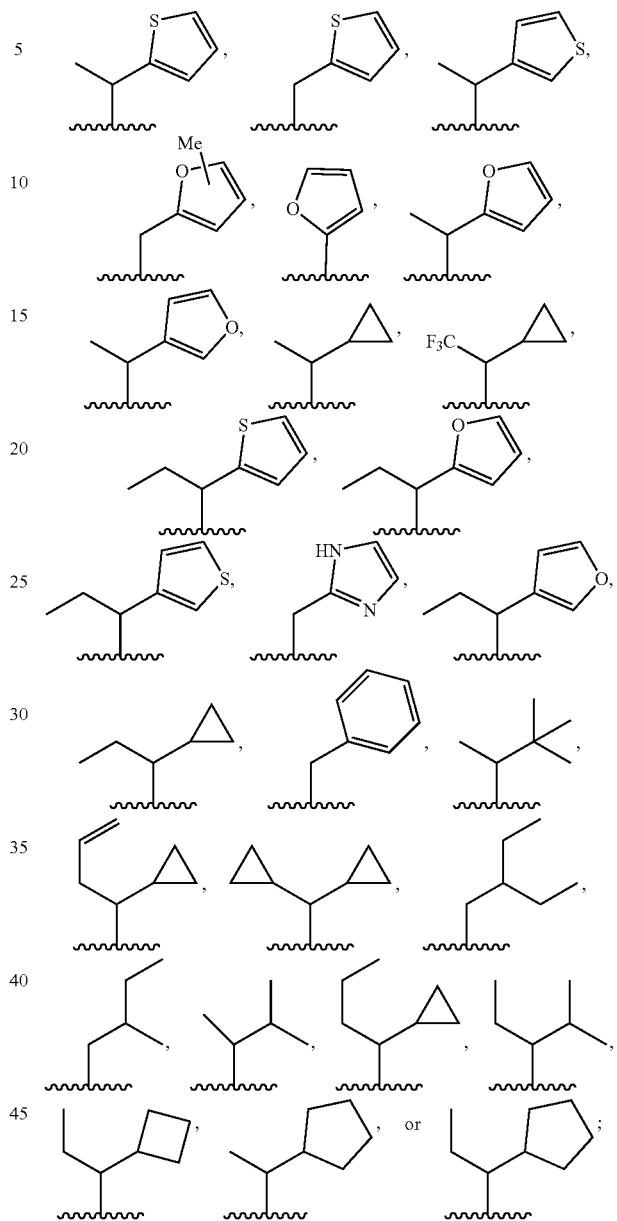

$R^2$ is (i) optionally substituted with one or more Z, and selected from phenyl, aryl, heteroaryl, alkyl-heteroalkyl, alkyl-heteroaryl, alkyl-cycloalkyl, biaryl, heterobiaryl, alkyl-biaryl, alkenyl, furanyl, thiophenyl, triazolyl, imidazolyl, pyrrolidinyl, thiazolyl, or forms a heteroalkyl ring with itself; or (ii) benzyl substituted with one or more Z;

Z is independently H, alkyl, halogen, $CF_3$, alkoxy, alkyl-alkoxy, OH, O—$CF_3$, O-Me, acetonitrile, Cl, F, Br, cyano, $CF_3$, or alkyl, including methyl, ethyl, vinyl, cyclopropyl, or more than one Z joins together to form a 5 or six membered ring;

or a pharmaceutically acceptable salt thereof or a pharmaceutically acceptable derivative thereof; provided that when $R^1$ is furan, $R^2$ is not phenyl and where and $R^1$ is benzyl, $R^2$ is not phenyl.

39. A compound of claim 38, of the following formula:
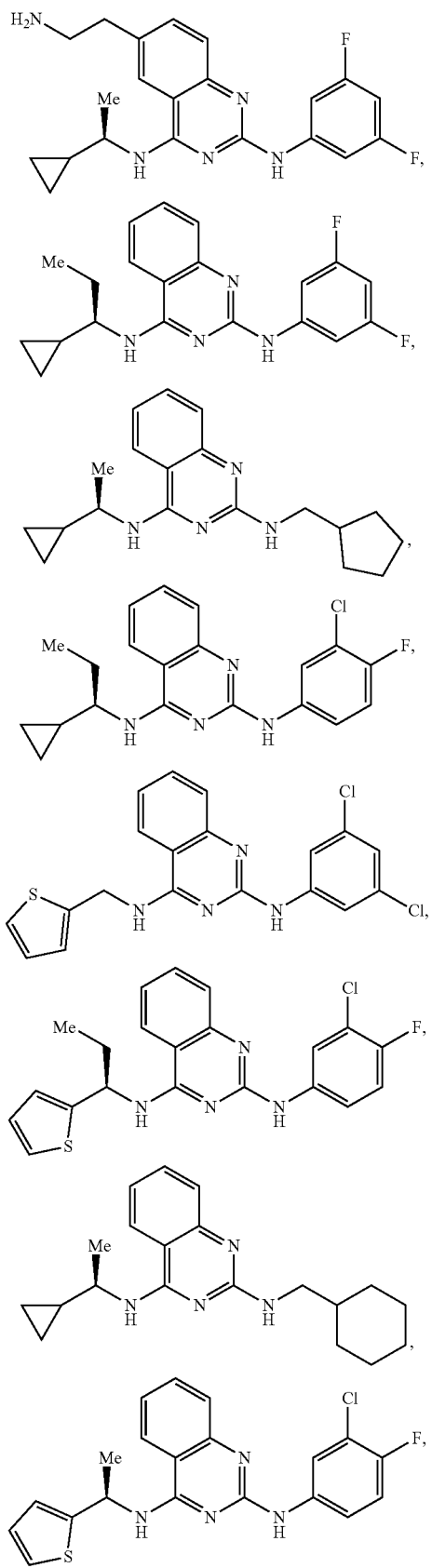
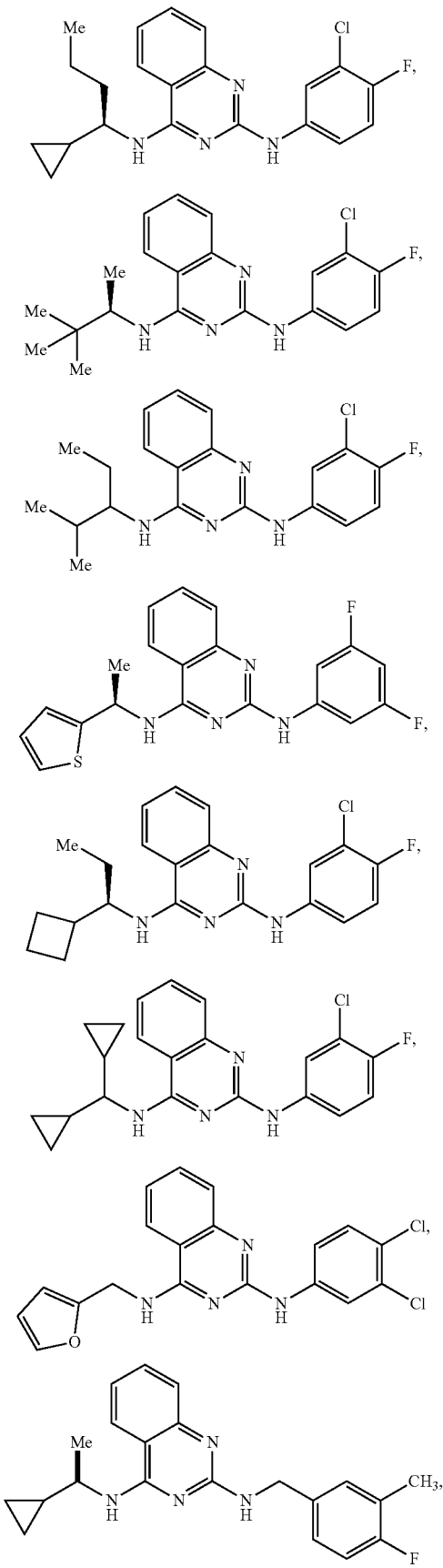

-continued
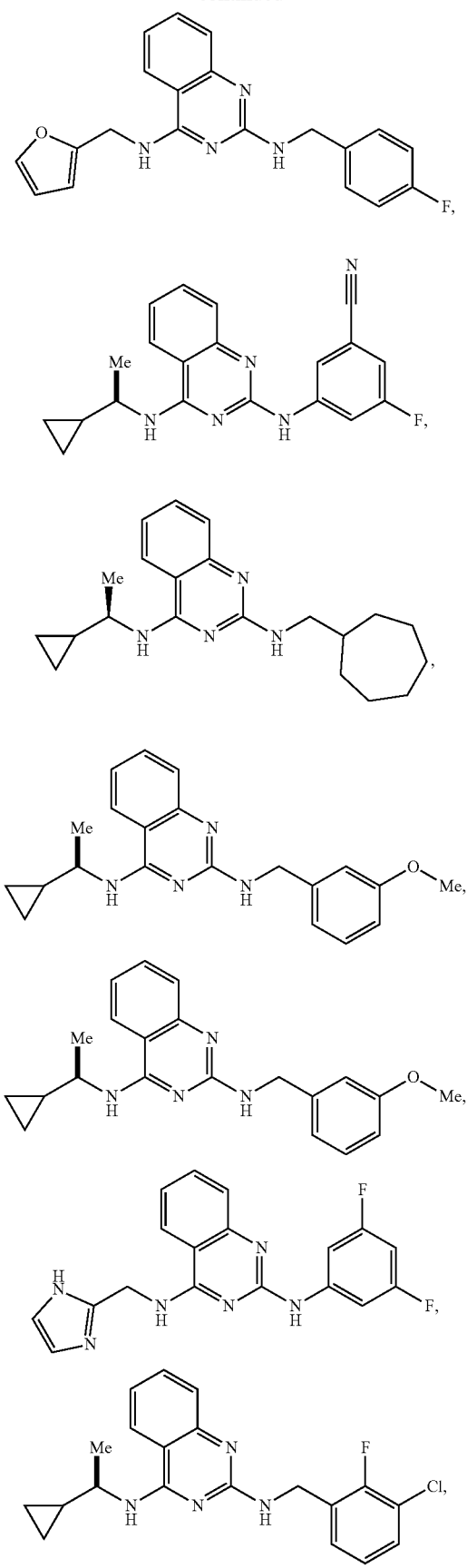
-continued
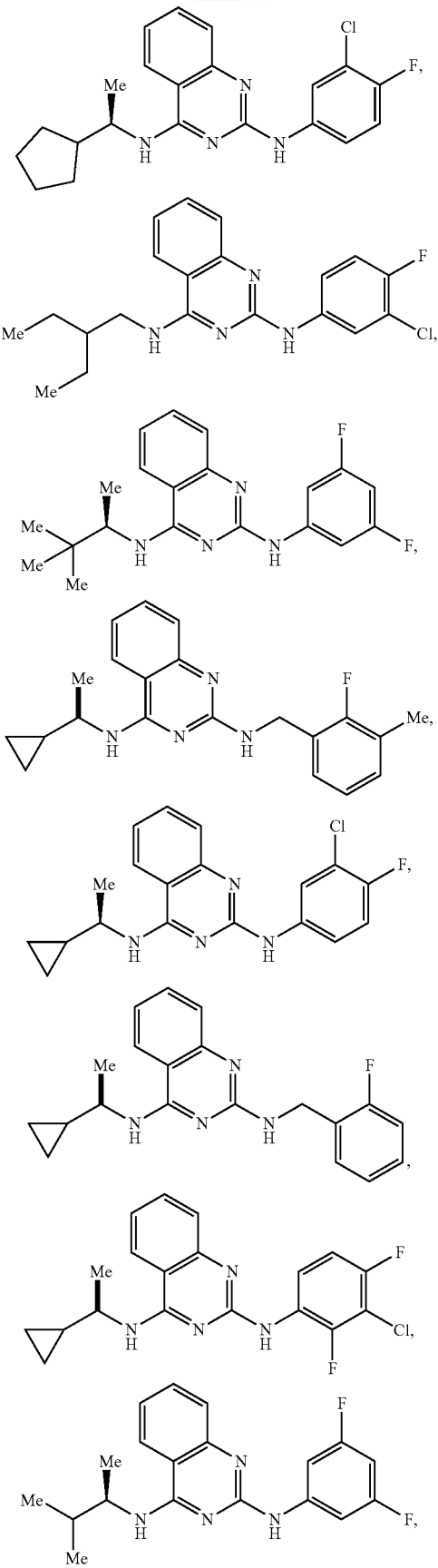

153
-continued
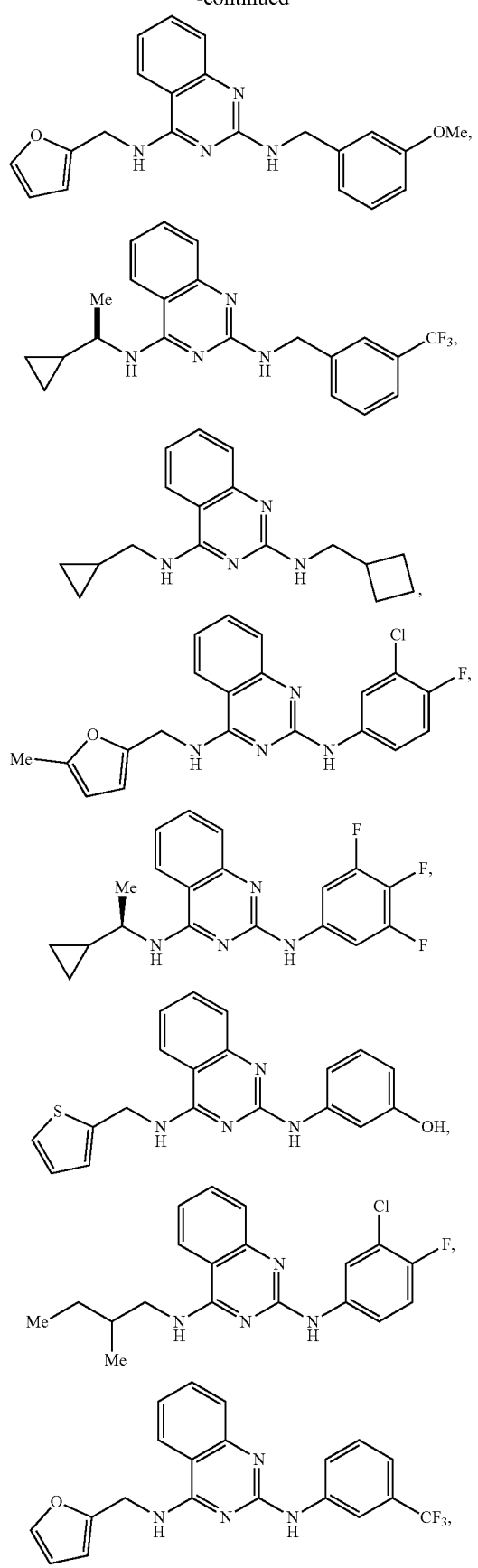
154
-continued
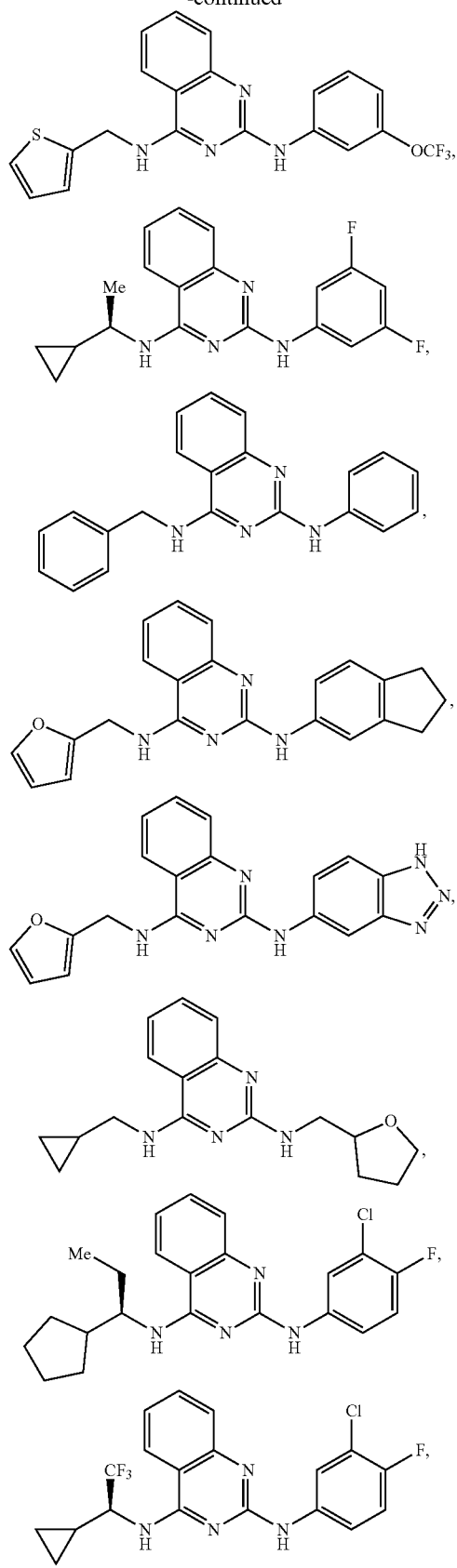
or a pharmaceutically acceptable salt thereof.

40. A method of activating nucleotide exchange on Ras in a patient in need thereof, comprising administering to the patient a Ras nucleotide exchange effective amount of a pharmaceutical composition comprising a compound of claim 38 and a pharmaceutically acceptable carrier.

41. The compound of claim 1, wherein $R^2$ is substituted benzyl, and Z is independently halogen or methyl.

* * * * *

UNITED STATES PATENT AND TRADEMARK OFFICE
CERTIFICATE OF CORRECTION

PATENT NO. : 11,318,137 B2
APPLICATION NO. : 16/500369
DATED : May 3, 2022
INVENTOR(S) : Waterson et al.

Page 1 of 1

It is certified that error appears in the above-identified patent and that said Letters Patent is hereby corrected as shown below:

In the Specification

Column 1, Insert second paragraph, with the following:
--Government Support
This invention was made with government support under Grant Nos. CA095103 and CA174419, awarded by the National Institutes of Health. The government has certain rights in the invention.--

Signed and Sealed this
Ninth Day of January, 2024

Katherine Kelly Vidal
*Director of the United States Patent and Trademark Office*